US008168757B2

(12) United States Patent
Finnefrock et al.

(10) Patent No.: US 8,168,757 B2
(45) Date of Patent: May 1, 2012

(54) PD-1 BINDING PROTEINS

(75) Inventors: Adam C. Finnefrock, Berwyn, PA (US);
Tong-Ming Fu, Maple Glen, PA (US);
Daniel C. Freed, Limerick, PA (US);
Danilo R. Casimiro, Harleysville, PA
(US); Fengsheng Li, Scarsdale, NY
(US); Aimin Tang, Lansdale, PA (US)

(73) Assignee: Merck Sharp & Dohme Corp.,
Rahway, NJ (US)

( * ) Notice: Subject to any disclaimer, the term of this
patent is extended or adjusted under 35
U.S.C. 154(b) by 0 days.

(21) Appl. No.: 12/922,066

(22) PCT Filed: Mar. 3, 2009

(86) PCT No.: PCT/US2009/035825
§ 371 (c)(1),
(2), (4) Date: Sep. 10, 2010

(87) PCT Pub. No.: WO2009/114335
PCT Pub. Date: Sep. 17, 2009

(65) Prior Publication Data
US 2011/0008369 A1    Jan. 13, 2011

Related U.S. Application Data

(60) Provisional application No. 61/069,060, filed on Mar. 12, 2008.

(51) Int. Cl.
*C07K 16/00* (2006.01)
(52) U.S. Cl. .................................. 530/387.1
(58) Field of Classification Search .................. None
See application file for complete search history.

(56) References Cited

U.S. PATENT DOCUMENTS

| 6,808,710 | B1 | 10/2004 | Wood et al. | |
| 7,029,674 | B2 * | 4/2006 | Carreno et al. | 424/130.1 |
| 7,101,550 | B2 | 9/2006 | Wood et al. | |
| 2003/0039653 | A1 | 2/2003 | Chen et al. | |
| 2004/0213795 | A1 | 10/2004 | Collins et al. | |
| 2006/0110383 | A1 | 5/2006 | Honjo et al. | |
| 2007/0065427 | A1 | 3/2007 | Freeman et al. | |
| 2007/0122378 | A1 | 5/2007 | Freeman et al. | |

FOREIGN PATENT DOCUMENTS

| WO | 2002078731 A1 | 10/2002 |
| WO | 2004056875 A1 | 7/2004 |
| WO | 2006121168 A1 | 11/2006 |
| WO | 2007005874 A2 | 1/2007 |
| WO | 2008071447 A2 | 6/2008 |
| WO | 2008156712 A2 | 12/2008 |

OTHER PUBLICATIONS

Ishida, Y. et al., "Induced Expression of PD-1, A Novel Member of the Immunoglobulin Gene Superfamily, Upon Programmed Cell Death", The EMBO Journal 1992, pp. 3887-3895, vol. 11, No. 11.
Greenwald, R.J., et al., "The B7 Family Revisited", Annu. Rev. Immunol., 2005, pp. 515-548, vol. 23.
Sharpe, A.H., et al., "The Function of Programmed Cell Death 1 and its Ligands in Regulating Autoimmunity and Infection", Nature Immunology, 2007, pp. 239-245, vol. 8, No. 3.
Parry, R.V., et al., "CTLA-4 and PD-1 Receptors Inhibit T-Cell Activation by Distinct Mechanisms", Molecular and Cellular Biology, 2005, pp. 9543-9553, vol. 25, No. 21.
Nishimura, H., et al., "Development of Lupus-like Autoimmune Disease by Disruption of the PD-1 Gene Encoding an ITIM Motif-Carrying Immunoreceptor", 1999, pp. 141-151, vol. 11.
Okazaki, T., et al., "Autoantibodies Against Cardiac Troponin I are Responsible for Dilated Cardiomyopathy in PD-1-Deficient Mice", Nature Medicine, 2003, pp. 1477-1483, vol. 9, No. 12.
Wherry, E.J., et al., Viral Persistence Alters CD8 T-Cell Immunodominance and Tissue Distribution and Results in Distinct Stages of Functional Impairment, Journal of Virology, 2003, pp. 4911-4927, vol. 77, No. 8.
Zajac, A.J., et al., "Viral Immune Evasion Due to Persistence of Activated T Cells Without Effector Function", J. Exp. Med., 1988, pp. 2205-2213, vol. 188, No. 12.
Barber, D.L., "Restoring Function in Exhausted CD8 T Cells During Chronic Viral Infection", Nature, 2006, pp. 682-687, vol. 439.
Galon, J., et al., "Type, Density, and Location of Immune Cells Within Human Colorectal Tumors Predict Clinical Outcome", Science, 1960, pp. 1960-1964, vol. 313.
Dong, H., et al., "Tumor-Associated B7-H1 Promotes T-Cell Apoptosis: A Potential Mechanism of Immune Evasion", Nature Medicine, 2002, pp. 793-800.
Blank, C., et al., "PD-L1/B7H-1 Inhibits the Effector Phase of Tumor Rejection by T Cell Receptor (TCR) Transgenic CD8 + T Cells", Cancer Res 2004; pp. 1140-1145, vol. 64.
Iwai, Y., et al., "PD-1 Blockade Inhibits Hematogenous Spread of Poorly Immunogenic Tumor Cells by Enhanced Recruitment of Effector T Cells", International Immunology, 2004, pp. 133-144, vol. 17, No. 2.
Hamanishi, J., et al., "Programmed Cell Death 1 Ligand 1 and Tumor-Infiltrating CD8 + T Lymphocytes are Prognostic Factors of Human Ovarian Cancer", PNAS, 2007, vol. 104, No. 9.
Iwai, Y., et al., "PD-1 Inhibits Antiviral Immunity at the Effector Phase in the Liver", J. Exp. Med., 2003, pp. 39-50, vol. 198 No. 1.
Hirano, F., et al., "Blockade of B7-H1 and PD-1 by Monoclonal Antibodies Potentiates Cancer Therapeutic Immunity", Cancer Res., 2005, pp. 1089-1096, vol. 65.
Keir, M.E., et al., "Tissue Expression of PD-L1 Mediates Peripheral T Cell Tolerance", JEM, 2006, pp. 883-895, vol. 203, No. 4.

* cited by examiner

*Primary Examiner* — Ilia Ouspenski
(74) *Attorney, Agent, or Firm* — Melissa B. Wenk; Sheldon O. Heber

(57) ABSTRACT

The present invention features PD-1 binding proteins, a subset of which inhibits binding of PD-L1 to the PD-1 receptor. These binding proteins can be employed to modulate the immune system through the manipulation of the PD-1 signaling pathway, enhancing host immunity to treat infections and cancer.

19 Claims, 8 Drawing Sheets

PD-1 BINDING PROTEINS

CROSS-REFERENCE TO RELATED APPLICATIONS

This application is a 371 National Stage Application of PCT/US2009/035825, with an international filing date of Mar. 3, 2009, and claims the benefit of U.S. Provisional Application No. 61/069,060 filed Mar. 12, 2008.

BACKGROUND OF THE INVENTION

The references cited throughout the present application are not admitted to be prior art to the claimed invention.

Programmed Cell Death 1 (PD-1) is a 50-55 kDa type I transmembrane receptor originally identified by subtractive hybridization of a mouse T cell line undergoing apoptosis (Ishida et al., 1992, Embo J. 11:3887-95). A member of the CD28 gene family, PD-1 is expressed on activated T, B, and myeloid lineage cells (Greenwald et al., 2005, Annu. Rev. Immunol. 23:515-48; Sharpe et al., 2007, Nat. Immunol. 8:239-45). Human and murine PD-1 share about 60% amino acid identity with conservation of four potential N-glycosylation sites and residues that define the Ig-V domain. Two ligands for PD-1 have been identified, PD ligand 1 (PD-L1) and ligand 2 (PD-L2); both belong to the B7 superfamily (Greenwald et al., 2005, supra). PD-L1 is expressed on many cell types, including T, B, endothelial and epithelial cells. In contrast, PD-L2 is narrowly expressed on professional antigen presenting cells, such as dendritic cells and macrophages.

PD-1 negatively modulates T cell activation, and this inhibitory function is linked to an immunoreceptor tyrosine-based inhibitory motif (ITIM) of its cytoplasmic domain (Greenwald et al., supra; Parry et al., 2005, Mol. Cell. Biol. 25:9543-53). Disruption of this inhibitory function of PD-1 can lead to autoimmunity. For example, PD-1 knockout in C57B1/6 mice leads to a lupus-like syndrome, whereas in BALB/c mice it leads to development of dilated cardiomyopathy (Nishimura et al., 1999, Immunity 11:141-51; Okazaki et al., 2003, Nat. Med. 9:1477-83). In humans, a single nucleotide polymorphism in PD-1 gene locus is associated with higher incidences of systemic lupus erythematosus, type 1 diabetes, rheumatoid arthritis, and progression of multiple sclerosis. The reverse scenario can also be deleterious. Sustained negative signals by PD-1 have been implicated in T cell dysfunctions in many pathologic situations, such as tumor immune evasion and chronic viral infections.

T cell responses are essential to clear viral infection; however, antiviral T cell responses are often associated with immunopathology. PD-1 mediated negative regulation is an important mechanism to limit tissue damage during clearance of viral infection by pro-inflammatory T cells. For example, PD-1 knockout mice clear adenovirus infections more efficiently but suffered more severe liver damage (Isai et al., 2003, J. Exp. Med. 198:39-50). Unfortunately, many viruses or microbes exploit the inhibitory functions of PD-1 to evade host T cell immunity (Greenwald et al., supra; Sharpe et al., supra). Sustained exposure to viral or microbial antigens during chronic infection can drive T cells to terminal differentiation with reduced capacities to proliferate and perform cytotoxic functions. The phenomenon, termed T cell "exhaustion," was first described in chronic infection of lymphocytic choriomeningitis virus (LCMV) in mice (Wherry et al., 2003, J. Virol. 77:4911-27; Zajac et al., 1998, J. Exp. Med. 188:2205-13). High-level expression of PD-1 was found to be associated with T cell dysfunctions in the LCMV model (Barber et al., 2006, Nature 439:682-7) and in human chronic viral infections, including HIV, HCV, HBV (reviewed in Sharpe et al., supra). Treatment of LCMV-infected mice with a monoclonal antibody to PD-L1, a treatment presumably blocking inhibitory signaling by PD-1, has shown therapeutic benefits of restoring multi-functions of exhausted T cells in mice (Barber et al., supra).

Host anti-tumor immunity is mainly affected by tumor-infiltrating lymphocytes (TILs) (Galore et al., 2006, Science 313:1960-4). Multiple lines of evidence have indicated that TILs are subject to PD-1 inhibitory regulation. First, PD-L1 expression is confirmed in many human and mouse tumor lines and the expression can be further upregulated by IFN-γ in vitro (Dong et al., 2002, Nat. Med. 8:793-800). Second, expression of PD-L1 by tumor cells has been directly associated with their resistance to lysis by anti-tumor T cells in vitro (Dong et al., supra; Blank et al., 2004, Cancer Res. 64:1140-5). Third, PD-1 knockout mice are resistant to tumor challenge (Iwai et al., 2005, Int. Immunol. 17:133-44) and T cells from PD-1 knockout mice are highly effective in tumor rejection when adoptively transferred to tumor-bearing mice (Blank et al., supra). Fourth, blocking PD-1 inhibitory signals by a monoclonal antibody can potentiate host anti-tumor immunity in mice (Iwai et al., supra; Hirano et al., 2005, Cancer Res. 65:1089-96). Fifth, high degrees of PD-L1 expression in tumors (detected by immunohistochemical staining) are associated with poor prognosis for many human cancer types (Hamanishi et al., 2007, Proc. Natl. Acad. Sci. USA 104:3360-5).

Vaccination is an effective method to shape the host immune system by expanding T or B cell populations specific for vaccinated antigens. The immunogenicity of vaccines is largely dependent on the affinity of host immune receptors (B-cell receptors or T-cell receptors) to antigenic epitopes and the host tolerance threshold. High affinity interactions will drive host immune cells through multiple rounds of proliferation and differentiation to become long-lasting memory cells. The host tolerance mechanisms will counterbalance such proliferation and expansion in order to minimize potential tissue damage resulting from vaccine-induced local immune activation. PD-1 inhibitory signals are part of such host tolerance mechanisms, supported by following lines of evidence. First, PD-1 expression is elevated in actively proliferating T cells, especially those with terminal differentiated phenotypes, i.e., effector phenotypes. Effector cells are often associated with potent cytotoxic function and cytokine production. Second, PD-L1 is important to maintain peripheral tolerance and to limit overly active T cells locally. Its expression is upregulated by IFN-γ and genetic knockout of PD-1 ligands in mice will incur susceptibility to diabetes in NOD background (Keir et al., 2006, J. Exp. Med. 203:883-95).

U.S. Pat. Nos. 6,808,710 and 7,101,550, issued to C. Wood and G. Freeman on Oct. 26, 2004 and Sep. 5, 2006, respectively, disclose methods for attempting to modulate an immune response by activating or inhibiting signaling of the PD-1 receptor using, for example, an antibody that binds PD-1.

Based on the observation that blocking PD-1 inhibitory signals at time of priming decreases immune cell responsiveness, U.S. Pat. No. 7,029,674, issued Apr. 18, 2006 to B. Carreno and J. Leonard, discloses methods to decrease activation of an immune cell by contacting the cell with an agent that inhibits PD-1 signaling.

Various patent applications disclose production of anti-PD-1 antibodies and/or methods of enhancing immune responses with an agent (including an anti-PD-1 antibody) that interferes with PD-L1 binding and/or PD-1 signaling, including the following: U.S. Patent Application Publication Nos. US 2003/0039653, US 2004/0213795, US 2006/0110383, US 2007/0065427, US 2007/0122378; and PCT International Application Publication Nos. WO 2006/121168, and WO 2007/005874.

SUMMARY OF THE INVENTION

PD-1 has an important role in regulating T cell responses. Immunological based strategies can be employed to modulate the immune system through the manipulation of the PD-1 signaling pathway. One such immunological based strategy includes passive immunization employing immunoglobulins targeting PD-1 that block its inhibitory signals. PD-1-specific antibodies that block PD-1 inhibitory signaling (i.e., antagonist antibodies) may enhance host anti-microbial immunity to treat chronic infections in humans. Blocking PD-1 inhibitory signals may also enhance host anti-cancer immunity by helping to nullify tumor immune evasion due to PD-L1 expression. Finally, blocking PD-1 inhibitory signaling with an anti-PD-1 antagonist antibody may have an adjuvant-like property when used in conjunction with vaccines to induce T and B cell immune responses, possibly by prolonging vaccine-induced T- or B-cell proliferation, in both prophylactic and therapeutic settings.

The present invention features PD-1 binding proteins that bind a PD-1 target region within human PD-1 (SEQ ID NO:1). PD-1 target regions are provided by the sites within human PD-1 that bind mAb 1B8, mAb 28.11, mAb 1.8A10, mAb 1G7, mAb 20B3.1, mAb 7G3, mAb 3H4, mAb 6D10 and/or mAb 2.3A9.

A subset of the monoclonal antibodies disclosed herein that bind PD-1 also block PD-L1 from binding the receptor, i.e. mAb 1B8, mAb 28.11, mAb 1.8A10, mAb 1G7, mAb 20B3.1 and mAb 7G3. Another subset of the monoclonal antibodies disclosed herein that bind PD-1 do not block the binding of PD-L1 to the receptor, i.e. mAb 3H4, mAb 6D10 and mAb 2.3A9.

A first aspect of the present invention features an isolated PD-1 binding protein comprising a first variable region and a second variable region. The first and second variable regions bind a PD-1 target region selected from the group consisting of a PD-L1-blocking target region and a PD-L1-non-blocking target region.

The monoclonal antibody mAb 1B8 is an immunoglobulin having two light chains comprising a variable domain ($V_l$) with an amino acid sequence of SEQ ID NO:5 and two heavy chains comprising a variable domain ($V_h$) with an amino acid sequence of SEQ ID NO:4. MAb 1B8 binds PD-1 with an especially high affinity and also blocks PD-L1 from binding to the receptor. Studies presented herein with mAb 1B8 indicate the potential of this antibody to reduce pathogen loads during persistent infection, as well as its utility to enhance T cell responsiveness to increase immunity in response to prophylactic and/or therapeutic vaccines. In particular, in a virus-infected rhesus model, administration of mAb 1B8 in combination with antiretroviral therapy resulted in an undetectable viral load in a subset of the tested animals. Vaccination of naïve rhesus macaques with an adenoviral vector vaccine containing SIV gag in conjunction with mAb 1B8 enhanced vaccine-induced T cell responses, even in the presence of host-generated antibodies against this murine antibody. As is generally appreciated by one skilled in the art, reducing the host-generated immune response to the antibody through various antibody optimization techniques described infra is expected to enhance or sustain efficacy. Antibodies in the same class as mAb 1B8 (i.e., compete for the same or proximate epitope within PD-1 as mAb 1B8, as described herein), and optimized versions thereof, will also be useful to enhance T cell responsiveness for the purposes described above.

The monoclonal antibody mAb 28.11 is an immunoglobulin having two light chains, each comprising one of two variable domains ($V_l$) that have an amino acid sequence selected from the group consisting of SEQ ID NO:41 and SEQ ID NO:48, and two heavy chains, each comprising one of two variable domains ($V_h$) that have an amino acid sequence selected from the group consisting of SEQ ID NO:40 and SEQ ID NO:47.

The monoclonal antibody mAb 1.8A10 is an immunoglobulin having two light chains comprising a variable domain ($V_l$) with an amino acid sequence of SEQ ID NO:35 and two heavy chains comprising a variable domain ($V_h$) with an amino acid sequence of SEQ ID NO:34.

The monoclonal antibody mAb 1G7 is an immunoglobulin having two light chains comprising a variable domain ($V_l$) with an amino acid sequence of SEQ ID NO:27 and two heavy chains comprising a variable domain ($V_h$) with an amino acid sequence of SEQ ID NO:26.

The monoclonal antibody mAb 20B3.1 is an immunoglobulin having two light chains comprising a variable domain ($V_l$) with an amino acid sequence of SEQ ID NO:13 and two heavy chains comprising a variable domain ($V_h$) with an amino acid sequence of SEQ ID NO:12.

The monoclonal antibody mAb 7G3 is an immunoglobulin having two light chains comprising a variable domain ($V_l$) with an amino acid sequence of SEQ ID NO:19 and two heavy chains comprising a variable domain ($V_h$) with an amino acid sequence of SEQ ID NO:18.

The monoclonal antibody mAb 3H4 is an immunoglobulin having two light chains comprising a variable domain ($V_l$) with an amino acid sequence of SEQ ID NO:56 and two heavy chains comprising a variable domain ($V_h$) with an amino acid sequence of SEQ ID NO:55.

The monoclonal antibody mAb 6D10 is an immunoglobulin having two heavy chains comprising a variable domain ($V_h$) with an amino acid sequence of SEQ ID NO:63 and two light chains comprising a variable domain ($V_l$).

The monoclonal antibody mAb 2.3A9 is an immunoglobulin having two light chains comprising a variable domain ($V_l$) with an amino acid sequence of SEQ ID NO:68 and two heavy chains comprising a variable domain ($V_h$) with an amino acid sequence of SEQ ID NO:67.

A "target region" is defined with respect to the region within human PD-1 (SEQ ID NO:1) bound by mAb 1B8, mAb 28.11, mAb 1.8A10, mAb 1G7, mAb 20B3.1, mAb 7G3, mAb 3H4, mAb 6D10 or mAb 2.3A9. When a PD-1 binding protein of the present invention binds to a "PD-L1-blocking target region," the subsequent binding of PD-L1 to said region is inhibited. The anti-PD-1 antibodies identified herein as mAb 1B8, mAb 28.11, mAb 1.8A10, mAb 1G7, mAb 20B3.1 and mAb 7G3 are shown to bind to the same PD-L1-blocking target region within PD-1. Thus, a PD-1 binding protein of the present invention that binds to a PD-L1-blocking target region will compete with the binding of mAbs 1B8, 28.11, 1.8A10, 1G7, 20B3.1 and/or 7G3, or an engineered version thereof with the same or similar binding characteristics (e.g., a chimeric version, see Example 10), to PD-1.

When a PD-1 binding protein of the present invention binds to a "PD-L1-non-blocking target region," PD-L1 is still capable of binding the PD-1 receptor. The anti-PD-1 antibodies identified herein as mAb 3H4, mAb 6D10 and mAb 2.3A9 bind to the same PD-L1-non-blocking target region within PD-1. Thus, a PD-1 binding protein of the present invention that binds to a PD-L1-non-blocking target region will compete with the binding of mAbs 3H4, 6D10 and/or 2.3A9, or an engineered version thereof with the same or similar binding characteristics, to PD-1. As an example, a protein that competes with mAb 1B8 binding to PD-1 binds to a PD-L1-blocking target region.

A protein that competes with either mAb 1B8, mAb 28.11, mAb 1.8A10, mAb 1G7, mAb 20B3.1, mAb 7G3, mAb 3H4, mAb 6D10 or mAb 2.3A9 reduces binding of that monoclonal antibody to human PD-1 by at least about 20%, preferably at least about 50%, when excess and equal amounts of the competing protein and monoclonal antibody are employed.

Reference to "isolated" indicates a different form than found in nature. The different form can be, for example, a different purity than found in nature and/or a structure that is not found in nature. "Isolated" naturally-occurring proteins, PD-1 binding proteins, antibodies and nucleic acid molecules as described herein will be free or substantially free of either material with which they are naturally associated, such as other polypeptides or nucleic acids found in their natural environment (e.g., serum proteins), or material in the environment in which they are prepared (e.g., cell culture) when such preparation is by recombinant DNA technology (practiced in vitro) or in vivo. A structure not found in nature includes recombinant structures where different regions are combined. This includes, for example, humanized antibodies where one or more murine complementary determining region is inserted onto a human framework scaffold or a murine antibody is resurfaced to resemble the surface residues of a human antibody, hybrid antibodies where one or more complementary determining region from a PD-1 binding protein is inserted into a different framework scaffold, and antibodies derived from natural human sequences where genes coding for light and heavy variable domains are randomly combined together.

A "variable region" has the structure of an antibody variable region from a heavy or light chain. Antibody heavy and light chain variable regions contain three complementarity determining regions ("CDRs") interspaced onto a framework ("FW"). The CDRs are primarily responsible for recognizing a particular epitope. It is well known that epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Reference to "protein" indicates a contiguous amino acid sequence and does not provide a minimum or maximum size limitation. One or more amino acids present in the protein may contain a post-translational modification, such as glycosylation or disulfide bond formation.

A preferred PD-1 binding protein of the present invention is a monoclonal antibody. Reference to a "monoclonal antibody" indicates a collection of antibodies having the same, or substantially the same, complementarity determining region and binding specificity. The variation in the antibodies is that which would occur if the antibodies were produced from the same construct(s).

Monoclonal antibodies can be produced, for example, from a particular murine hybridoma generated from the fusion of mouse myeloma and mouse spleen cells and from a recombinant cell containing one or more recombinant genes encoding the antibody. The antibody may be encoded by more than one recombinant gene wherein, for example, one gene encodes the heavy chain and one gene encodes the light chain.

Another aspect of the present invention describes a nucleic acid comprising one or more recombinant genes encoding either a PD-1 binding protein $V_h$ region or $V_l$ region, or both, wherein the PD-1 binding protein binds to a target region selected from the group consisting of a PD-L1-blocking target region and a PD-L1-non-blocking target region.

A recombinant gene contains recombinant nucleic acid encoding a protein along with regulatory elements for proper transcription and processing (which may include translational and post translational elements). The recombinant nucleic acid by virtue of its sequence and/or form does not occur in nature. Examples of recombinant nucleic acid include purified nucleic acid, two or more nucleic acid regions combined together providing a different nucleic acid than found in nature, and the absence of one or more nucleic acid regions (e.g., upstream or downstream regions) that are naturally associated with each other.

Another aspect of the present invention describes a recombinant cell comprising one or more recombinant genes encoding either an antibody binding protein $V_h$ region or $V_l$ region, or both, wherein the PD-1 binding protein binds to a target region selected from the group consisting of a PD-L1-blocking target region and a PD-L1-non-blocking target region. Multiple recombinant genes are useful, for example, where one gene encodes an antibody heavy chain or fragment thereof containing the $V_h$ region and another nucleic acid encodes an antibody light chain or fragment thereof containing the $V_l$ region. Preferably, the recombinant cell expresses both the $V_h$ and $V_l$ regions.

The present invention also comprises a method of producing a protein comprising an antibody variable region. The method comprising the steps of: (a) growing a recombinant cell comprising recombinant nucleic acid encoding for a protein under conditions wherein the protein is expressed; and (b) purifying the protein. Preferably, the protein is a complete PD-1 binding protein.

Another aspect of the present invention describes a pharmaceutical composition. The composition comprises a therapeutically effective amount of a PD-1 binding protein described herein and a pharmaceutically acceptable carrier. The composition can further comprise one or more additional substances having a medicinal effect. In one aspect of this portion of the present invention, the additional substance displays anti-microbial activity. In another aspect, the additional substance displays anti-cancer activity.

A therapeutically effective amount is an amount sufficient to provide a useful therapeutic or prophylactic effect against a particular disease or disease condition. For example, for a patient infected with a harmful bacteria or virus, an effective amount is sufficient to achieve one or more of the following therapeutic effects: reduce the ability of the bacteria or virus to propagate in the patient or reduce the amount of bacteria or viral load in the patient. With respect to anti-infective applications for an uninfected patient, an effective amount is sufficient to achieve one or more of the following prophylactic effects: a reduced susceptibility to a bacterial or viral infection or a reduced ability of an infecting bacterium or virus to establish persistent infection. In another example, a therapeutically effective amount of a PD-1 binding protein includes an amount sufficient to generate an immune response useful to provide a therapeutic or prophylactic effect against a particular disease or disease condition. For example, for a patient with cancer, an effective amount of a PD-1 binding protein includes an amount sufficient to reduce the proliferation of cancerous cells, including the growth of tumors.

Reference to a substance having "anti-microbial" activity indicates a substance that kills or inhibits the growth of a microorganism, such as bacteria, fungi or viruses. Thus, substances that inhibit microbial activity include substances displaying anti-bacterial, anti-fungal and/or anti-viral activity. These substances include, without limitation, chemical compounds, medicinal biologics and anti-microbial vaccines.

Reference to a substance having "anti-cancer" activity indicates a substance that inhibits the proliferation of cancerous cells, including substances that inhibit the growth of tumors. Substances that display anti-cancer activity include, without limitation, substances having cytotoxic chemotherapeutic effects and anti-cancer vaccines.

Another aspect of the present invention describes a method of detecting the presence of a PD-1 protein in a solution or on a cell. The method involves providing a PD-1 binding protein described herein to the solution or cell and measuring the ability of the protein to bind to a PD-1 protein in the solution or cell. Measurements can be quantitative or qualitative.

Reference to a human PD-1 protein includes full-length PD-1 that is recognized by mAb 1B8, mAb 28.11, mAb 1.8A10, mAb 1G7, mAb 20B3.1, mAb 7G3, mAb 3H4, mAb 6D10 or mAb 2.3A9.

Another aspect of the present invention features methods of enhancing the cellular immune response in a subject comprising administering a PD-1 binding protein to said subject for a variety of therapeutic and/or prophylactic treatments. The cellular immune response can include a T-cell response, including a cytolytic T-cell ("CTL") response and/or a helper T-cell response. For example, the present invention relates to methods of treating a patient against a microbial infection comprising the step of administering to the patient an effective amount of a PD-1 binding protein, or composition thereof, as described herein. The PD-1 binding protein can be administered alone or in combination with additional anti-microbial substances. The patient may or may not be infected with a microorganism at the time of administration. Another aspect of the present invention relates to methods of treating a patient suffering from cancer or susceptible to developing cancer comprising the step of administering to the patient an effective amount of a PD-1 binding protein, or composition thereof, as described herein. The PD-1 binding protein can be administered alone or in combination with additional anti-cancer substances. Administration of a PD-1 binding protein, or composition thereof, as described herein, is useful as both a monotherapy or as part of a therapeutic regime, said regime comprising subsequent administration or co-administration of additional substances having, for example, additional medicinal effects (e.g., anti-microbial and/or anti-cancer activity).

Reference to a "cellular immune response" in the context of the present invention is an immunological response mediated by T-lymphocytes and/or other white blood cells. One important aspect of cellular immunity involves an antigen-specific response by cytolytic T-cells ("CTLs"). CTLs induce and promote the destruction of intracellular microbes, or the lysis of cells infected with such microbes. Another aspect of cellular immunity involves an antigen-specific response by helper T-cells. A cellular immune response also refers to the production of cytokines, chemokines and other such molecules produced by activated T-cells and/or other white blood cells, including those derived from CD4+ and CD8+ T-cells.

Reference to a "microbial infection" in the context of the present invention means an infection where the infectious microbial agent (e.g., virus, bacterium, parasite, mycoplasm, fungus) is present. Persistent microbial infections are those which are not effectively cleared or eliminated from the host, even after the induction of an immune response. Persistent infections may be chronic infections and/or latent infections. Microbial infections may last for months, years or even a lifetime. Microbial infections may recur, involving stages of silent and productive infection without cell killing or even producing excessive damage to host cells.

Another aspect of the present invention describes a cell line producing a protein that is either mAb 1B8, mAb 28.11, mAb 1.8A10, mAb 1G7, mAb 20B3.1, mAb 7G3, mAb 3H4, mAb 6D10 or mAb 2.3A9, or that competes with the binding of either mAb 1B8, mAb 28.11, mAb 1.8A10, mAb 1G7, mAb 20B3.1, mAb 7G3, mAb 3H4, mAb 6D10 or mAb 2.3A9 to PD-1. Preferred cells lines are hybridomas and recombinant cell lines containing recombinant nucleic acid encoding the protein.

Reference to open-ended terms such as "comprises" allows for additional elements or steps. Occasionally phrases such as "one or more" are used with or without open-ended terms to highlight the possibility of additional elements or steps.

Unless explicitly stated reference to terms such as "a" or "an" is not limited to one. For example, "a cell" does not exclude "cells." Occasionally phrases such as one or more are used to highlight the possible presence of a plurality.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

The present disclosure provides anti-PD-1 antibodies that comprise novel PD-1 binding proteins. These PD-1 binding proteins can act as antagonists to PD-1 activity, thereby attenuating or blocking PD-1 inhibitory signals that negatively modulate T cell activation. A PD-1 binding protein with the capability of blocking PD-1 inhibitory signals has potential uses in a variety of clinical applications, including enhancing host anti-microbial immunity when treating persistent infections, nullifying tumor immune evasion to enhance host anti-cancer immunity, and providing adjuvant-like properties when combined with vaccines for induction of cellular immune responses.

I. PD-1 Binding Proteins

PD-1 binding proteins contain an antibody variable region providing for specific binding to a PD-1 epitope. The antibody variable region can be present in, for example, a complete antibody, an antibody fragment, and a recombinant derivative of an antibody or antibody fragment. The term "antibody" describes an immunoglobulin, whether natural or partly or wholly synthetically produced. Thus, PD-1 binding proteins of the present invention include any polypeptide or protein having a binding domain which is, or is substantially identical to (e.g., at least 95% identical to), an antibody variable region described herein that is specific for binding to a PD-1 epitope.

Figure 1:
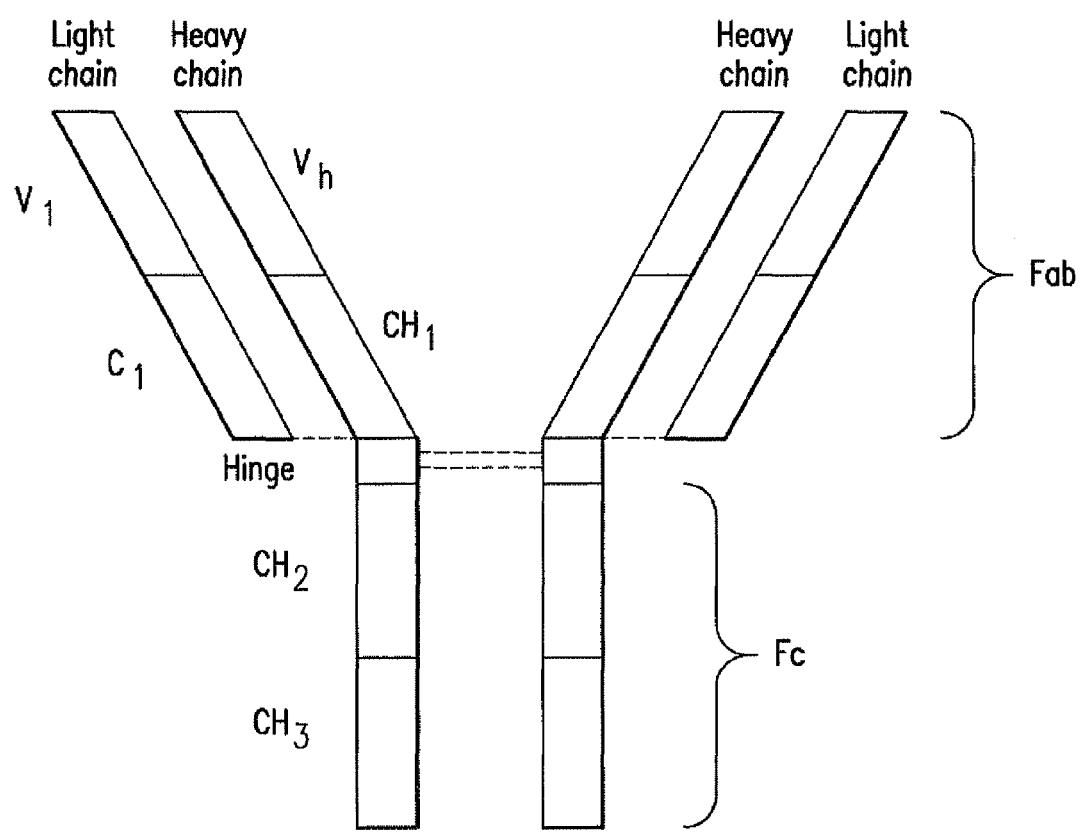
FIG. 1 illustrates the structure of an IgG antibody molecule. "$V_l$" refers to a light chain variable region. "$V_h$" refers to a heavy chain variable region. "$C_l$" refers to a light chain constant region. "$CH_1$," "$CH_2$" and "$CH_3$" are heavy chain constant regions. Dashed lines indicate disulfide bonds.

Different classes of antibodies have different structures. Different antibody regions can be illustrated by reference to IgG (FIG. 1). An IgG molecule contains four amino acid chains, two longer length heavy chains and two shorter light chains that are inter-connected by disulfide bonds. The heavy and light chains each contain a constant region and a variable region. A heavy chain is comprised of a heavy chain variable region ($V_h$) and a heavy chain constant region ($CH_1$, $CH_2$ and $CH_3$). A light chain is comprised of a light chain variable region ($V_l$) and a light chain constant region ($C_l$). There are three hypervariable regions within the variable regions that are responsible for antigen specificity. (See, for example, Breitling et al., Recombinant Antibodies, John Wiley & Sons, Inc. and Spektrum Akademischer Verlag, 1999; and Lewin, Genes IV, Oxford University Press and Cell Press, 1990.)

The hypervariable regions are generally referred to as complementarity determining regions ("CDR") and are interposed between more conserved flanking regions referred to as framework regions ("FW"). There are four (4) FW regions and three (3) CDRs that are arranged from the $NH_2$ terminus to the COOH terminus as follows: FW1, CDR1, FW2, CDR2, FW3, CDR3, FW4. Amino acids associated with framework regions and CDRs can be numbered and aligned by approaches described by Kabat et al., Sequences of Proteins of Immunological Interest, U.S. Department of Health and Human Services, 1991; C. Chothia and A. M. Lesk, Canonical structures for the hypervariable regions of immunoglobulins, *Journal of Molecular Biology* 196(4):901 (1987); or B. Al-Lazikani, A. M. Lesk and C. Chothia, Standard conformations for the canonical structures of immunoglobulins, *Journal of Molecular Biology* 273(4): 27, 1997. For example, the framework regions and CDRs can be identified from consideration of both the Kabat and Chothia definitions. The variable regions of the heavy and light chains contain a binding domain that interacts with an antigen.

The two heavy chain carboxyl regions are constant regions joined by disulfide bonding to produce an Fc region. The Fc region is important for providing effector functions. (Presta, *Advanced Drug Delivery Reviews* 58:640-656, 2006.) Each of the two heavy chains making up the Fc region extends into different Fab regions through a hinge region.

In higher vertebrates, there are two classes of light chains and five classes of heavy chains depending on the amino acid sequence of the constant domains of the chains. The light chains are designated as either κ (kappa) or λ (lambda). There are five major classes of immunoglobulin heavy chains that define the antibody class and are designated as either α (alpha or A), δ (delta or D), ε (epsilon or E), γ (gamma or G), or μ (mu or M). For example, IgG has a γ heavy chain. Subclasses or isotypes also exist for different types of heavy chains such as human $\gamma_1$, $\gamma_2$, $\gamma_3$, and $\gamma_4$. Heavy chains impart a distinctive conformation to the hinge and tail regions. (Lewin, Genes IV, Oxford University Press and Cell Press, 1990.)

It is known in the art that it is possible to manipulate monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. A hybridoma or other cell producing an antibody may be subject to genetic mutation or other changes, which may or may not alter the binding specificity of antibodies produced. To this end, the term antibody covers antibody fragments, derivatives, functional equivalents and homologues of antibodies.

Antibody fragments of the present invention contain an antibody variable region. Such antibody fragments include but are not limited to (i) a Fab fragment, a monovalent fragment consisting of the $V_h$, $V_l$, $C_h$ and $C_l$ domains; (ii) a $Fab_2$ fragment, a bivalent fragment comprising two Fab fragments linked by a disulfide bridge at the hinge region; (iii) a Fd fragment consisting of the $V_h$ and $C_{h1}$ domains; (iv) a Fv fragment consisting of the $V_h$ and $V_l$ domains of a single arm of an antibody; (v) a dAb fragment, which comprises either a $V_h$ or $V_l$ domain; (vi) a scAb, an antibody fragment containing $V_h$ and $V_l$ as well as either $C_l$ or $C_{h1}$; and, (vii) artificial antibodies based upon protein scaffolds, including but not limited to fibronectin type III polypeptide antibodies (e.g., see U.S. Pat. No. 6,703,199, issued to Koide on Mar. 9, 2004 and PCT International Application publication no. WO 02/32925). Furthermore, although the two domains of the Fv fragment, $V_l$ and $V_h$, are coded for by separate genes, they can be joined using recombinant methods by a synthetic linker that enables them to be made as a single protein chain in which the $V_l$ and $V_h$ regions pair to form monovalent molecules (known as single chain Fv (scFv).

Thus, the antibody variable region can be present in a recombinant derivative. Examples of recombinant derivatives include single-chain antibodies, diabody, triabody, tetrabody, and miniantibody (Kipriyanov et al, *Molecular Biotechnology* 26:39-60, 2004). A PD-1 binding protein of the present invention can also contain one or more variable regions recognizing the same or different epitopes (Kipriyanov et al., 2004, supra).

II. Generation of PD-1 Binding Proteins Directed to an Identified Target Region

PD-1 binding proteins directed to a PD-L1-blocking target region or a PD-L1-non-blocking target region can be obtained using different techniques, such as those making use of the identified PD-1 binding proteins that bind to the identified target regions and screening for additional binding proteins that bind the same target regions. The ability of an antibody to bind the identified target regions can be evaluated using a surface plasmon resonance assay (e.g., Biacore®) and mAb 1B8, mAb 28.11, mAb 1.8A10, mAb 1G7, mAb 20B3.1, mAb 7G3, mAb 3H4, mAb 6D10 or mAb 2.3A9 (see Examples 2 and 6, infra), or an engineered version thereof with the same or similar binding affinity. PD-1 binding proteins that bind to the identified target regions can be used in different ways for obtaining additional binding proteins, such as using sequence information from the PD-1 binding proteins and/or modifying the PD-1 binding proteins.

II.A. Variable Region Design

Variable regions for the PD-1 binding proteins of the present invention can be designed based upon the variable regions that bind the PD-L1-blocking or PD-L1-non-blocking target regions, as described herein. Based on surface plasmon resonance studies, mAbs designated 1B8, 28.11, 1.8A10, 1G7, 20B3.1 and 7G3 were each found to bind PD-1 and block PD-L1 ligand binding to PD-1 (see Example 2, infra). The same studies found that mAbs designated 3H4, 6D10 and 2.3A9 bind PD-1 but do not prevent PD-L1 from binding the receptor. Epitope footprinting assays (see Example 6, infra) analyzing mAbs 20B3.1, 28.11, 1B8, 1.8A10, 3H4, 7G3, 1G7, 6D10 and 2.3A9 found that mAbs 3H4, 6D10 and 2.3A9 have a distinct epitope from the other mAbs. MAbs 20B3.1, 28.11, 1B8, 1.8A10, 7G3 and 1G7 competed for the same epitope within PD-1, while mAbs 6D10, 3H4 and 2.3A9 also competed for a same epitope within PD-1, yet different from the PD-L1-blocking epitope. Thus, the target region within PD-1 that binds mAbs 20B3.1, 28.11, 1B8, 1.8A10, 7G3 and/or 1G7 is defined as a PD-L1-blocking target region. The target region within PD-1 that binds mAbs 3H4, 6D10 and/or 2.3A9 is defined as a PD-L1-non-blocking target region.

The amino acid sequences for the heavy chain variable domain and/or the light chain variable domain of mAb 1B8, mAb 20B3.1, mAb 7G3, mAb 3H4, mAb 2.3A9, mAb 1G7, mAb 1.8A10, mAb 28.11, and mAb 6D10 are disclosed in Example 4 (infra). As explained in Example 4, two light chain variable domain sequences and two heavy chain variable domain sequences were cloned from the hybridoma that produces mAb 28.11. It is thought that one of both the two light chain sequences and the two heavy chain sequences represents a non-functional pseudogene. Thus, there are two identified $V_l$ and $V_h$ sequences for mAb 28.11 designated herein as $V_l$ 28.11.1, $V_l$ 28.11.2, $V_h$ 28.11.1 and $V_h$ 28.11.2.

Table 1 provides a summary of the variable heavy chain ($V_h$) and/or variable light chain ($V_l$) sequence identification numbers (SEQ ID NOs).

TABLE 1

| mAb | $V_h$ SEQ ID NO: | $V_l$ SEQ ID NO: |
|---|---|---|
| 1B8 | 4 | 5 |
| 20B3.1 | 12 | 13 |
| 7G3 | 18 | 19 |
| 28.11 | 40 (28.11.1) | 41 (28.11.1) |
|  | 47 (28.11.2) | 48 (28.11.2) |
| 1G7 | 26 | 27 |
| 1.8A10 | 34 | 35 |
| 3H4 | 55 | 56 |
| 6D10 | 63 | ND |
| 2.3A9 | 67 | 68 |

ND: not determined

CDRs are primarily responsible for binding to a particular epitope. Within a particular CDR, there are a few specificity determining residues (SDRs) which are of greater importance for binding to an epitope (see Kashmiri et al., *Methods* 36:25-34, 2005; Presta, *Advanced Drug Delivery Reviews* 58:640-656, 2006). SDRs can be identified, for example, through the help of target protein-antibody three-dimensional structures and mutational analysis of antibody combining sites. (Kashmiri et al., 2005, supra.) Thus, the PD-1 binding proteins of the present invention do not always require both a variable heavy chain and light chain domain to render PD-1 specificity but may only need a single CDR loop or a fragment of a functional antibody (see, e.g., Xu and Davis, 2000, *Immunity* 13:37-45 and Levi et al., 1993, *Proc. Natl. Acad. Sci. USA* 90:4374-78 (for CDR3 specificity); Williams et al., 1989, *Proc. Natl. Acad. Sci. USA* 86:5537-41 (CDR2 specificity); and, Welling et al., 1991, *J. Chromatography* 548:235-42 (10 amino acid miniantibody).

The framework regions help provide an overall structure and are more tolerant of different amino acid variations than CDRs. A variety of different naturally occurring framework regions are well-know in the art (see, e.g., Kabat et al., *Sequences of Proteins of Immunological Interest*, U.S. Department of Health and Human Services, 1991).

The CDR sequences contained within the variable heavy and/or variable light chain domains for mAb 1B8, mAb 20B3.1, mAb 7G3, mAb 3H4, mAb 2.3A9, mAb 1G7, mAb 1.8A10, mAb 28.11, and mAb 6D10 are underlined within the $V_h$ and/or $V_l$ sequences disclosed in Example 4. Table 2 provides a summary of the CDR sequence identification numbers (SEQ ID NOs). SEQ ID NO:9 and SEQ ID NO:11 represent the $V_l$ CDR1 and CDR3 sequences, respectively, for both mAb 1B8 and mAb 20B3.1. SEQ ID NO:24 represents the $V_l$ CDR2 sequence for mAb 7G3, mAb 1.8A10 and the $V_l$ 28.11.1 of mAb 28.11. SEQ ID NO:25 represents the $V_l$ CDR3 sequence for both mAb 7G3 and mAb 1.8A10.

TABLE 2

|  | Light Chain Variable Region | | | Heavy Chain Variable Region | | |
|---|---|---|---|---|---|---|
| mAb | CDR$_1$ SEQ ID NO: | CDR$_2$ SEQ ID NO: | CDR$_3$ SEQ ID NO: | CDR$_1$ SEQ ID NO: | CDR$_2$ SEQ ID NO: | CDR$_3$ SEQ ID NO: |
| 1B8 | 9 | 10 | 11 | 6 | 7 | 8 |
| 20B3.1 | 9 | 17 | 11 | 14 | 15 | 16 |
| 7G3 | 23 | 24 | 25 | 20 | 21 | 22 |
| 28.11 |  |  |  |  |  |  |
| (28.11.1) | 45 | 24 | 46 | 42 | 43 | 44 |
| (28.11.2) | 52 | 53 | 54 | 49 | 50 | 51 |
| 1G7 | 31 | 32 | 33 | 28 | 29 | 30 |
| 1.8A10 | 39 | 24 | 25 | 36 | 37 | 38 |

TABLE 2-continued

|  | Light Chain Variable Region | | | Heavy Chain Variable Region | | |
| --- | --- | --- | --- | --- | --- | --- |
| mAb | CDR$_1$ SEQ ID NO: | CDR$_2$ SEQ ID NO: | CDR$_3$ SEQ ID NO: | CDR$_1$ SEQ ID NO: | CDR$_2$ SEQ ID NO: | CDR$_3$ SEQ ID NO: |
| 3H4 | 60 | 61 | 62 | 57 | 58 | 59 |
| 6D10 | ND | ND | ND | 64 | 65 | 66 |
| 2.3A9 | 72 | 73 | 74 | 69 | 70 | 71 |

ND: not determined

II.B. Additional PD-1 Binding Proteins

Additional binding proteins targeting the PD-L1-blocking target region or the PD-L1-non-blocking target region can be obtained using full-length PD-1 or a polypeptide that provides the epitope recognized by the respective antibody variable domains described herein. A variety of techniques are available to select for a protein recognizing an epitope and/or antigen. Examples of such techniques include the use of phage display technology and hybridoma production.

To make hybridoma cells, lymphocytes from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused and selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using a relevant portion of the antigen.

The sequences identified in Tables 1 and 2 (supra), and disclosed in Example 4 (infra), provide examples of different variable region CDRs and framework sequences for PD-1 binding proteins of the present invention. Additional binding proteins recognizing PD-1 can be produced based on these identified antibody variable regions. The variable region sequence information can be used to produce additional binding proteins by, for example, modifying an existing monoclonal antibody. Thus, alterations can be made to both framework regions and CDRs and still retain specificity for the particular identified target region for binding to PD-1. Protein construction and sequence manipulation can be performed using recombinant nucleic acid techniques.

In one embodiment of the present invention, additional anti-PD-1 antibodies targeting the PD-L1-blocking target region or the PD-L1-non-blocking target region can be produced by using an identified V$_l$ or V$_h$ domain (identified by the sequences disclosed in Example 4, infra) to screen a library of the complimentary variable domains by well known methods (see, e.g., Portolano et al., 1993, *Journal of Immunology* 150:880-887; Clarkson et al., 1991, *Nature* 352:624-628). In a further embodiment of this portion of the present invention, one, two or all three of the CDR sequences identified herein (disclosed in Example 4, infra) can be used to produce functional variations of the mAbs disclosed herein (see, e.g., Söderlind et al., 2000, *Nat. Biotech.* 18:852-856).

The monoclonal antibodies mAb 1B8, mAb 28.11, mAb 1.8A10, mAb 1G7, mAb 20B3.1, mAb 7G3, mAb 3H4, mAb 6D10 and mAb 2.3A9 are murine antibodies. For human therapeutic applications, preferred binding proteins based on such mAbs are designed to reduce the potential generation of human anti-mouse antibodies recognizing the murine regions. The potential generation of human anti-mouse antibodies can be reduced using techniques such as murine antibody humanization, de-immunization, and chimeric antibody production. (See, for example, O'Brien et al., Humanization of Monoclonal Antibodies by CDR Grafting, p 81-100, From *Methods in Molecular Biology* Vol. 207: Recombinant antibodies for Cancer Therapy: Methods and Protocols (Eds. Welschof and Krauss) Humana Press, Totowa, N.J., 2003; Kipriyanov et al., *Molecular Biotechnology* 26:39-60, 2004; Gonzales et al., *Tumor Biol.* 26:31-43, 2005, Presta, *Advanced Drug Delivery Reviews* 58:640-656, 2006, Tsurushita et al., *Methods* 36:69-83, 2005, Roque et al., *Biotechnol. Frog.* 20:639-654, 2004.)

De-immunization involves altering potential linear T-cell epitopes present in the antibody. The epitopes can be identified based on a bioinformatics scan of know human HLA class I and/or class II epitopes. (See, for example, DeGroot and Moise, 2007, *Curr. Opin. Drug. Disc. Dev.* 10:332-340.)

A chimeric antibody is a monoclonal antibody constructed from variable regions derived from a different organism from the constant regions. For example, a chimeric antibody can contain variable regions from a murine source and constant regions derived from the intended host source (e.g., human; for a review, see Morrison and Oi 1989, *Advances in Immunology* 44: 65-92). To this end, the artisan may use known techniques to generate a chimeric antibody with the binding characteristics of a PD-1 binding protein disclosed herein. For example, the variable light and heavy genes from the rodent (e.g., mouse) antibody can be cloned into mammalian expression vectors which contain the appropriate human light chain and heavy chain constant domain coding regions, respectively. These heavy and light chain "chimeric" expression vectors are then cotransfected into a recipient cell line and subjected to known cell culture techniques, resulting in production of both the light and heavy chains of a chimeric antibody. Such chimeric antibodies have historically been shown to have the binding capacity of the original rodent monoclonal while significantly reducing immunogenicity problems upon host administration. Chimeric versions of one of the PD-1 binding protein disclosed herein, mAb 1B8, have shown the same affinity for human PD-1 as the murine counterpart (see Example 10, infra).

A "humanized antibody" further reduces the chance of a patient mounting an immune response against a therapeutic antibody when compared to use, for example, of a chimeric or fully murine monoclonal antibody. The strategy of "humanizing" involves sequence comparison between the non-human and human antibody variable domain sequences to determine whether specific amino acid substitutions from a non-human to human consensus is appropriate (Jones et al., 1986, *Nature* 321: 522-526). This technology is well known in the art and is represented by numerous strategies for its improvement, including but not limited to, "reshaping" (see Verhoeyen, et al., 1988, *Science* 239:1534-1536), "hyperchimerization" (see Queen, et al., 1991, *Proc. Natl. Acad. Sci.* 88:2869-2873), "CDR grafting" (Winter and Harris, 1993, *Immunol. Today* 14:243-246), "veneering" (Mark, et al., 1994, *Derivation of Therapeutically Active Humanized and Veneered anti-CD18 Antibodies*. In: Metcalf and Dalton, eds. *Cellular Adhesion: Molecular Definition to Therapeutic Potential*. New York: Plenum Press, 291-312), and "SDR grafting" (Kashmiri et al., 2005, *Methods* 36:25-34).

Fully human mAbs can be produced using genetically engineered mouse strains which possess an immune system whereby the mouse antibody genes have been inactivated and in turn replaced with a repertoire of functional human antibody genes, leaving other components of the mouse immune system unchanged. Such genetically engineered mice allow for the natural in vivo immune response and affinity maturation process, resulting in high affinity, fully human monoclonal antibodies. This technology is well known in the art and is fully detailed in various publications, including but not limited to U.S. Pat. Nos. 5,939,598; 6,075,181; 6,114,598; 6,150,584 and related family members; as well as U.S. Pat. Nos. 5,545,806; 5,569,825; 5,625,126; 5,633,425; 5,789,650; 5,877,397; 5,661,016; 5,814,318; 5,874,299; and 5,770,429. See also a review from Kellerman and Green, 2002, *Curr. Opinion in Biotechnology* 13: 593-597. Human antibodies can also be produced starting with a human phage display library.

Techniques such as affinity maturation can be used to further enhance the ability of a PD-1 binding protein to selectively bind to a target region. Affinity maturation can be performed, for example, by introducing mutations into a CDR region and determining the effect of the mutations on binding. Different techniques may be employed to introduce the mutations. (See, for example, Rajpal et al., *PNAS* 102: 8466-8471, 2005; Presta, *Advanced Drug Delivery Reviews* 58:640-656, 2006.)

Additional examples of alterations include providing a variable region in, for example, a single chain antibody, a diabody, a triabody, a tetrabody, and a miniantibody. The PD-1 binding protein can contain one or more variable regions recognizing the same or different epitopes. Additional embodiments are directed to a single chain antibody, a diabody, a triabody, a tetrabody, or a miniantibody directed to a PD-L1-blocking target region or a PD-L1-non-blocking target region.

II.C. Additional Components

PD-1 binding proteins may contain additional components including, but not limited to, components other than variable regions or additional variable regions that provide, or help provide, useful and/or additional activities. Useful activities include antibody effector functions such as antibody-dependent cellular cytoxicity, phagocytosis, complement-dependent cytoxicity, and half-life/clearance rate (see, e.g., Presta, *Advanced Drug Delivery Reviews* 58:640-656, 2006). Antibody effector functions are mediated by different host components, such as Fcγ receptors, neonatal Fc receptor (FcRn), and C1q (see Presta, 2006, supra; Satoh et al., *Expert Opin. Biol. Ther.* 6:1161-1173, 2006). Different types of antibody components or alterations can be used to enhance effector functions. Examples of useful components or alternations include the use of non-fucosylated oligosaccharides, amino acids with enhanced binding to FcRn, and amino acid alterations with enhanced binding to a Fcγ receptor (see Presta, 2006, supra; Satoh et al., 2006, supra; Lazar et al., U.S. Patent Application Publication US 2004/0132101; Shields et al., *The Journal of Biological Chemistry* 276:6591-6604, 2001; Dall'Acqua et al., *The Journal of Biological Chemistry* 281: 23514-23524, 2006).

In one embodiment of the present invention, a PD-1 binding protein which targets a PD-L1-blocking or PD-L1-non-blocking target region described herein is an anti-PD-1 antibody which, contains an Fc constant domain that is modified to minimize antibody dependent cell-mediated cytoxicity, Fc gamma receptor binding and/or complement-mediated cytoxicity. One such human antibody constant domain known as "IgG2 m4" is described in detail in U.S. Patent Publication no. US 2007/0148167, published in the name of W. R. Strohl; incorporated by reference herein. The IgG2m4 antibody backbone retains a substantial portion of an immunoglobulin G2 (IgG2) Fc region but contains amino acid substitutions derived from IgG4 at positions 268, 309, 330 and 331, according to the Kabat numbering system, wherein the amino acids residues at said positions are substituted with the corresponding amino acids from the human IgG4 Fc region. The Fc residues mutated in IgG2 include His268Gln, Val309Leu, Ala330Ser and Pro331Ser. These changes result in an overall reduction in Fc gamma receptor (FcγR) and complement (C1q) binding while maintaining normal serum half-life. Incorporation of the heavy chain variable domain from mAb 1B8 into the IgG2m4 backbone generates a chimeric 1B8 antibody (further containing a light chain having the mAb 1B8 light chain variable domain fused to the human kappa constant region) that binds to PD-1 with the same affinity as mAb 1B8 (see Example 10, infra).

In one embodiment of the present invention, a PD-1 binding protein targeting the PD-L1-blocking target region or the PD-L1-non-blocking, as described herein, is contained within a bispecific antibody (see, e.g., Marvin and Zhu, *Acta Pharmacologica Sinica* 26:649-658, 2005; Zuo et al., *Protein Engineering* 13:361-367, 2000; Ridgway et al., *Protein Engineering* 9:617-621, 1996; Alt et al., *FEBS Letters* 454:90-94, 1999; Carter, *J. Immunol. Methods* 248:7-15, 2001). In one embodiment of this portion of the present invention, said bispecific antibody contains an Fc or modified Fc domain that is capable of mediating antibody effector functions. Said bispecific antibodies can be bivalent, trivalent or tetravalent.

In another embodiment of the present invention, a PD-1 binding protein that binds the PD-L1-blocking target region or the PD-L1-non-blocking, as described herein, target region comprises additional components to alter the physiochemical properties of the protein, providing significant pharmacological advantages. For example, the attachment of polyethylene glycol ("PEG") to molecules may help to improve safety by reducing toxicity and increasing efficiency of said molecules when used as therapeutics. Physiochemical alterations include, but are not limited to, changes in conformation, electrostatic binding, and hydrophobicity which can work together to increase systemic retention of a therapeutic agent. Additionally, by increasing the molecular weight of a PD-1 binding protein by attaching a PEG moiety, pharmacological advantages include extended circulating life, increased stability, and enhanced protection from host proteases. PEG attachment can also influence binding affinity of the therapeutic moiety to cell receptors. PEG is a non-ionic polymer composed of repeating units ($-O-CH_2-CH_2-$) to make a range of molecular weight polymers from 400 to greater than 15,000 (e.g., PEG polymers with molecular weights of up to 400,000 are commercially available).

II.D. Examples of Different Embodiments

A PD-1 binding protein targeting a PD-L1-blocking target region or a PD-L1-non-blocking target region contains a first variable region and a second variable region, wherein the first and second variable regions bind to the target region. Thus, the present invention relates to an isolated PD-1 binding protein comprising a first variable region and a second variable region, wherein said binding protein specifically binds a human PD-1 epitope contained within a target region selected from the group consisting of a PD-L1-blocking target region and a PD-L1-non-blocking target region. Thus, in one embodiment, the PD-1 binding proteins of the present invention either block or attenuate the binding of one of its natural ligands, PD-L1. In another embodiment, the PD-1 binding proteins of the present invention do not inhibit binding of PD-L1 to PD-1.

Based on the guidance provided herein, PD-1 binding proteins targeting the respective target regions can be produced having different CDR and framework amino acids. Additional components such as a hinge region, Fc region, toxic moiety and/or additional PD-1 binding proteins (see Section II.C., supra) may be present.

In a first embodiment concerning a PD-1 binding protein of the present invention, said binding protein binds a PD-L1-blocking target region within PD-1.

In a second embodiment, the first variable region is a $V_h$ region comprising any one, two or all three of the following CDRs:

a first $V_h$ CDR comprising either SEQ ID NO:6, SEQ ID NO:14, SEQ ID NO:20, SEQ ID NO:28, SEQ ID NO:36, SEQ ID NO:42 or SEQ ID NO:49, or an amino acid sequence differing from SEQ ID NOs:6, 14, 20, 28, 36, 42 or 49 by one amino acid; preferably, the first $V_h$ CDR comprises either SEQ ID NOs:6, 14, 20, 28, 36, 42 or 49;

a second $V_h$ CDR comprising either SEQ ID NO:7, SEQ ID NO:15, SEQ ID NO:21, SEQ ID NO:29, SEQ ID NO:37, SEQ ID NO:43 or SEQ ID NO:50, or an amino acid sequence differing from SEQ ID NOs:7, 15, 21, 29, 37, 43 or 50 by one amino acid; preferably, the second $V_h$ CDR comprises either SEQ ID NOs:7, 15, 21, 29, 37, 43 or 50; and, a third $V_h$ CDR comprising either SEQ ID NO:8, SEQ ID NO:16, SEQ ID NO:22, SEQ ID NO:30, SEQ ID NO:38, SEQ ID NO:44 or SEQ ID NO:51, or an amino acid sequence differing from SEQ ID NOs:8, 16, 22, 30, 38, 44 or 51 by one amino acid; preferably, the third $V_h$ CDR comprises either SEQ ID NOs:8, 16, 22, 30, 38, 44 or 51.

In a third embodiment, the first variable region is a $V_h$ region comprising a first, a second and a third CDR which comprises amino acid sequences selected from the group consisting of:

(a) SEQ ID NO:6, SEQ ID NO:7 and SEQ ID NO:8, respectively;
(b) SEQ ID NO:14, SEQ ID NO:15 and SEQ ID NO:16, respectively;
(c) SEQ ID NO:20, SEQ ID NO:21 and SEQ ID NO:22, respectively;
(d) SEQ ID NO:42, SEQ ID NO:43 and SEQ ID NO:44, respectively;
(e) SEQ ID NO:49, SEQ ID NO:50 and SEQ ID NO:51, respectively;
(f) SEQ ID NO:28, SEQ ID NO:29 and SEQ ID NO:30, respectively; and,
(g) SEQ ID NO:36, SEQ ID NO:37 and SEQ ID NO:38, respectively.

In a sub-embodiment, one or more of the three CDRs within a particular $V_h$ region (i.e., as recited in (a) through (g)) comprises an amino acid sequence that differs from said CDR SEQ ID NO: by one amino acid.

In a fourth embodiment, the second variable region is a $V_l$ region comprising any one, two, or all three of the following CDRs:

a first $V_l$ CDR comprising either SEQ ID NO:9, SEQ ID NO:23, SEQ ID NO:31, SEQ ID NO:39, SEQ ID NO:45 or SEQ ID NO:52, or an amino acid sequence differing from SEQ ID NOs:9, 23, 31, 39, 45 or 52 by one amino acid; preferably, the first $V_l$ CDR comprises either SEQ ID NOs:9, 23, 31, 39, 45 or 52;

a second $V_l$ CDR comprising either SEQ ID NO:10, SEQ ID NO:17, SEQ ID NO:24, SEQ ID NO:32 or SEQ ID NO:53, or an amino acid sequence differing from SEQ ID NOs:10, 17, 24, 32 or 53 by one amino acid; preferably, the second $V_l$ CDR comprises SEQ ID NOs:10, 17, 24, 32 or 53; and, a third $V_l$ CDR comprising either SEQ ID NO:11, SEQ ID NO:25, SEQ ID NO:33, SEQ ID NO:46 or SEQ ID NO:54, or an amino acid sequence differing from SEQ ID NOs:11, 25, 33, 46 or 54 by one amino acid; preferably, the third $V_l$ CDR comprises SEQ ID NOs:11, 25, 33, 46 or 54.

In a fifth embodiment, the second variable region is a $V_l$ region comprising a first, a second and a third CDR which comprises amino acid sequences selected from the group consisting of:

(a) SEQ ID NO:9, SEQ ID NO:10 and SEQ ID NO:11, respectively;
(b) SEQ ID NO:9, SEQ ID NO:17 and SEQ ID NO:11, respectively;
(c) SEQ ID NO:23, SEQ ID NO:24 and SEQ ID NO:25, respectively;
(d) SEQ ID NO:45, SEQ ID NO:24 and SEQ ID NO:46, respectively;
(e) SEQ ID NO:52, SEQ ID NO:53 and SEQ ID NO:54, respectively;
(f) SEQ ID NO:31, SEQ ID NO:32 and SEQ ID NO:33, respectively; and,
(g) SEQ ID NO:39, SEQ ID NO:24 and SEQ ID NO:25, respectively.

In a sub-embodiment, one or more of the three CDRs within a particular $V_l$ region (i.e., as recited in (a) through (g)) comprises an amino acid sequence that differs from said CDR SEQ ID NO: by one amino acid.

In a sixth embodiment, the binding protein contains the $V_h$ region as described in the second or third embodiments and the $V_l$ region as described in the fourth or fifth embodiments. In sub-embodiments, the binding protein contains one of the following combinations: a $V_h$ region as described in the second embodiment and a $V_l$ region as described in the fourth embodiment; a $V_h$ region as described in the third embodiment and a $V_l$ region as described in the fourth embodiment; a $V_h$ region as described in the second embodiment and a $V_l$ region as described in the fifth embodiment; and, a $V_h$ region as described in the third embodiment and a $V_l$ region as described in the fifth embodiment.

In a seventh embodiment, the PD-1 binding protein which binds a PD-L1-blocking target region contains a $V_h$ region and a $V_l$ region, each comprising a first, a second and a third CDR, wherein said first, second and third $V_h$ CDRs and said first, second and third $V_l$ CDRs comprise amino acid sequences selected from the group consisting of:

(a) SEQ ID NO:6, SEQ ID NO:7, SEQ ID NO:8, SEQ ID NO:9, SEQ ID NO:10 and SEQ ID NO:11;
(b) SEQ ID NO:14, SEQ ID NO:15, SEQ ID NO:16, SEQ ID NO:9, SEQ ID NO:17 and SEQ ID NO:11;
(c) SEQ ID NO:20, SEQ ID NO:21, SEQ ID NO:22, SEQ ID NO:23, SEQ ID NO:24 and SEQ ID NO:25;
(d) SEQ ID NO:42, SEQ ID NO:43, SEQ ID NO:44, SEQ ID NO:45, SEQ ID NO:24 and SEQ ID NO:46;
(e) SEQ ID NO:42, SEQ ID NO:43, SEQ ID NO:44, SEQ ID NO:52, SEQ ID NO:53 and SEQ ID NO:54;
(f) SEQ ID NO:49, SEQ ID NO:50, SEQ ID NO:51, SEQ ID NO:45, SEQ ID NO:24 and SEQ ID NO:46;
(g) SEQ ID NO:49, SEQ ID NO:50, SEQ ID NO:51, SEQ ID NO:52, SEQ ID NO:53 and SEQ ID NO:54;
(h) SEQ ID NO:28, SEQ ID NO:29, SEQ ID NO:30, SEQ ID NO:31, SEQ ID NO:32 and SEQ ID NO:33;
(i) SEQ ID NO:36, SEQ ID NO:37, SEQ ID NO:38, SEQ ID NO:39, SEQ ID NO:24 and SEQ ID NO:25; and, wherein the order of the SEQ ID NOs correspond to $V_h$ CDR1, $V_h$ CDR2, $V_h$ CDR3, $V_l$ CDR1, $V_l$ CDR2 and $V_l$ CDR3.

In a sub-embodiment, one or more of the six CDRs as recited in (a) through (i) comprises an amino acid sequence that differs from said CDR SEQ ID NO: by one amino acid.

In an eighth embodiment concerning a PD-1 binding protein of the present invention, said PD-1 binding protein binds a PD-L1-non-blocking target region within PD-1.

In a ninth embodiment, the first variable region of said protein which binds a PD-L1-non-blocking target region is a $V_h$ region comprising any one, two or all three of the following CDRs:

a first $V_h$ CDR comprising either SEQ ID NO:57, SEQ ID NO:64 or SEQ ID NO:69, or an amino acid sequence differing from SEQ ID NOs:57, 64 or 69 by one amino acid; preferably, the first $V_h$ CDR comprises either SEQ ID NOs: 57, 64 or 69;

a second $V_h$ CDR comprising either SEQ ID NO:58, SEQ ID NO:65 or SEQ ID NO:70, or an amino acid sequence differing from SEQ ID NOs:58, 65 or 70 by one amino acid; preferably, the second $V_h$ CDR comprises either SEQ ID NOs:58, 65 or 70; and, a third $V_h$ CDR comprising either SEQ ID NO:59, SEQ ID NO:66 or SEQ ID NO:71, or an amino acid sequence differing from SEQ ID NOs:59, 66 or 71 by one amino acid; preferably, the third $V_h$ CDR comprises either SEQ ID NOs: 59, 66 or 71.

In a tenth embodiment, the first variable region is a $V_h$ region comprising a first, a second and a third CDR which comprises amino acid sequences selected from the group consisting of:

(a) SEQ ID NO:57, SEQ ID NO:58 and SEQ ID NO:59, respectively;

(b) SEQ ID NO:64, SEQ ID NO:65 and SEQ ID NO:66, respectively; and, (c) SEQ ID NO:69, SEQ ID NO:70 and SEQ ID NO:71, respectively.

In a sub-embodiment, one or more of the three CDRs within a particular $V_h$ region (i.e., as recited in (a) through (c)) comprises an amino acid sequence that differs from said CDR SEQ ID NO: by one amino acid.

In an eleventh embodiment, the second variable region is a $V_l$ region comprising any one, two, or all three of the following CDRs:

a first $V_l$ CDR comprising either SEQ ID NO: 60 or SEQ ID NO:72, or an amino acid sequence differing from SEQ ID NOs:60 or 72 by one amino acid; preferably, the first $V_l$ CDR comprises either SEQ ID NOs:60 or 72;

a second $V_l$ CDR comprising either SEQ ID NO:61 or SEQ ID NO:73, or an amino acid sequence differing from SEQ ID NOs:61 or 73 by one amino acid; preferably, the second $V_l$ CDR comprises either SEQ ID NOs:61 or 73; and, a third $V_l$ CDR comprising either SEQ ID NO:62 or SEQ ID NO:74, or an amino acid sequence differing from SEQ ID NOs:62 or 74 by one amino acid; preferably, the third $V_l$ CDR comprises either SEQ ID NOs:62 or 74.

In a twelfth embodiment, the second variable region is a $V_l$ region comprising a first, a second and a third CDR which comprises amino acid sequences selected from the group consisting of:

(a) SEQ ID NO:60, SEQ ID NO:61 and SEQ ID NO:62, respectively; and, (b) SEQ ID NO:72, SEQ ID NO:73 and SEQ ID NO:74, respectively.

In a sub-embodiment, one or more of the three CDRs within a particular $V_l$ region (i.e., as recited in (a) and (b)) comprises an amino acid sequence that differs from said CDR SEQ ID NO: by one amino acid.

In a thirteenth embodiment, the binding protein contains the $V_h$ region as described in the ninth or tenth embodiments and the $V_l$ region as described in the eleventh or twelfth embodiments. In sub-embodiments, the binding protein contains one of the following combinations: a $V_h$ region as described in the ninth embodiment and a $V_l$ region as described in the eleventh embodiment; a $V_h$ region as described in the tenth embodiment and a $V_l$ region as described in the eleventh embodiment; a $V_h$ region as described in the ninth embodiment and a $V_l$ region as described in the twelfth embodiment; and, a $V_h$ region as described in the tenth embodiment and a $V_l$ region as described in the twelfth embodiment.

In a fourteenth embodiment, the binding protein contains a $V_h$ region and a $V_l$ region, each comprising a first, a second and a third CDR, wherein said first, second and third $V_h$ CDRs and said first, second and third $V_l$ CDRs comprise amino acid sequences selected from the group consisting of (a) SEQ ID NO:57, SEQ ID NO:58, SEQ ID NO:59, SEQ ID NO:60, SEQ ID NO:61 and SEQ ID NO:62; and, (b) SEQ ID NO:69, SEQ ID NO:70, SEQ ID NO:71, SEQ ID NO:72, SEQ ID NO:73 and SEQ ID NO:74;

wherein the order of the SEQ ID NOs correspond to $V_h$ CDR1, $V_h$ CDR2, $V_h$ CDR3, $V_l$ CDR1, $V_l$ CDR2 and $V_l$ CDR3.

In a sub-embodiment, one or more of the six CDRs as recited in (a) and (b) comprises an amino acid sequence that differs from said CDR SEQ ID NO: by one amino acid.

In a fifteenth embodiment, the PD-1 binding protein is an antibody having one or more variable regions as described in the first through fourteen embodiments described above. In a sub-embodiment, the antibody is an IgG.

In a sixteenth embodiment, the variable region provided for in embodiments one to fifteen described above has a framework region with at least a 90% sequence identity to at least one of the mAbs 1B8, 20B3.1, 7G3, 3H4, 28.11, 1G7, 1.8A10, 6D10 and 2.3A9 light or heavy chain frameworks (see sequences disclosed in Example 4, infra). In further embodiments, the sequence identity is at least 95%, or at least 99%, identical to the framework of any one of the mAbs 1B8, 20B3.1, 7G3, 3H4, 28.11, 1G7, 1.8A10, 6D10 and 2.3A9; or differs from anyone of the mAb frameworks by 0, 1, 2, 3, 4, 5, 6, 7, 8, 9, 10, 11, 12, 13, 14, 15, 16, 17, 18, 19, or 20 amino acids. In a further embodiment, the variable region provided for in embodiments one to four above has human framework regions. Sequence identity (also referred to as percent identical) to a reference sequence is determined by aligning a sequence with the reference sequence and determining the number of identical amino acids in the corresponding regions. This number is divided by the total number of amino acids in the reference sequence and then multiplied by 100 and rounded to the nearest whole number.

In a seventeenth embodiment, a PD-1 binding protein of the present invention comprises a first variable region which is a $V_l$ region comprising an amino acid sequence selected from the group consisting of SEQ ID NO:4, SEQ ID NO:12, SEQ ID NO:18, SEQ ID NO:40, SEQ ID NO:47, SEQ ID NO:26 and SEQ ID NO:34, or a humanized version thereof. IN a sub-embodiment, said binding protein binds to a PD-L1-blocking target region.

In an eighteenth embodiment, a PD-1 binding protein of the present invention comprises a first variable region which is a $V_h$ region comprising an amino acid sequence selected from the group consisting of SEQ ID NO:55, SEQ ID NO:63 and SEQ ID NO:67, or a humanized version thereof. In a sub-embodiment, said binding protein binds to a PD-L1-non-blocking target region.

In a nineteenth embodiment, a PD-1 binding protein of the present invention comprises a second variable region which is a $V_l$ region comprising an amino acid sequence selected from the group consisting of SEQ ID NO:5, SEQ ID NO:13, SEQ ID NO:19, SEQ ID NO:41, SEQ ID NO:48, SEQ ID NO:27 and SEQ ID NO:35, or a humanized version thereof. In a sub-embodiment, said binding protein binds to a PD-L1-blocking target region.

In a twentieth embodiment, a PD-1 binding protein of the present invention comprises a second region which is a $V_l$ region comprising an amino acid sequence selected from the group consisting of SEQ ID NO:56 and SEQ ID NO:68, or a humanized version thereof. In a sub-embodiment, said binding protein binds to a PD-L1-non-blocking target region.

In a twenty-first embodiment, the binding protein contains a $V_h$ region as described in the seventeenth or eighteenth embodiment and a $V_l$ region as described in the nineteenth or twentieth embodiment, respectively. In sub-embodiments, the binding protein contains one of the following combinations: a $V_h$ region as described in the seventeenth embodiment and a $V_l$ region as described in the nineteenth embodiment; a $V_h$ region as described in the eighteenth embodiment and a $V_l$ region as described in the nineteenth embodiment; a $V_h$ region as described in the seventeenth embodiment and a $V_l$ region as described in the twentieth embodiment; and, a $V_h$ region as described in the eighteenth embodiment and a $V_l$ region as described in the twentieth embodiment. In another sub-embodiment, the binding protein is an antibody.

In a twenty-second embodiment, a PD-1 binding protein of the present invention that binds a PD-L1-blocking target region is an antibody containing either:
(a) a light chain variable region comprising SEQ ID NO:5 or a humanized SEQ ID NO:5, and a heavy chain variable region comprising SEQ ID NO: 4 or a humanized SEQ ID NO:4;
(b) a light chain variable region comprising SEQ ID NO:13 or a humanized SEQ ID NO:13, and a heavy chain variable region comprising SEQ ID NO:12 or a humanized SEQ ID NO:12;
(c) a light chain variable region comprising SEQ ID NO:19 or a humanized SEQ ID NO:19, and a heavy chain variable region comprising SEQ ID NO:18 or a humanized SEQ ID NO:18;
(d) a light chain variable region comprising SEQ ID NO:41 or a humanized SEQ ID NO:41, and a heavy chain variable region comprising SEQ ID NO:40 or a humanized SEQ ID NO:40;
(e) a light chain variable region comprising SEQ ID NO:41 or a humanized SEQ ID NO:41, and a heavy chain variable region comprising SEQ ID NO:47 or a humanized SEQ ID NO:47;
(f) a light chain variable region comprising SEQ ID NO:48 or a humanized SEQ ID NO:48, and a heavy chain variable region comprising SEQ ID NO: 40 or a humanized SEQ ID NO:40;
(g) a light chain variable region comprising SEQ ID NO:48 or a humanized SEQ ID NO:48, and a heavy chain variable region comprising SEQ ID NO:47 or a humanized SEQ ID NO:47;
(h) a light chain variable region comprising SEQ ID NO:27 or a humanized SEQ ID NO:27, and a heavy chain variable region comprising SEQ ID NO:26 or a humanized SEQ ID NO:26; or,
(i) a light chain variable region comprising SEQ ID NO:35 or a humanized SEQ ID NO:35, and a heavy chain variable region comprising SEQ ID NO:34 or a humanized SEQ ID NO:34.

In a sub-embodiment, one or both of the variable regions as recited in (a) through (i) comprises an amino acid sequence that differs from said variable region SEQ ID NO: by one amino acid.

In a twenty-third embodiment, a PD-1 binding protein of the present invention that binds a PD-L1-non-blocking target region is an antibody containing either:
(a) a light chain variable region comprising SEQ ID NO:56 or a humanized SEQ ID NO:56, and a heavy chain variable region comprising SEQ ID NO:55 or a humanized SEQ ID NO:55; or,
(b) a light chain variable region comprising SEQ ID NO:68 or a humanized SEQ ID NO:68, and a heavy chain variable region comprising SEQ ID NO:67 or a humanized SEQ ID NO:67.

In a sub-embodiment, one or both of the variable regions as recited in (a) and (b) comprises an amino acid sequence that differs from said variable region SEQ ID NO: by one amino acid.

In a twenty-fourth embodiment, the binding protein is an antibody described in embodiments fifteen to twenty-three above, comprising a heavy chain comprising a hinge, $CH_1$, $CH_2$, and $CH_3$ regions from an $IgG_1$, $IgG_2$, $IgG_3$ or $IgG_4$ subtype; and a light chain comprising either a human kappa $C_l$ or human lambda $C_l$.

In an twenty-fifth embodiment, the binding protein is an antibody as described in embodiments fifteen to twenty-four above containing one or more of the following: a glycosylation pattern that is either non-fucosylated or substantially (i.e., less than 10% on a molar basis of the carbohydrates that are present) non-fucosylated; one or more amino acid alterations that enhances Fcγ receptor binding; one or more amino acid alterations that enhances neonatal Fc receptor (FcRn) binding; and one or more amino acid alterations that enhances C1q binding.

In a twenty-sixth embodiment, the indicated region (e.g., variable region, CDR region, framework region) described in embodiments one to twenty-five above consists, or consists essentially, of an indicated sequence. Reference to "consists essentially" with respect to a region such as a variable region, CDR region, or framework region, indicates the possible presence of one or more additional amino acids at the amino and/or carboxyl termini, where such amino acids do not significantly decrease binding to the target.

In a twenty-seventh embodiment, the PD-1 binding protein described in embodiments one to twenty-six above has $V_h$ and $V_l$ regions providing an affinity $K_D$ of 50 nM or less, or a $K_D$ of 500 pM or less, to the target antigen. Binding to the target antigen can be determined as described in Example 5.

In a twenty-eighth embodiment, the PD-1 binding protein described in embodiments one to twenty-seven above is joined to at least one or more additional components, including but not limited to a toxic moiety, a molecule(s) to increase physiochemical and/or pharmacological properties of the PD-1 binding protein, and a second PD-1 binding protein (see Section II.C., supra). In a further embodiment, the PD-1 binding protein has one or more PEG moieties.

Amino acid differences described in the different embodiments, including those providing for differences in sequence identity, can be an amino acid deletion, insertion, or substitution. In substituting amino acids to maintain activity, the substituted amino acids should have one or more similar properties such as approximately the same charge, size, polarity and/or hydrophobicity. CDRs, while responsible for binding to a target, can be varied and still retain target specificity. Framework region sequences can also be varied. In an embodiment concerning amino acid differences, an additional variation is a conservative amino acid substitution. A conservative substitution replaces an amino acid with another amino acid having similar properties. Table 3 provides a list of groups of amino acids, where one member of the group is a conservative substitution for another member.

TABLE 3

| Conservative Amino Acid Substitutions |
|---|
| Ala, Val, Ile, Leu, Met |
| Ser, Thr |
| Tyr, Trp |
| Asn, Gln |
| Asp, Glu |
| Lys, Arg, His |

III. Protein Production

PD-1 binding proteins and regions thereof are preferably produced using recombinant nucleic acid techniques or through the use of a hybridoma. Different PD-1 binding proteins can be produced by different techniques, including, for example, a single chain protein containing a $V_h$ region and $V_l$ region connected by a linker sequence, such as a scFv, and antibodies or fragments thereof; and a multi-chain protein containing a $V_h$ and $V_l$ region on separate polypeptides. Recombinant nucleic acid techniques involve constructing a nucleic acid template for protein synthesis. Hybridoma techniques involve using an immortalized cell line to produce the PD-1 binding protein. Suitable recombinant nucleic acid and hybridoma techniques are well known in the art. (See, for example, Ausubel, *Current Protocols in Molecular Biology*, John Wiley, 2005; Harlow et al., *Antibodies, A Laboratory Manual*, Cold Spring Harbor Laboratory, 1988.)

III.A. Recombinant Nucleic Acids

Recombinant nucleic acid encoding a PD-1 binding protein can be expressed in a host cell that in effect serves as a factory for the encoded protein. The recombinant nucleic acid can provide a recombinant gene encoding the PD-1 binding protein that exists autonomously from a host cell genome or as part of the host cell genome.

A recombinant gene contains nucleic acid encoding a protein along with regulatory elements for protein expression. Generally, the regulatory elements that are present in a recombinant gene include a transcriptional promoter, a ribosome binding site, a terminator, and an optionally present operator. A promoter is defined as a DNA sequence that directs RNA polymerase to bind to DNA and initiate RNA synthesis. A strong promoter is one which causes mRNAs to be initiated at high frequency. A preferred element for processing in eukaryotic cells is a polyadenylation signal. Antibody associated introns may also be present. Examples of expression cassettes for antibody or antibody fragment production are well known in art. (E.g., Persic et al., 1997, *Gene* 187:9-18; Boel et al., 2000, *J Immunol. Methods* 239:153-166; Liang et al., 2001, *J. Immunol. Methods* 247:119-130; Tsurushita et al., 2005, *Methods* 36:69-83.)

The degeneracy of the genetic code is such that, for all but two amino acids, more than a single codon encodes a particular amino acid. This allows for the construction of synthetic DNA that encodes a protein where the nucleotide sequence of the synthetic DNA differs significantly from the nucleotide sequences disclosed herein, but still encodes such a protein. Such synthetic DNAs are intended to be within the scope of the present invention.

If it is desired to express DNAs in a particular host cell or organism, the codon usage of such DNAs can be adjusted to maximize expression of a protein. One approach is to choose codons that reflect the codon usage of that particular host. Alternative codons which code for the identical amino acid are shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU Expression of a recombinant gene in a cell is facilitated using an expression vector. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. Preferably, the expression vector, in addition to a recombinant gene, also contains an origin of replication for autonomous replication in a host cell, a selectable marker, a limited number of useful restriction enzyme sites, and a potential for high copy number.

Examples of expression vectors for antibody and antibody fragment production are well known in art (e.g., Persic et al., 1997, *Gene* 187:9-18; Boel et al., 2000, *J. Immunol. Methods* 239:153-166; Liang et al., 2001, *J. Immunol. Methods* 247:119-130; Tsurushita et al., 2005, *Methods* 36:69-83). Expression vectors may include, but are not limited to, cloning vectors, modified cloning vectors, specifically designed plasmids or viruses. Such expression vectors, including mammalian, bacterial, fungal (e.g., *Pichia*), and insect cell expression vectors, are commercially available.

If desired, nucleic acid encoding an antibody may be integrated into the host chromosome using techniques well known in the art. (E.g., Ausubel, *Current Protocols in Molecular Biology*, John Wiley, 2005; Marks et al., International Application Number WO 95/17516, International Publication Date Jun. 29, 1995.)

A nucleic acid comprising one or more recombinant genes encoding for either or both of a PD-1 binding protein $V_h$ region or $V_l$ region can be used to produce a complete binding protein binding to an identified target region or a component of the binding protein. A complete binding protein can be provided, for example, using a single gene to encode a single chain protein containing a $V_h$ region and $V_l$ region, such as a scFv, or using multiple recombinant regions to, for example, produce both $V_h$ and $V_l$ regions. A region of a binding protein can be produced, for example, by producing a polypeptide containing the $V_h$ region or $V_l$ region in separate cells.

In different embodiments, one or more recombinant genes encode the PD-1 binding protein, or a $V_h$ region or $V_l$ region, as described in Section II.D supra. Preferably, the recombinant gene(s) are expressed in a single-host cell to produce the PD-1 binding protein. The protein can be purified from the cell.

III.B. Recombinant Nucleic Acid Expression

A variety of different cell lines can be used for recombinant PD-1 binding protein expression, including those from prokaryotic organisms (e.g., *E. coli, Bacillus* sp, and *Streptomyces* sp. (or streptomycete)) and from eukaryotic organisms (e.g., yeast, Baculovirus, and mammalian, including but not limited to cell lines of bovine, porcine, monkey and rodent origin) (see, e.g., Breitling et al., *Recombinant Antibodies*, John Wiley & Sons, Inc. and Spektrum Akademischer Verlag, 1999; Kipriyanov et al., 2004, *Molecular Biotechnology* 26:39-60; Tsurushita et al., 2005, *Methods* 36:69-83). Such cell lines are commercially available.

Preferred hosts for recombinant PD-1 binding protein expression provide for mammalian post translational modifications. Post translational modifications include chemical modification such as glycosylation and disulfide bond formation. Another type of post translational modification is signal peptide cleavage.

Glycosylation can be important for some antibody effector functions. (Yoo et al., 2002, *Journal of Immunological Methods* 261:1-20; Presta, 2006, *Advanced Drug Delivery Reviews* 58:640-656; Satoh et al., 2006, *Expert Opin. Biol. Ther.* 6:1161-1173.) Mammalian host cells can be modified, for example, to effect glycosylation. (Yoo et al., 2002, supra; Persic et al., 1997, *Gene* 187:9-18; Presta, 2006, supra; Satoh et al., 2006, supra.) Non-mammalian cells can also be modified to provide for a desired glycosylation. Glycoengineered *Pichia pastoris* is an example of such a modified non-mammalian cell. (Li et al., 2006, *Nature Biotechnology* 24(2):210-215.)

IV. Treatment with PD-1 Binding Proteins

Therapeutic and prophylactic treatment can be performed on a subject, preferably a human patient, by administering a PD-1 binding protein that binds to an appropriate PD-1 target region. Whether therapeutic or prophylactic treatment using the described PD-1 binding proteins is more appropriate will depend largely on the nature of the disease.

Administration of the PD-1 binding protein, alone or in combination with additional substances, can take the form of a composition that includes a pharmaceutically active carrier. The PD-1 binding proteins as described herein may be used under circumstances where an enhanced or augmented immune response, particularly an enhanced T cell response, is desired via attenuating the inhibitory signaling mediated by PD-1. A downregulation of PD-1 activity is especially desirable to treat microbial infections (e.g., bacteria, fungi, viruses) and cancer. As demonstrated in the Examples, a blockade of PD-1/PD-L1 interaction using a PD-1 binding protein as described herein leads to enhanced T cell responses, consistent with a downregulatory role in the PD-1 pathway (see Example 8, infra). Thus, the present invention includes methods of enhancing the cellular immune response in a subject, preferably a human subject, comprising administering a PD-1 binding protein, or pharmaceutical composition thereof, as described herein. Said enhancement of cellular immunity is a result of therapeutic and/or prophylactic treatment comprising administering a PD-1 binding protein of the present invention.

In one embodiment of the present invention, the PD-1 binding proteins described herein are used as part of a prophylactic treatment method. This embodiment includes the use of a PD-1 binding protein as an adjuvant in a vaccination regime to immunize a subject, preferably a human subject, against a specific disease, including but not limited to a microbial infection or cancer. The vaccination regimen can be used on the general population or a subset of the general population. A subset of the general population is persons at an increased risk of developing a microbial infection or cancer.

A composition which comprises a vaccine (either a prophylactic or therapeutic vaccine, described further infra) and a PD-1 binding protein of the present invention may be administered with either a single administration or within the confines of a prime/boost-type vaccine regimen. Preferably, the vaccine priming and boosting administrations are different in order to evade any host immunity directed against the first delivered vaccine, especially if that vaccine is delivered as part of a 'non-self' recombinant vehicle, such as a recombinant non-viral (e.g., plasmid) or viral (e.g., adenovirus, AAV, etc.) vehicle. Thus, the present invention is further drawn to compositions comprising one or more PD-1 binding proteins described herein in combination with one or more vaccines for prophylactic immunization and/or therapeutic treatment of a subject and the administration of such a vaccine composition to a subject. Alternatively, the PD-1 binding protein and the vaccine can be separately formulated and either co-administered or administered at different time points.

As shown in Example 8 (infra), administration of mAb 1B8 in combination with an adenovirus-based vaccine vector at time of priming enhanced T cell responses in naïve rhesus macaques. The enhanced T cell response can be correlated to inhibition of PD-1 signaling by mAb 1B8. Thus, one embodiment of the present invention includes methods of treating a subject, preferably a human subject, against a microbial infection by administering a therapeutically effective amount of a composition comprising a PD-1 binding protein described herein, including but not limited to mAb 1B8 or a humanized version thereof, and an adenoviral-based vaccine vector. In another aspect of this embodiment, the PD-1 binding protein and the adenoviral-based vaccine vector, or compositions thereof, are co-administered to the subject in separate formulations, rather than being combined within a single composition. The individual PD-1 binding protein(s) and adenoviral-based vaccine vector, or compositions thereof, can also be administered at different times points.

A PD-1 binding protein of the present invention may also be used as a therapeutic agent to enhance the cellular immune response of a patient. The PD-1 binding protein can be administered alone or in combination with additional therapeutic agents. Thus, the present invention is further drawn to compositions comprising one or more PD-1 binding proteins described herein in combination with additional therapeutic agents (e.g., therapeutic vaccine, anti-microbial agents, chemotherapeutic substances). When administered in combination with additional therapeutic agents, each component (i.e., the PD-1 binding protein and the additional therapeutic agent) can be present within a single composition and administered in a single dose. Alternatively, each component can be separately formulated and either administered to the subject contemporaneously or at different time points.

One embodiment of the present invention relates to methods of treating a patient with a microbial infection comprising the step of administering to the patient an effective amount of a PD-1 binding protein as described herein or a composition thereof. The PD-1 binding protein can be administered alone or in combination with additional anti-microbial substances. Administration of a PD-1 binding protein as described herein can be part of a therapeutic regime to treat patients already infected with a microbial pathogen (therapeutic treatment). Alternatively, as described supra, a PD-1 binding protein can be used as part of prophylactic method to help protect an individual against becoming infected (i.e., a vaccination based method). In this case, as described supra, the PD-1 binding protein is used as an adjuvant.

As an example to illustrate this portion of the present invention, when used as part of a therapeutic regime to treat persons infected with human immunodeficiency virus (HIV), an PD-1 binding protein as described herein can be administered to an individual either alone or in combination with other anti-HIV therapies (e.g., anti-retroviral compounds). Classes of anti-retrovirals that could be used in conjunction with the disclosed PD-1 binding proteins include, but are not limited to, nucleoside reverse transcriptase inhibitors (NR-TIs), non-nucleoside reverse transcriptase inhibitors (NNR-TIs), protease inhibitors (PIs), and integrase inhibitors. The anti-viral agent may be administered to the individual in some combination of effective anti-viral therapeutics such as that present in highly active anti-retroviral therapy ("HAART"). Administration of a PD-1 binding protein, alone or in combination with additional anti-retroviral agents, will result in a reduction in existing viral load and thus prolong the asymptomatic phase of the disease. Such a response may by documented by in vitro assays, in vivo non-human animal studies and/or further supported from human clinical trials.

A similar treatment regime comprising administration of a PD-1 binding protein as described herein can be used to treat a subject, either alone or in combination with other therapeutic agents, for any microbial infection. As a further example of this portion of the present invention, PD-1 binding proteins can be used to treat subjects infected with hepatitis C virus (HCV), alone or in combination with additional anti-HCV agents. Additional agents for treatment of HCV infection that may be included in a composition with a PD-1 binding protein described herein are well known in the art and include, but are not limited to, ribavirin, levovirin, viramidine, thymosin alpha-1, interferon-α, pegylated interferon-α (peginterferon-α), a combination of interferon-α and ribavirin, a combination of peginterferon-α and ribavirin, a combination of interferon-α and levovirin, a combination of peginterferon-α and levovirin, and LY570310 (VX-950).

Microbial infections that can be treated by administering a PD-1 binding protein of the present invention generally take the form of a persistent infection. Acute infections are generally resolved from the body by the immune system relatively quickly, while persistent infections may last for months, years, or even a lifetime. Thus, persistent infections are the result of an infectious microbial agent (e.g., virus, bacterium, parasite, mycoplasm, fungus) that is not effectively cleared or eliminated from the host even after the induction of an immune response. Persistent infections may be chronic infections and/or latent infections. These infections may recur, involving stages of silent and productive infection without cell killing or even producing excessive damage to host cells.

Mammals are diagnosed as having a persistent microbial infection according to any standard method known in the art and described, for example, in the following: Shamanin et al., U.S. Pat. No. 6,368,832; Mitchell et al., U.S. Pat. No. 6,579,854; and Rao et al., U.S. Pat. Application Publication No. 2003/0064380. For example, a subject may be diagnosed as having a persistent Chlamydial infection following the detection of Chlamydial species in a biological sample from the individual using PCR analysis. However, subjects do not need to have been diagnosed with a persistent infection to be treated according to this invention. Microbial agents capable of establishing a persistent infection include viruses (e.g., papilloma virus, hepatitis virus, human immune deficiency virus, and herpes virus), bacteria (e.g., *Eschericchia coli* and *Chlamydia* spp.), parasites (e.g., *Plasmodium, Leishmania* spp., *Schistosoma* spp., *Trypanosoma* spp., *Toxoplasma* spp. and *Encephalitozoon*) and fungi.

In a chronic microbial infection, while the infectious agent can be detected in the body at all times, the signs and symptoms of the disease may be present or absent for an extended period of time. Chronic infections usually develop slowly and persist a long time. Examples of chronic infection include hepatitis B (caused by HBV) and hepatitis C (caused by HCV), adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B 19, polyomavirus BK, polyomavirus JC, measles virus, rubella virus, human immunodeficiency virus (HIV), human T cell leukemia virus I and human T cell leukemia virus II.

In a latent microbial infection, the infectious agent (e.g., virus) can appear inactive and dormant such that the subject does not always exhibit signs or disease symptoms. In a latent viral infection, the virus remains in equilibrium with the host for long periods of time before symptoms reappear; however, the actual viruses cannot be detected until reactivation of the disease occurs. Examples of latent infections include infections caused by HSV-1 (fever blisters), HSV-2 (genital herpes) and VZV (chickenpox-shingles).

Persistent microbial infections can often arise as late complications of acute infections. For example, subacute sclerosing panencephalitis (SSPE) can occur following an acute measles infection or regressive encephalitis can occur as a result of a rubella infection.

In another embodiment of the present invention, the PD-1 binding proteins described herein that bind to PD-1 are used as either part of a therapeutic regime to treat a subject, preferably a human subject, suffering from cancer or part of a prophylactic region to be administered to individuals susceptible to developing cancer. Said methods comprise the step of administering to the patient or individual an effective amount of a PD-1 binding protein, or composition thereof. The PD-1 binding protein can be administered alone as a monotherapy or in combination with additional anti-cancer substances. For example, a PD-1 binding protein described herein can be combined with an anti-cancer vaccine to act as an adjuvant in either a prophylactic or therapeutic regime using methods similar to that described above for microbial infections. Thus, in one embodiment, the invention provides a method of inhibiting growth of tumor cells in a subject, preferably a human subject, comprising administering to the subject a therapeutically effective amount of a PD-1 binding protein described herein.

Cancer treatment and/or prevention methods include the treatment and/or prevention of one or more common types of cancers diagnosed with high frequency (e.g., breast, colon and rectal, lung, prostate, and skin), especially those typically responsive to immunotherapy. Thus, methods of blocking the inhibitory signal from PD-1 by administering a PD-1 binding protein described herein for the treatment of one or more cancers is included as part of the present invention (e.g., ovarian cancer; cancers of non-lymphoid parenchymal organs including the heart, placenta, skeletal muscle and lung; breast cancer; cancers of the head and neck including various lymphomas, such as mantle cell lymphoma, non-Hodgkins B cell lymphoma, PTCL, adenoma, squamous cell carcinoma, laryngeal carcinoma, salivary carcinoma, thymomas and thymic carcinoma; leukemia; cancers of the retina; cancers of the esophagus; multiple myeloma; melanoma; colorectal cancer; lung cancer; cervical cancer; endometrium carcinoma; gallbladder cancer; liver cancer; thyroid follicular cancer; gastric cancer; non-small cell lung carcinoma; glioma; urotheial cancer; bladder cancer; prostate cancer; renal cell cancer; infiltrating ductal carcinoma; and glioblastoma multiform).

Optionally, a PD-1 binding protein of the present invention can be combined with an immunogenic agent, such as cancerous cells, purified tumor antigens (including recombinant proteins, peptides and carbohydrate molecules), and cells transfected with genes encoding immune stimulating cytokines (He et al., 2004, *J. Immunol.* 173:4919-4928).

Many experimental strategies for vaccination against tumors have been devised (see, e.g., Armstrong et al., 2001, *British J of Radiology* 74:991-1002; Sinkovics and Horvath, 2000, *Int. J. of Oncology* 16:81-96; DeVita, V. et al., eds., 2001, *Cancer: Principles and Practice of Oncology. Sixth Edition*. Philadelphia: Lippincott Williams & Wilkins). In one of these strategies, a vaccine is prepared using autologous or allogeneic tumor cells. Alternatively, an anti-cancer vaccine can take the form of a tumor specific antigen. The study of gene expression and large scale gene expression patterns in various tumors has led to the definition of so-called tumor specific antigens (Rosenberg, 1999, *Immunity* 10:281-287). In many cases, these tumor specific antigens are differentiation antigens expressed in the tumors and in the cell from which the tumor arose. These proteins are normally viewed by the immune system as self antigens and are therefore tolerant to them. Tumor antigens may also be "neo-antigens" expressed in cancer cells because of somatic mutations that alter protein sequence or create fusion proteins between two unrelated sequences or idiotype from B cell tumors. Another form of tumor specific antigen which may be used in conjunction with the PD-1 binding proteins of the present invention is purified heat shock proteins (HSP) isolated from the tumor tissue itself. These heat shock proteins contain fragments of proteins from the tumor cells and are highly efficient at delivery to antigen presenting cells for eliciting tumor immunity (Suot and Srivastava, 1995, *Science* 269:1585-1588; Tamura, et al., 1997, *Science* 278:117-120). Other tumor vaccines may include the proteins from viruses implicated in human cancers such a human papilloma viruses (HPV), hepatitis viruses (HBV and HCV) and Kaposi's herpes sarcoma virus (KHSV).

PD-1 binding proteins of the present invention may also be combined with standard cancer treatments. For example, administration of the PD-1 binding proteins may be effectively combined with chemotherapeutic regimes. In these instances, it may be possible to reduce the dose of chemotherapeutic reagent administered. The scientific rationale behind the combined use of the PD-1 binding proteins and chemotherapy is that cell death resulting from cytotoxic action of most chemotherapeutic compounds should result in increased levels of tumor antigen in the antigen presentation pathway. Other combination therapies that may be effective when combined with the PD-L1 inhibitory signal are radiation, surgery, and hormone deprivation. Each of these protocols creates a source of tumor antigen in the host. Angiogenesis inhibitors may also be combined with PD-L1 blockade. Inhibition of angiogenesis leads to tumor cell death which may feed tumor antigen into host antigen presentation pathways.

Reference to a substance having "anti-cancer" activity or an "anti-cancer substance" indicates a substance that inhibits the proliferation of cancerous cells, including substances that inhibit the growth of tumors. Substances that display anti-cancer activity include, without limitation, substances having cytotoxic chemotherapeutic effects and anti-cancer vaccines.

Chemotherapeutic drugs can be divided into alkylating agents, anti-metabolites, plant alkaloids, topoisomerase inhibitors, and antitumor agents. All of these drugs affect cell division or DNA synthesis or function in some way.

Alkylating agents are so named because of their ability to add alkyl groups to many electronegative groups under conditions present in cells. They stop tumor growth by cross-linking guanine nucleobases in DNA double-helix strands. Examples include cisplatin, carboplatin, ifosfamide, chlorambucil, busulfan and thiotepa.

Anti-metabolites mimic purine or pyrimidine and prevent these substances from becoming incorporated in to DNA during replication. Examples include 5-fluorouracil (5FU), which inhibits thymidylate synthase; fludarabine, which inhibits function of multiple DNA polymerases, DNA primase and DNA ligase I; and methotrexate, which inhibits dihydrofolate reductase, an enzyme essential for purine and pyrimidine synthesis.

Plant alkaloids block cell division by preventing microtubule function. Microtubules are vital for cell division and without them it can not occur. The main examples are vinca alkaloids and taxanes Vinca alkaloids bind to specific sites on tubulin, inhibiting the assembly of tubulin into microtubules. They are derived from the Madagascar periwinkle, *Catharanthus roseus* (formerly known as *Vinca rosea*). Taxanes are derived from the Pacific yew tree, *Taxus brevifolia*. Taxanes enhance stability of microtubules, preventing the separation of chromosomes during anaphase.

Topoisomerases are essential enzymes that maintain the topology of DNA. Inhibition of type I or type H topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. The latter are semisynthetic derivatives of epipodophyllotoxins, alkaloids naturally occurring in the root of mayapple (*Podophyllum peltatum*).

There are many differing anti-tumor antibiotics, but generally they prevent cell division by several ways: (1) binding to DNA through intercalation between two adjacent nucleotide bases and making it unable to separate, (2) inhibiting ribonucleic acid (RNA), preventing enzyme synthesis, and/or (3) interfering with cell replication. Anti-tumor antibiotics include various strains of the soil fungus *Streptomyces*, such as anthracyclines (doxorubicin, daunorubicin and epirubicin, which also inhibit topoisomerase II), actinomycin, bleomycin, mitomycin and plicamycin. Bleomycin acts through oxidation of a DNA-bleomycin-Fe(II) complex and forming free radicals, which induce damage and chromosomal aberrations.

The immune response is controlled by numerous soluble factors and immune response mediators such as tumour necrosis factor (TNF) alpha, interferon (IFN) gamma and numerous interleukins. Measuring cell functions via the measurement of the soluble immune factors (cytokines) at the level of individual cells can predict lymphocyte proliferation and differentiation, as well as final effector functions, e.g., cell-mediated cytotoxicity as measured in the $^{51}$Cr release assay. Historical T cell assays, designed for measuring helper and cytotoxic T cell activities, are the $^3$H thymidine incorporation assay for T cell proliferation and $^{51}$Cr release assay for cytotoxicity. In modern best practice, these assays are supplemented, or in some cases, replaced with assays with better quantification and higher throughput. For a recent review, see D. Nagorsen et al., Immunological monitoring of cancer vaccine therapy, *Expert Opin. Biol. Ther.,* 4(10):1677-1684, 2004. Examples include the ELISpot assay for detecting cytokine secretion (typically IFN-gamma), the intracellular cytokine staining assay, and the tetramer staining assay.

The ELISpot technique can measure individual soluble factors such as IFN-gamma, IL-4, IL-10 and TNF-alpha that are secreted by T-cells. The ELISpot technique typically utilizes 96-well microtiter plates coated with a monoclonal antibody to the specific soluble factor being measured (IFN-gamma, IL-4, etc.) where it functions as a capture antibody. The lymphoid cell population being investigated is then added to the microtiter wells containing the captured antibodies in a limiting dilution pattern. The specific antigen is also added to the wells and the cells are cultured for 12 to 24 hours. The cells and antigen are then washed from the well and replaced with a second enzyme-labeled monoclonal antibody specific to the soluble factor being measured. By developing the microtiter plate with the appropriate chromogen, a spot will appear in the bottom of the microliter well at each location where a cell was present in the primary culture that secreted the soluble factor being assayed. Since the number of cells originally added to the microtiter well is known, it is possible to quantify the number of cells responding to the antigen stimuli in the cell population being studied.

Intracellular staining of cytokine using flow cytometry (ICS) is similar to ELISpot in that it allows one to measure number of T cells producing specific cytokines in response to a particular antigen stimulus. In addition, ICS can identify the phenotype, e.g., CD4 and CD8, of the cytokine-producing stimulated cell. Tetramers are tetravalent complexes composed of single synthetic peptides, recombinantly expressed MHC complexes and beta-2 microglobulin. Tetramers mimic MHC/T cell epitope peptide complexes on antigen presenting cells, which are recognized by T cell receptors on lymphocytes. Fluorescently-labeled tetramers efficiently bind to T cells that have the specific TCR, and binding events can be detected and counted by flow cytometry. Thus, tetramer staining can be used to directly quantify the frequency of T cell epitope-specific T cells.

PD-1 binding proteins, and compositions thereof, may be administered to the host subject using one or more of the following routes: intravenous (IV), intramuscular (IM), and subcutaneous (SC), with IV administration being the norm within the art of therapeutic antibody administration (see, e.g., Middaugh et al., 1999, *Handbook of Experimental Pharmacology* 137:33-58). These compositions may be utilized in a regimen which may include a monovalent or multivalent composition and various combined modality applications. Therefore, these formulations may be administered as separate or multiple doses (i.e., administration of the PD-1 binding protein at staggered times by maintaining the sterile condition of the formulation through the treatment regime). Guidelines for pharmaceutical administration in general are provided in, for example, *Remington's Pharmaceutical Sciences* 20$^{th}$ Edition, Ed. Gennaro, Mack Publishing, 2000; and *Modern Pharmaceutics* 2$^{nd}$ Edition, Eds. Banker and Rhodes, Marcel Dekker, Inc., 1990.

The dosage regimen utilizing the PD-1 binding proteins of the present invention is selected in accordance with a variety of factors including type, species, age, weight, sex and medical condition of the patient; the severity of the condition to be treated; the route of administration; the renal, hepatic and cardiovascular function of the patient; and the particular PD-1 binding protein thereof employed. The dosing frequency can vary depending upon the effectiveness and stability of the compound. Examples of dosing frequencies include daily, biweekly, weekly, monthly and bimonthly. A physician or veterinarian of ordinary skill can readily determine and prescribe the effective therapeutic and/or prophylactic amount of the PD-1 binding protein. Optimal precision in achieving concentrations of PD-1 binding proteins within the range that yields efficacy without toxicity requires a regimen based on the kinetics of the protein's availability to target sites. This involves a consideration of the distribution, equilibrium, and elimination of a drug. It is expected that an effective dose range should be about 0.1 mg/kg to 20 mg/kg, or 0.5 mg/kg to 5 mg/kg.

The PD-1 binding proteins described herein may be used alone at appropriate dosages. Alternatively, co-administration or sequential administration of other agents may be desirable. In accordance with this portion of the present invention, the individual components of a combination treatment regime can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the PD-1 binding proteins of this invention with other agents includes in principle any combination with any pharmaceutical composition for treatment of a specific disease state, including but not limited to microbial infections and cancer. When a PD-1 binding protein described herein is used in combination with an additional therapeutic agent, the dose of each component may be either the same as or different from the dose when the component is used alone.

A "patient" or "subject" refers to a mammal in need of treatment against a particular disease state. Preferably, the patient or subject is a human. The PD-1 binding proteins of the present invention can be optimized in consideration of the subject to which it will be administered (e.g., humanized when used in methods involving human patients).

A pharmaceutically acceptable composition suitable for patient administration will contain an effective amount of the PD-1 binding protein in a formulation which both retains biological activity while also promoting increased stability during storage within an acceptable temperature range. Substances used to stabilize protein solution formulations include carbohydrates, amino acids, and buffering salts (see, e.g., Middaugh et al., 1999, *Handbook of Experimental Pharmacology* 137:33-58). The PD-1 binding protein-based pharmaceutical composition of the present invention may be formulated by any number of strategies known in the art (e.g., see McGoff and Scher, 2000, *Solution Formulation of Proteins/Peptides*: In—McNally, E. J., ed. *Protein Formulation and Delivery*. New York, N.Y.: Marcel Dekker; pp. 139-158; Akers and Defilippis, 2000, *Peptides and Proteins as Parenteral Solutions*. In—*Pharmaceutical Formulation Development of Peptides and Proteins*. Philadelphia, Pa.: Talyor and Francis; pp. 145-177; Akers, et al., 2002, *Pharm. Biotechnol.* 14:47-127).

Pharmaceutically acceptable carriers facilitate storage or administration of a PD-1 binding protein. Thus, a PD-1 binding protein-based pharmaceutical composition may optionally comprise a pharmaceutically acceptable carrier.

Examples of such carriers are well known in the art and are described in a variety of texts, such as Remington's Pharmaceutical Sciences. The protein formulation may be in liquid form or solid form. A solid formulation is generally lyophilized and brought into solution prior to administration for either single or multiple dosing. To date, both liquid and solid formulations require storage at lower temperatures (usually 2-8° C.) in order to retain stability for longer periods. Formulated protein compositions, especially liquid formulations, may contain a bacteriostat to prevent or minimize proteolysis during storage, including but not limited to effective concentrations (usually $\leq 1\%$ w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component.

V. Other Applications of PD-1 Binding Proteins

PD-1 binding proteins recognizing an appropriate epitope can have non-therapeutic applications. Non-therapeutic applications include using a PD-1 binding protein recognizing a PD-1 target region to facilitate the production, characterization, and/or study of PD-1 proteins and vaccines. For example, PD-1 binding proteins that both bind PD-1 and block PD-L1 (e.g., a PD-1 antagonist antibody) can be used to identify an epitope within PD-1 that has the ability to generate PD-1 antagonist antibodies when used to immunize a patient. Antigens containing an epitope that can specifically generate PD-1 antagonist antibodies may be useful to treat illness which would benefit from regulating T cell responses by blocking PD-1 mediated negative signals (e.g., cancer, persistent microbial infections). Techniques for using PD-1 binding proteins, such as monoclonal antibodies, in the production, characterization, or study of a target protein are well known in the art (see, for example, Ausubel, *Current Protocols in Molecular Biology*, John Wiley, 2005; Harlow et al., *Antibodies, A Laboratory Manual*, Cold Spring Harbor Laboratory, 1988; Harlow et al., *Using Antibodies*, Cold Spring Harbor Laboratory, Cold Spring Harbor, N.Y., Cold Spring Harbor Laboratory Press, 1999; and Lipman et al., 2005, *ILAR Journal* 46:258-268).

The PD-1 binding proteins as described herein can be used for isolating and/or detecting PD-1 or cells expressing PD-1 in biological samples. For example, the amount of PD-1 detected may be correlated with the expression level of PD-1. Expression of PD-1 can be correlated with the activation status of immune cells in the subject. Thus, in an embodiment of the present invention, the presence of a PD-1 antigen in a solution, bound to a microsphere or on a cell, is determined using a PD-1 binding protein. The ability of the binding protein to bind to a protein present in the solution or cell can be determined using different techniques such as a Western blot, enzyme-linked immunosorbent assay (ELISA), flow cytometry, Luminex immunoassay, immunofluorescence, immunoprecipitation. The PD-1 binding proteins may be provided in a diagnostic kit that incorporates one or more of these techniques to detect PD-1. Such a kit may contain other components to aid in the detection of the protein. Wherein the antibodies are intended for diagnostic purposes, it may be desirable to modify them, for example, with a ligand group (e.g., biotin) or a detectable marker group (e.g., fluorescent group, radioisotope, enzyme).

PD-1 binding proteins of the invention can be used in screening and selection methods to identify inhibitors of the PD-1 pathway that may be effective as therapeutic agents. Such a methodology comprises utilizing a PD-1 binding protein (e.g., an antibody) and a PD-1 protein or peptide fragment thereof in various PD-1 binding protein/peptide/test compound interaction assays. The compound may be a peptide (e.g., as a potential prophylactic or therapeutic peptide vaccine, as described supra), a protein, or a non-proteinaceous organic or inorganic molecule. A compound identified by this methodology by nature will be a compound that actively competes with the PD-1 binding proteins described herein for binding PD-1. To this end, interaction assays may be utilized for the purpose of high throughput screening to identify compounds that bind PD-1, and optionally block PD-L1 from binding PD-1, and displace the PD-1 binding protein. Various antibody/target protein based assays known in the art may be used which incorporate and rely on an anti-PD-1 antibody of the present invention as an essential reagent in screening for inhibitors of the PD-1 pathway, including but not limited to an ELISA assay, a RIA assays, a Western blot analysis, and homogenous assays relying on a detectable biological interaction not requiring separation or wash steps (e.g., see AlphaScreen™ from PerkinElmer®) and/or SPR-based technology (e.g., see BIACore®). The assay may be a simple "yes/no" assay to determine whether there is a change in the ability to form the known antibody/antigen complex. The assay is easily made quantitative by utilizing any number of assays, especially an ELISA-based assay, a homogenous assay, or an SPR-based assay. To this end, the present invention relates to any such assay, regardless of the known methodology employed, which measures the ability of a test compound to compete with the anti-PD-1 antibodies described herein to an appropriate peptide or protein mimetic of PD-1 or an identified target region within PD-1.

Examples are provided below further illustrating different features of the present invention. The examples also illustrate useful methodology for practicing the invention. These examples do not limit the claimed invention.

EXAMPLE 1

Generation of Monoclonal Antibodies to PD-1

Monoclonal antibodies directed to human PD-1 (SEQ ID NO:1) were generated by vaccinating mice with a DNA expression vector which encodes human PD-1.

Construction of PD-1 vector for mouse vaccination and hybridoma generation: Synthetic nucleotide gene fragments encoding amino acid sequences of human PD-1 (SEQ ID NO:1; NCBI Genbank Accession no. NP_005009) were constructed. The fragments were inserted into the V1Jns vector (SEQ ID NO:3; Shiver et al., "Immune Responses to HIV gp120 Elicited by DNA Vaccination," in *Vaccines* 95, Eds. R. M. Chanock, F. Brown, H. S. Ginsberg & E. Norrby, Cold Spring Harbor, N.Y.: Cold Spring Harbor Laboratory Press, 1995, 95-98) at Bgl II site to create V1Jns-PD-1. The authenticity and orientation of the inserts were confirmed by DNA sequencing.

Production of stable cell lines: For generation of permanent cell lines, PD-1 and PD-L1 (SEQ ID NO:2; NCBI Genbank Accession no. AAP13470) fragments were first amplified by PCR with custom oligodeoxynucleotides to create unique Hind III and Xho I sites at 5' and 3' ends, respectively, and then cloned into Hind III and Xho I sites of pcDNA6-/myc-his vector (Invitrogen Corp.). The resultant plasmids, pcDNA-PD-1 and pcDNA-PD-L1, were sequence-verified. Expression of PD-1 or PD-L1 from these vectors was confirmed in Western blot analysis of transiently transfected HEK293 cells (data not shown). To establish permanent cell lines expressing PD-1 or PD-L1, HEK293 cells were respectively transfected with pcDNA-PD-1 or pcDNA-PD-L1, and the transfectants were selected under blasticidin at 10 ug/ml for 3 weeks. The cells were then stained for surface expression of PD-1 or PD-L1 in flow cytometry, and high producing cells were subcloned by flow cytometry based cell sorting.

MAb production: Female Balb/c mice were injected with 0.1 mg/dose DNA plasmids V1Jns-PD-1 encoding human PD-1, as described in Example 1, with 1 mg/mL DNA in saline at days 0, 3, 7, and 10 by either intrasplenic or intramuscular modes. Further injections were performed 45 days later by either intrasplenic or intramuscular modes, and a final set of injections were performed with 293 cells expressing human PD-1 at $6 \times 10^7$ cells/mouse intraperitoneally. Splenocytes were collected from the mice and hybridoma fusions were generated and screened by well-established methods (e.g., Stewart, S. J., "Monoclonal Antibody Production," in *Basic Methods in Antibody Production and Characterization*, Eds. G. C. Howard and D. R. Bethel, Boca Raton: CRC Press, 2000). PEG-1500 (Roche) was employed as a chemical fusion reagent, and limiting dilution ELISAs were performed to assure antigen reactivity and monoclonality.

EXAMPLE 2

Biophysical Screening

Figure 2:
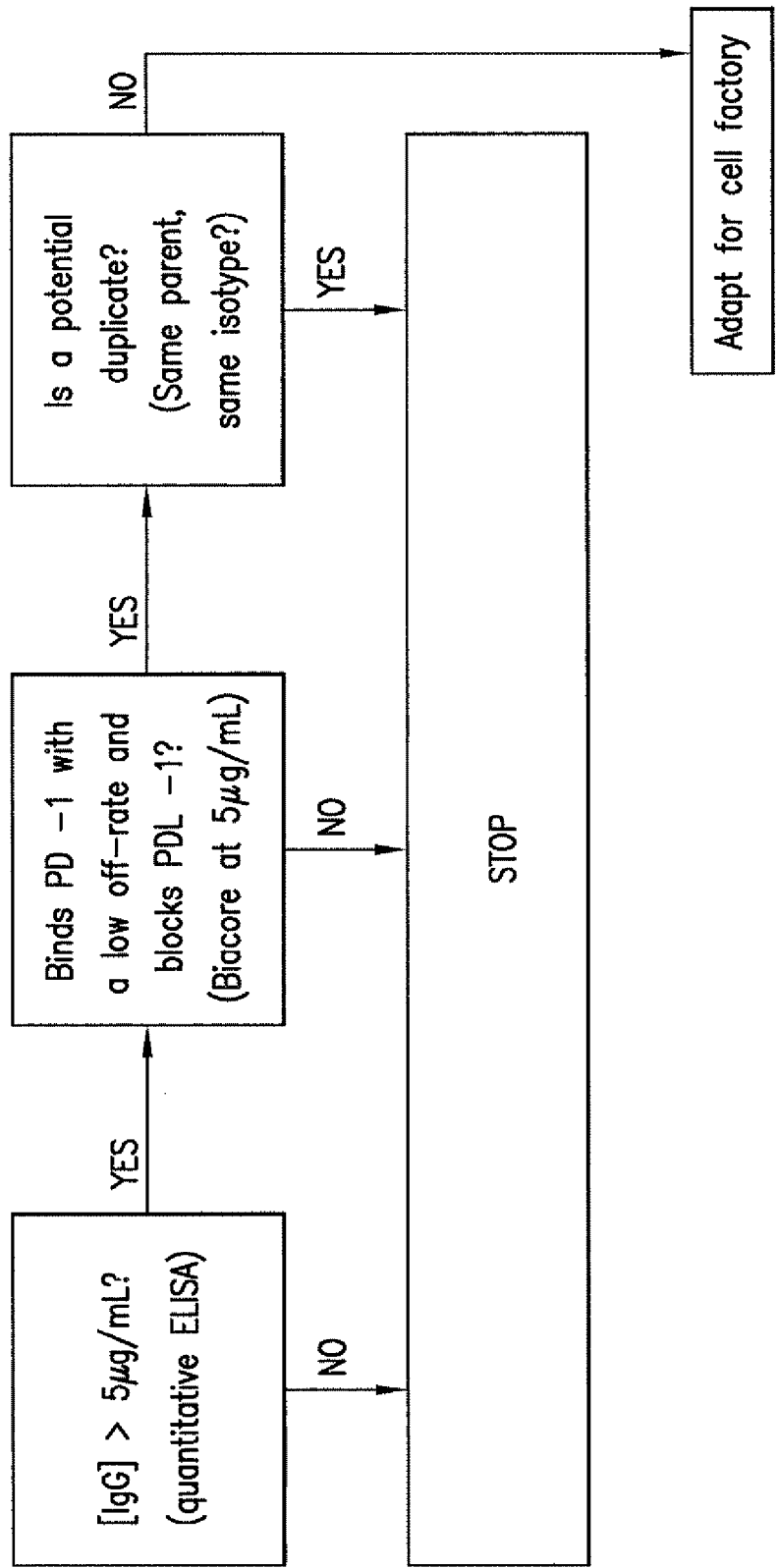
FIG. 2 illustrates the experimental flowchart used to screen for anti-PD-1 monoclonal antibodies using biophysical methods (see Example 2, infra).

Further screening was accomplished by biophysical methods. The flowchart in FIG. 2 was followed. Concentrations of hybridoma supernatants were determined by a quantitative anti-mouse IgG ELISA, and if the concentration was greater than 5 µg/mL, supernatants were diluted to 5 µg/mL. Clones producing less than 5 µg/mL mouse IgG were not pursued.

An assay was then developed on the Biacore® platform to determine binding to PD-1, blocking of PD-L1, and to counter-screen for the human Fc portion of a recombinant PD-1/Fc fusion protein (R&D Systems) used. Biacore® instruments incorporate microfluidics technology and surface plasmon resonance (SPR). The angle of polarized light reflecting from the side of a gold-coated sensor opposite to the solution phase is a function of the evanescent wave extending into the solution phase and sensitive to the refractive index near that interface. This refractive index is proportional to the mass density of adsorbates (e.g., an antigen or antibody) near the sensor chip interface, and reported in Response Units. Using a Biacore 2000 (GE Healthcare), PD-1/Fc was covalently immobilized with EDC/NHS to one surface of a CM5 dextran chip (Biacore AB, GE Healthcare), homologous Fc (R&D Systems) to another, and one surface was capped and left blank. Hybridoma supernatants were flowed over all surfaces, and then a recombinant PD-L1/Fc protein (R&D Systems) was flowed over all surfaces. Time-resolved signals were acquired from all surfaces simultaneously, and the signal from the blank control surface was subtracted as a negative control. MAbs with greater than 100 peak Response Units were considered to bind to PD-1, and those with less than 10 additional Response Units under PD-L1/Fc injection were considered to block PD-L1. No response was detected to any mAb on the Fc control surface.

Finally, each mAb was isotyped with IsoStrips (Roche Diagnostics) following manufacturer's directions. MAbs that could potentially derive from the same clone (i.e., had the same potential parent cell and had the same isotype) were assumed to be duplicate and only one of each pair was retained.

To produce a greater amount of serum-free mAbs, the remaining hybridomas were adapted to serum-free conditions and grown in CELLine™ CL-1000 flasks (BD Biosciences, Franklin Lakes, N.J.) following the manufacturer's directions.

Of the 38 monoclonal antibodies tested, 14 were chose for further analysis (see Example 3).

EXAMPLE 3

In Vitro Cell-Based Binding and Blocking Data

Several in vitro experiments were performed to determine both the binding of each identified mAb to cells expressing PD-1 and the ability to block PD-L1. 293 cells were transfected to express PD-1 on their cell membranes. Human CD4$^+$ cells were activated by incubation with anti-CD3/anti-CD28 beads (approximately 1 bead: 1-2 cells) for 48-72 hours at 37° C. Rhesus CD4$^+$ cells ($2 \times 10^6$ cells/mL) were activated by incubation in plates coated with 1 µg/mL anti-CD3/anti-CD28 for 24-72 hours at 37° C.

The results are summarized in Table 4. Criteria for further development included the following: a: binding to PD-1 on human CD4 cells (>100 relative MFI units), b: cross-reactive with PD-1 on rhesus CD4 cells (>700 relative MFI units), c: blocking of recombinant human PD-L1/Fc binding to PD-1 expressed on transfected 293 cells (>90% inhibition), d: blocking of recombinant human PD-L1/Fc binding to human PD-1 on activated human CD4 T cells (>50% inhibition), and e: blocking recombinant human PD-L1/Fc binding to rhesus PD-1 on activated rhesus CD4 T-cells (>50% inhibition). Numbers in Table 4 that met one of these criteria are starred (*). The most important criteria are blocking of human PD-1 to human PD-L1 expressed natively or transiently (criteria c and e). Binding/blocking criteria for rhesus PD-1 (criteria b and e) were beneficial but not essential for our selection. In all cases, the binding of the mAbs to PD-1 determined by SPR (see Example 2) were confirmed by natively expressed PD-1 (criterion a); although this did not provide further differentiation. The mAbs that were selected for further study are marked with a double star (**) Table 4. Three PD-1-binding but PD-L1-non-blocking mAbs were also carried forward as controls (mAb 3H4, mAb 6D10 and mAb 2.3A9; shown in italics at the bottom of the table).

TABLE 4

| Clone ID | a:<br>bind to PD-1 on<br>activated<br>human CD4<br>cells (MFI) | b:<br>bind to PD-1 on<br>activated rhesus<br>CD4 cells<br>(MFI) | c:<br>block human<br>PD-L1 binding<br>to human PD-1<br>on 293 cells<br>(% inhibition) | d:<br>block human<br>PD-L1 binding<br>to PD-1 on<br>activated<br>human CD4<br>cells<br>(% inhibition) | e:<br>block human<br>PD-L1 to PD-1<br>on activated<br>rhesus CD4<br>cells<br>(% inhibition) |
|---|---|---|---|---|---|
| 28.11** | 139 | 718* | 99.1* | 61.5* | 64.2* |
| 28.12 | ND | 565 | ND | ND | ND |
| 28.6 | 127 | 89 | 37.5 | 8.7 | 0.1 |

TABLE 4-continued

| Clone ID | a: bind to PD-1 on activated human CD4 cells (MFI) | b: bind to PD-1 on activated rhesus CD4 cells (MFI) | c: block human PD-L1 binding to human PD-1 on 293 cells (% inhibition) | d: block human PD-L1 binding to PD-1 on activated human CD4 cells (% inhibition) | e: block human PD-L1 to PD-1 on activated rhesus CD4 cells (% inhibition) |
|---|---|---|---|---|---|
| 1.8A10** | 129 | 310 | 99.4* | 51.7* | 24.0 |
| 1B8** | 145 | 1193* | 97.6* | 82.1* | 82.3* |
| 1D4 | 129 |  | 98.9* | 22.8 | 0.1 |
| 1E3.14 | 130 | 823* | 98.4* | 27.9 | 20.0 |
| 1E4 | 129 | 882* | 99.5* | 47.4 | 15.9 |
| 1E5 | 123 | 862* | 96.1* | 52.7* | 35.9 |
| 1G7** | 137 | 812* | 98.8* | 74.3* | 56.5* |
| 20B3.1** | 154 | 1244* | 98.2* | 59.6* | 75.3* |
| 2B6 | 133 |  | 82.9 | 36.2 | 24.5 |
| 2G3 | 124 | 807* | 98.8* | 36.8 | 0.1 |
| 4G3 | 131 | 10 | 24.9 | 22.9 | 0.1 |
| 5F3.1 | 128 | 738* | 98.8* | 37.3 | 31.2 |
| 5H10.1 | 188 | 635 | 97.1* | 33.2 | 11.2 |
| 7G3** | 129 | 655 | 92.7* | 57.8* | 25.5 |
| 3H4 | 130 | ND | ND | ND | ND |
| 6D10 | 133 | ND | ND | ND | ND |
| 2.3A9 | 134 | ND | ND | ND | ND |

ND: not determined
a: MFI (mean fluorescent intensity) of 0.2 μg/ml IgG binding to (human) PD-1 naturally expressed on activated human CD4⁺cells at 37° C.
b: MFI of 1.0 μg/ml IgG binding to (rhesus) PD-1 naturally expressed on activated rhesus CD4⁺cells at 37° C.
c: % inhibition of recombinant PD-L1/Fc binding to 293 cells expressing human PD-1 by 20 μg/ml IgG at 4° C.
d: % inhibition of recombinant PD-L1/Fc binding to activated human CD4⁺cells by 0.2 μg/ml IgG at 37° C. (mean of 2 experiments)
e: % inhibition of recombinant PD-L1/Fc binding to activated rhesus CD4⁺cells by 0.2 μg/ml IgG at 37° C. (mean of 2 experiments)

EXAMPLE 4

MAb IgG Sequence Identification

Total RNA was isolated from each hybridoma cell line using the SV Total RNA System from Promega. Total cellular RNA was converted to cDNA priming with random decamers using the Reverse Transcription System from Promega. The heavy chain variable regions ($V_h$) and light chain variable regions ($V_l$) were amplified from the cDNA by the polymerase chain reaction (PCR) using Supertaq (Novagen) and degenerate primers described by Krebber, et al. (1997, *Journal of Immunological Methods* 201:35-55) and the kappa primer sets in Novagen's Mouse IgG Primer Set kit. The PCR products were cloned into pGEM T Easy vector using the pGEM T Easy Vector Systems kit from Promega. Subsequent clones were screened for insert by an EcoRI digest and clones positive for an insert were sequenced using primers specific to the T7 promoter by Genewiz. The amino acid sequences for the heavy chain variable domain and/or the light chain variable domain of mAb 1B8, mAb 20B3.1, mAb 7G3, mAb 3H4, mAb 2.3A9, mAb 1G7, mAb 1.8A10, mAb 28.11, and mAb 6D10 are listed below. The underlined portions of the sequences are the CDRs. The CDRs (CDR1, CDR2, CDR3 from the $NH_2$ to the COOH terminus) were identified from consideration of the Kabat and Chothia definitions.

The amino acid sequences of the mAb 1B8 $V_h$ (SEQ ID NO:4) and $V_l$ (SEQ ID NO:5) are as follows:

mAb 1B8 $V_h$ amino acid sequence
```
                                          (SEQ ID NO: 4)
  1 EVQLVLSGGG FVQPGGSLKL SCAASGFTFS SYAMSWVRQN
    PERRLVWVAT
 51 ITGGGRNTYY PDSVKGRFTI SRDNAKNTLY LQMSSLRSED
    TAMYYCTRQG
101 YDGYTWFAYW GQGTLVTVS
``` mAb 1B8 $V_l$ amino acid sequence
```
                                          (SEQ ID NO: 5)
  1 DIVLTQSPTS LAVSLGQRAT ISCRASESVD NSGISFMNWF
    QQKPGQPPKL
 51 LIYAASNPGS GVPARFSGSG SGTDFSLNIH PMEEDDTAMY
    FCQQSKEVPW
101 TFGGGTELEI KR
```

The amino acid sequences of the mAb 20B3.1 $V_h$ (SEQ ID NO:12) and $V_l$ (SEQ ID NO:13) are as follows:

mAb 20B3.1 $V_h$ amino acid sequence
```
                                         (SEQ ID NO: 12)
  1 EVKLVESGGG LVKPGGSLKL SCAASGFTFS SFGMSWVRQT
    PEKRLEWVAT
 51 ISGGGSNTYY PDSVKGRFTI SRDNAKNNLY LQMTSLTSED
    TALYYCTRIY
101 DVAWFAYWGQ GTLVTVS
``` mAb 20B3.1 $V_l$ amino acid sequence
```
                                         (SEQ ID NO: 13)
  1 DIVLTQSPAS LAVSLGQRAT ISCRASESVD NSGISFMNWF
    QQKPGQPPKL
 51 LIYAASNQGS GVPARFSGSG SGTDFSLNIH PMEEDDTAMY
    FCQQSKEVPW
101 TFGGGTKLEI KR
```

The amino acid sequences of the mAb 7G3 $V_h$ (SEQ ID NO:18) and $V_l$ (SEQ ID NO:19) are as follows:

mAb 7G3 $V_h$ amino acid sequence
```
                                         (SEQ ID NO: 18)
  1 QVQLQQSGTE LVRPGVSVKI SCKGSGYSFT DYALHWMKQS
    HAKSLEWIGV
```

-continued

```
 51 ISTHYGDTVY NQRFKGKATM TVDKSSSTAY MELARLTSED
    SAIYYCAREG
101 YGSLFYFDQW GQGTPLTVS
``` mAb 7G3 V_l amino acid sequence
(SEQ ID NO: 19)
```
  1 CLMTQTPLSL PVSLGDQASI SCRSSQTIVH SDGNTYLEWY
    LQKSGQSPKL
 51 LIYKVSNRFS GVPDRFSGSG SGTDFTLKIS RVEAEDLGVY
    YCFQGSHVPY
101 TFGGGTRLEI RR
```

The amino acid sequences of the mAb 3H4 V_h (SEQ ID NO:55) and V_l (SEQ ID NO:56) are as follows:

mAb 3H4 V_h amino acid sequence
(SEQ ID NO: 55)
```
  1 QIQLQQSGPE LVKPGASVKI SCKASGYTFT DYYINWVKQK
    PGQGLEWIGW
 51 IYPGSVNTKY NEKFRGKATL TVDTSSSTAY IQLSGLTSED
    TAVYFCARYS
101 NWFFDVWGAG TAVTVS
``` mAb 3H4 V_l amino acid sequence
(SEQ ID NO: 56)
```
  1 DIVMTQSPSS LSASLGERVS LTCRASQEIS GYLSWLQQKP
    DGTIKRLIYA
 51 ASTLDSGVPK RFSGSRSGSD YSLSISSLES EDFADYYCLQ
    YASYPYTFGG
101 GTKLEIKR
```

The amino acid sequences of the mAb 2.3A9 V_h (SEQ ID NO:67) and V_l (SEQ ID NO:68) are as follows:

mAb 2.3A9 V_h amino acid sequence
(SEQ ID NO: 67)
```
  1 QVQLQQSDAE LVKPGTSVKI SCKASGYTFT DHAIHWLKQE
    PDQGLEWIGY
 51 ISPGYGDIEY NEKFKGKATL TADKSSSTAY MQLSSLTSED
    SAVYFCKVTT
101 GYWGQGTTLT VS
``` mAb 2.3A9 V_l amino acid sequence
(SEQ ID NO: 68)
```
  1 DVLMTQTPLT LSVTIGQPAS ISCKSSQSLL NSDGKTYLNW
    LLQRPGQSPK
 51 RLIYLVSELD SGVPDRFTGS GSGTDFTLKI SRVEAEDLGI
    YYCWQGTHFP
101 HTFGAGTKLE LKR
```

The amino acid sequences of the mAb 1G7 V_h (SEQ ID NO:26) and V_l (SEQ ID NO:27) are as follows:

mAb 1G7 Vh amino acid sequence
(SEQ ID NO: 26)
```
  1 EIQLQQSGPE LVKPGASVKV SCKASGYAFT SYNIYWVKQS
    HGKSLEWIGY
 51 IDLYNGDTSY NEKFKGKATL TVDKSASTAY MHLNSLTSE
    DSAVYYCSRE
101 GRLSFDYWGQ GTLVTVSAA
``` mAb 1G7 V_l amino acid sequence
(SEQ ID NO: 27)
```
  1 DIVLTQSPAS LAVSLGQRAT ISCRASESVD SYGNSFMNWY
    QQKPGQPLKL
 51 LIYLASNLDS GVPARFSGSG SGTDFSLTID PVEADDPATY
    YCQQNNEVPL
101 TFGAGTKLEL KR
```

The amino acid sequences of the mAb 1.8A10 V_h (SEQ ID NO:34) and V_l (SEQ ID NO:35) are as follows:

mAb 1.8A10 V_h amino acid sequence
(SEQ ID NO: 34)
```
  1 EVQLVESGGG LVKPGGSLKL SCAASGFTFS NYDMSWIRQT
    PEKRLEWVAY
 51 ISGGGGNTYY PDTLKGRFTI SRDNAKNTLY LQMSSLKSED
    TAMFYCVRIS
101 LTGIFDYWGQ GTTLTVSSA
``` mAb 1.8A10 V_l amino acid sequence
(SEQ ID NO: 35)
```
  1 DVLMTQTPLS LPVSLGDQAS ISCRSSQSIV QSNGNTYLEW
    YLQKPGQSPK
 51 LLIYKVSNRF SGVPDRFSGS GSGTDFTLKI SRVEAEDLGV
    YYCFQGSHVP
101 WTFGGGTKLE IKR
```

When cloning antibody variable regions from hybridoma cell lines using standard techniques, non-functional rearranged variable regions can be obtained. It is thought that these sequences originate from the myeloma cell lines used for the fusion process. These non-functionally rearranged mRNAs are pseudogenes which can exist in the cell at levels greater than the normal antibody mRNA (see, e.g., Ostermeier and Michel, 1996, *Nucleic Acids Research* 24:1979-1980). When sequencing the V_h and V_l of mAb 28.11, two variable domain like sequences were identified for each. It is likely that one of the V_h sequences and one of the V_l sequences represents a pseudogene. The two V_h sequences are referred to herein as V_h 28.11.1 and V_h 28.11.2, and the two V_l sequences are referred to herein as V_l 28.11.1 and V_l 28.11.2.

Thus, a first V_h amino acid sequence from mAb 28.11 designated as V_h 28.11.1 (SEQ ID NO:40) is as follows:

V_h 28.11.1 amino acid sequence (SEQ ID NO: 40) from mAb 28.11
```
  1 EVKLVESGGG LVKPGGSLKL SCAASGFTFN SYGMSWVRQT
    PDKRLEWVAT
 51 ISGGGSYTYY PDSVQGRFTI SRDNAKNNLY LQMSSLRSED
    TALYYCASGN
101 YVYVMDYWGQ GTSVTVSSA
```

A second V_h amino acid sequence from mAb 28.11 designated as V_h 28.11.2 (SEQ ID NO:47) is as follows:

V_h 28.11.2 amino acid sequence (SEQ ID NO: 47) from mAb 28.11
```
  1 QVQLQQSGPE LVRPGVSVKI SCKGSGYIFT DYVMHWVKQS
    PAKSLEWIGV
 51 ISTYYSNINY NQKFKGKATM TVDKSSSTAY LELARLTSED
    SAIYFCAREG
101 FGRPYWYFDV WGAGTTVTVS SA
```

A first V_l amino acid sequence from mAb 28.11 designated as V_l 28.11.1 (SEQ ID NO:41) is as follows:

V_l 28.11.1 amino acid sequence (SEQ ID NO: 41) from mAb 28.11
```
  1 DVMMTQTPLS LPVSLGDQAS ISCRSSQTIV HGNGNTYLEW
    YLQKPGQSPK
```

-continued

```
 51 LLIYKVSNRF SGVPDRFSGS GSGTDFTLKI SRVEAEDLGV
    YYCFQGSHVP

101 YTFGGGTKLE IKR
```

A second $V_l$ amino acid sequence from mAb 28.11 designated as $V_l$ 28.11.2 (SEQ ID NO:48) is as follows:

```
V_l 28.11.2 amino acid sequence (SEQ ID NO: 48) from
mAb 28.11
  1 AYQMTQSPSS LSASVGDRVT IKCQASENIY SSLAWYQQKP
    GKPPKLLIYS

51 ASTLASGVPS RFSGSGSGTE FTLTISSLQP EDFATYYCQQ
    GFGTSNVENP

101 FGGGTKVEIK R
```

The amino acid sequence of the mAb 6D10 $V_h$ (SEQ ID NO:63) is as follows:

```
mAb 6D10 V_h amino acid sequence
                                      (SEQ ID NO: 63)
  1 EVKLVESGGG LVQPGGSRKL SCAASGFTFS SFGMHWVRQA
    PEKGLEWVAY

51 VSSASSVIHY ADTVKGRFTI SRDNPKNTLF LQMTSLRSED
    TAMYYCARSG

101 YYGTWFPYWG QGTLVTVS
```

EXAMPLE 5

BIACORE® Fab Affinities and Solution Phase ELISA IgG Affinities pFab4 vector construction: The variable region of the heavy chain and light chain of 1B8 and 3H4 were cloned into the Fab producing pFab4 vector using Dry Down In Fusion kit (Invitrogen). Primers were designed to be homologous to the beginning of the framework-1 region and the end of the J region of the variable regions of the heavy and light chains. Primers were designed for use in the Dry Down InFusion system as described in the manufacturer's instructions. The variable region of the light chain was cloned into the XbaI and BsiWI sites of pFab4, and the variable region of the heavy chain was cloned in using the XhoI and ApaI sites. Clones were screened for insert by digesting with XbaI and BsiWI or XhoI and ApaI. Clones positive for insert were sequence-confirmed.

Surface plasmon resonance (SPR) analysis: Monomeric Fabs were generated from IgGs (mAb 1B8, mAb 1.8A10, and mAb 3H4) by enzymatic digestion. Fractions from the purification column were collected and tested in the Caliper LabChip® system. Only fractions containing pure monomeric Fabs were selected for SPR analysis. Beginning with concentrations determined from the Caliper LabChip®, dilution series were made for each Fab and tested on a Biacore® T100 with the standard kinetic affinity wizard against covalently immobilized PD-1/Fc fusion protein. Data were fit in the BIAevaluation software under various starting assumptions and the range of fit $K_d$ are listed below. All tested Fabs have high affinity (low $K_d$), although 1B8 is especially high (see Table 5, Fab $K_d$).

Solution phase ELISA of IgGs: IgGs (mAb 1B8, mAb 1.8A10, and mAb 3H4) were tested in solution phase ELISA. The experimental procedure and data analyses followed the method described in K. High et al., Determination of picomolar equilibrium dissociation constants in solution by enzyme-linked immunosorbent assay with fluorescence detection, Anal. Biochem., 347(1):159-161, 2005. PD-1/Fc (R&D Systems) was used as the protein substrate and titrated from 1950 ng/mL in 1.5-fold dilutions into 24 wells of a 96-well low-binding reaction plate. An equal volume of IgG (either mAb 1B8, mAb 1.8A10, or mAb 3H4) was added at 15, 3, or 1 ng/mL concentration to each well and incubated overnight. High-binding 96-well ELISA plates were coated with 50 µL 2 µg/mL PD-1/Fc overnight. After washing and blocking, 50 µL of each PD-1/Fc: IgG mixture was transferred to the ELISA plate, incubated for 30 minutes, washed, incubated with goat anti-mouse antibody conjugated to HRP (human absorbed) for one hour, washed, developed with 10-Acetyl-3,7-dihydroxyphenoxazine (ADHD) for three minutes, and read on a fluorescent plate reader. All incubations occurred at room temperature. Data were analyzed as described in K. High et al. Several replicates were conducted on multiple plates and multiple days and analyzed independently to determine a range of experimental equilibrium affinity $K_d$ values. The mean $K_d$ and standard error of the mean are reported in Table 5. The $K_d$ are lower (improved) for IgGs relative to Fabs due to avidity effects, i.e., the binding of both arms of the divalent IgG to the protein substrate relative to the monovalent Fab.

TABLE 5

| mAb | Fab $K_d$ (SPR) | IgG $K_d$ (solution-phase ELISA) |
|---|---|---|
| 1B8 | 5.3-7.0 nM | 30 ± 5 pM |
| 1.8A10 | 34-43 nM | 440 ± 70 pM |
| 3H4 | 63-77 nM | 11 ± 1 pM |

EXAMPLE 6

IgG Epitope Mapping Characterization

The monoclonal antibodies identified as binding PD-1 were screened in a surface plasmon resonance "epitope footprinting" assay using a Biacore® 2000. Pairwise binding experiments were conducted using real-time biomolecular interaction analysis via SPR. The mAbs 20B3.1, 28.11, 1B8, 1.8A10, 3H4, 1G7, 7G3, 1E5 (see Table 4), 6D10, and 2.3A9 were tested in every pairwise combination. Recombinant PD-1/Fc fusion protein was immobilized onto a Biacore CM5 dextran surface, and a second surface was capped as blank negative control. In each cycle, a first mAb was flowed over both surfaces and binding to the immobilized PD-1 was observed. Then, a second mAb was flowed to see if it could also bind or if the epitope was blocked by the first mAb. The surfaces were regenerated with 100 mM HCl to prepare for the next cycle. Time-resolved signals were acquired throughout, and the blank control surface was subtracted. The results were that two clusters of mAbs are apparent. The mAbs 20B3.1, 28.11, 1B8, 1.8A10, 1G7, 7G3, and 1E5 all compete for the same epitope. That is, if one of these is bound to PD-1 in saturation, only no or low quantity of any other mAb in this first cluster can bind. The second cluster consisting of mAbs 3H4, 6D10, and 2.3A9 compete with each other for the same epitope. However, the binding of any mAb in the first cluster has little or no apparent effect upon the subsequent capacity of any mAb in the second cluster to bind to PD-1. Likewise, the binding of any mAb in the second cluster has little or no apparent effect upon the subsequent binding of any mAb in the first cluster. This is consistent with the identification of two distinct target regions on PD-1. The clustering of the mAbs is identical to the categorization of mAbs into PD-L1 blocking and non-blocking subgroups (see Example 3). The conclusion is that the first group (mAbs 20B3.1, 28.11, 1B8, 1.8A10, 1G7, 7G3, and 1E5) bind to the same target region and that this interferes with the binding of PD-L1 to PD-1. The second group (mAbs 3H4, 6D10, and 2.3A9) bind to a second target region that does not interfere with PD-L1/PD-1 binding.

EXAMPLE 7

In Vivo SIV-Infected Rhesus Macaques Treated with mAb and Integrase Inhibitor

Figure 3A:
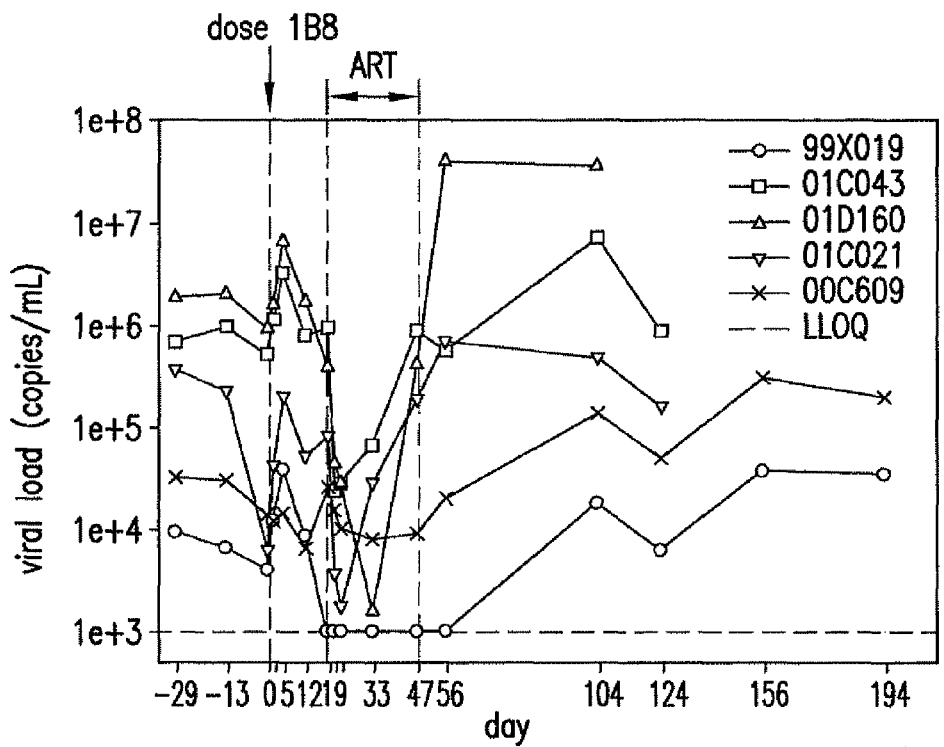
FIG. 3 tracks the viral loads of SIV-infected rhesus macaques treated with anti-PD-1 antibody, mAb 1B8 ("1B8"), plus an integrase inhibitor (see Example 7, infra). (A) Viral loads of rhesus macaques receiving a single infusion of 1B8 on day 0, followed by daily ART (integrase inhibitor) from day 19-47. (B) Viral loads of rhesus macaques receiving daily ART (integrase inhibitor) on days 0-47 and a single infusion of 1B8 on day 12. LLOQ indicates the lower limit of quantification for the assay.
Figure 3B:
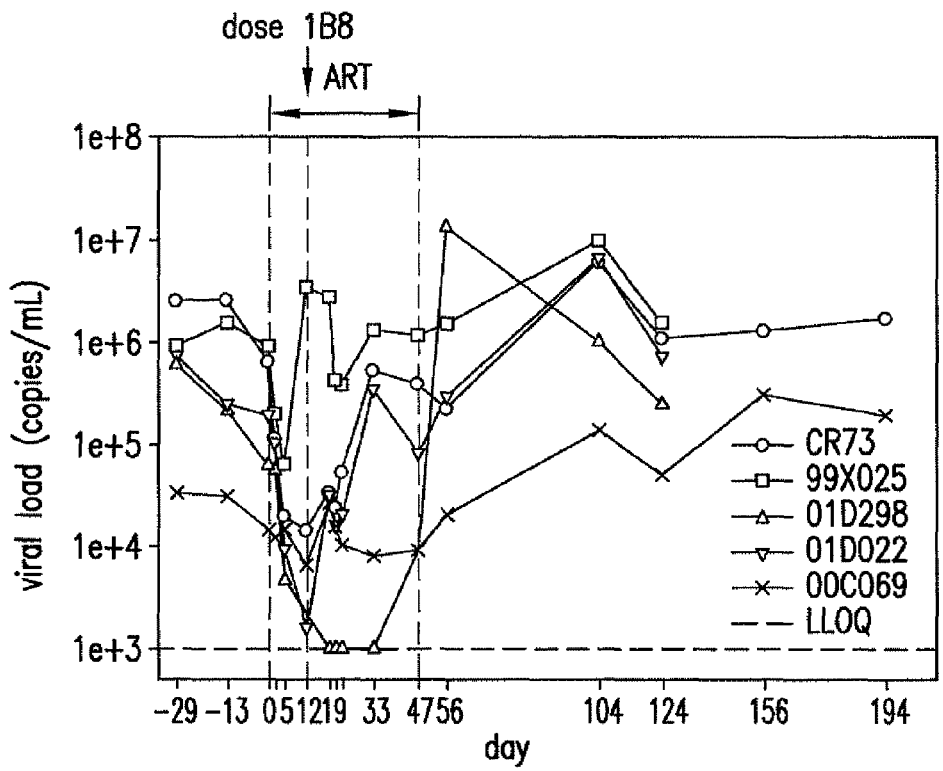
Figure 4A:
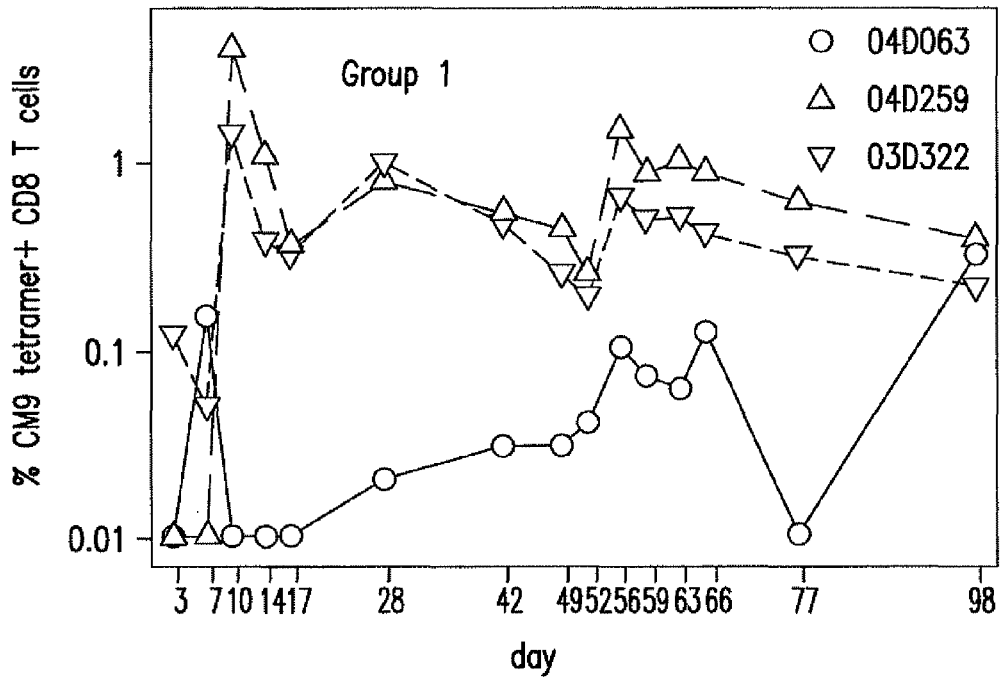
FIG. 4 shows the percent of $CD3^+/CD8^+$ lymphocytes which are positive for a SIVgag CM9 tetramer in twelve naïve rhesus macaques (4 groups, 3 monkeys per group) vaccinated with an adenovector encoding SIV gag (see Example 8, infra). (A) and (B) show Groups 1 and 2, respectively: simultaneously treated with anti-PD-1 antibody mAb 1B8 intravenously (A) or intramuscularly (B) at the time of vaccination with a SIV-gag antigen at days 0 and 49. (C) shows Group 3: received no mAb treatment at day 0 and mAb 1B8 at day 49 intravenously. (D) shows Group 4: given intravenous isotype-matched IgG negative control at days 0 and 49.
Figure 4B:
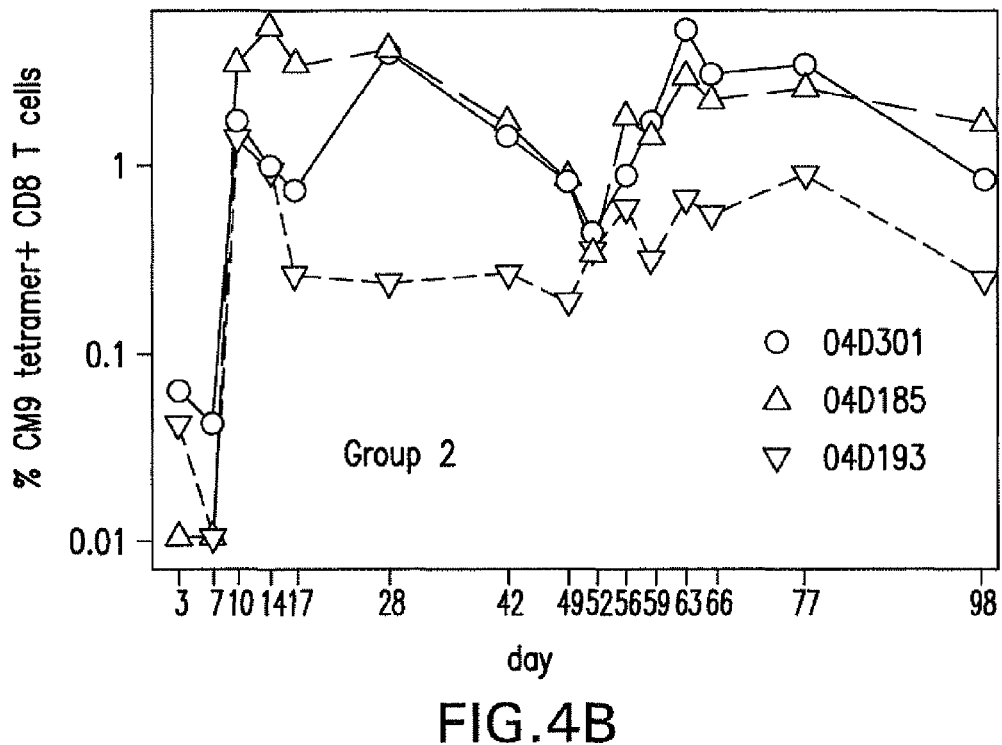
Figure 4C:
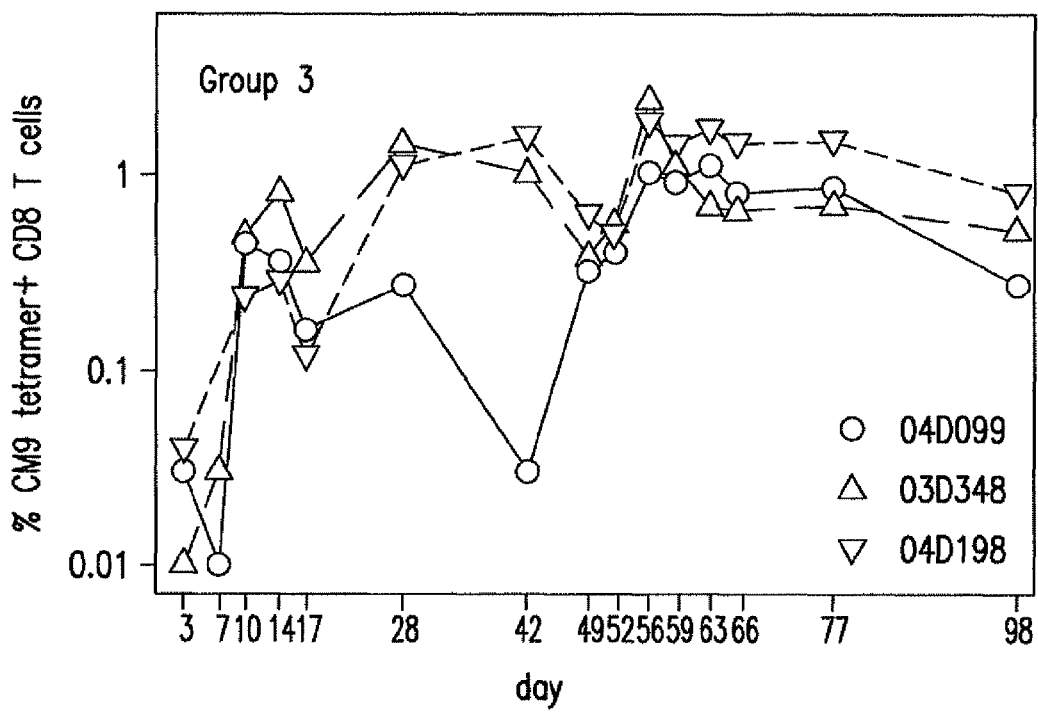
Figure 4D:
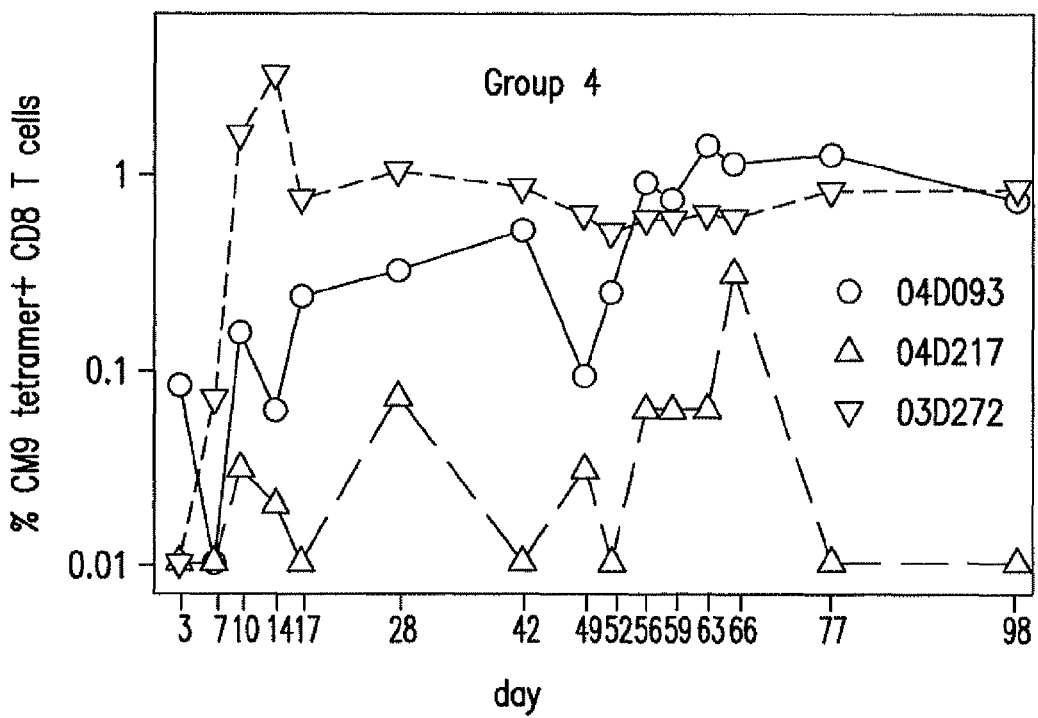

Nine rhesus macaques were infected with SIVmac239 over 500 days prior the initiation of the study at day 0. Viral loads were determined from real-time PCR of plasma collected from each monkey at day −29, −13, 0, 5, 12, 19, 23, 33, 47, and 56. In group 1, monkeys received a single infusion of mAb 1B8 at 5 mg/kg on day 0 (see FIG. 3A). In group 2, monkeys were given antiretroviral therapy ("ART") in the form of an inhibitor of HIV-1 and SIV integrase in rhesus macaques, L-870812 (Hazuda et al., 2004, *Science* 305:528-532) once daily beginning on day 0 (see FIG. 3B). On day 12, monkeys in group 2 were given a single infusion of mAb 1B8 at 5 mg/kg. Monkeys in group 1 were given the integrase inhibitor once daily beginning on day 19. On day 47, all integrase inhibitor treatments ceased. One monkey was followed as an infected but untreated control (00C609 in FIGS. 3A and 3B). Most animals were released from the study after day 124. However, three were followed until day 194 to demonstrate that viral loads had achieved steady state.

Two monkeys (99X019 and 01D298) reached an undetectable viral load (<1000 copies/mL) during the treatment. 01D298 rebounded to a high viral load level after treatment ended. Significantly, 99X019 reached an undetectable viral load due to mAb 1B8 treatment alone even before ART and maintained an undetectable viral load level 9 days after all treatments ended. All treated animals were affected by the single mAb 1B8 infusion treatment, characterized by a transient rise in viral loads (perhaps due to an increase in activated CD4), followed by a return to levels equal to or less than pre-treatment levels. These data indicate the utility of mAb 1B8, and potentially other mAbs in its class, for reducing viral loads either alone or in combination with anti-viral agents.

Figure 7A:
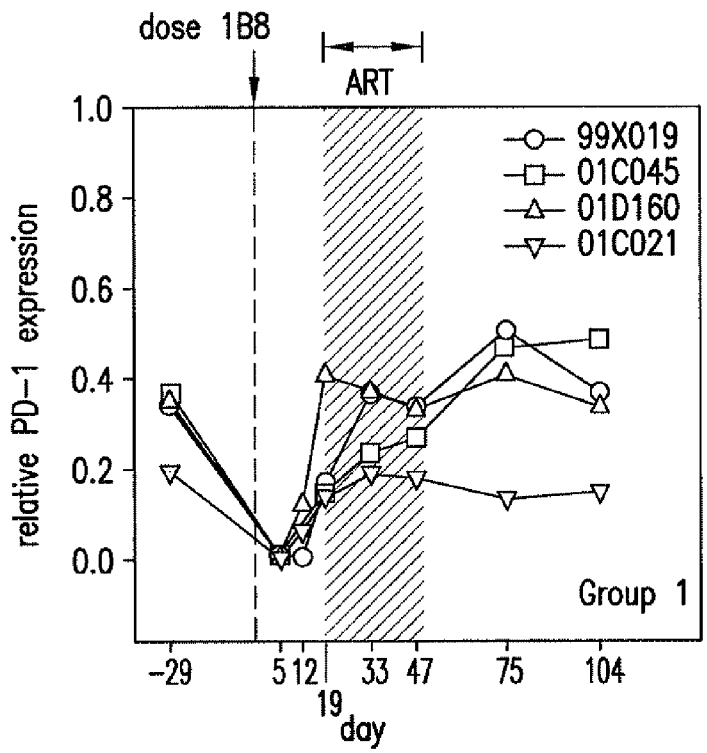
FIG. 7 shows the degree of in vivo blockade by the single infusions of mAb 1B8 ("1B8") in the SIV-infected rhesus macaques treated as described in Example 7. Lymphocytes in peripheral blood were stained with a mAb that bound PD-1 and competed with mAb 1B8 for the same epitope in the macaques receiving a single infusion of mAb 1B8 on day 0, followed by daily ART from day 19-47 (A) and the macaques receiving day ART on days 0-47 and a single infusion of mAb 1B8 on day 12 (B).
Figure 7B:
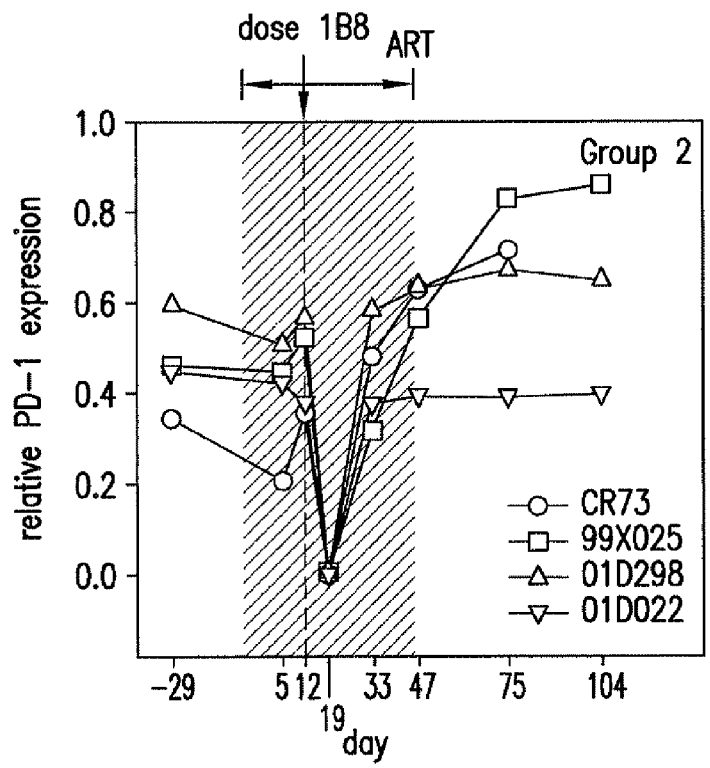

The degree of in vivo blockade by the single infusions of anti-PD-1 1B8 mAb was also measured. Lymphocytes in peripheral blood were stained with labeled mAb 28.11 which competes with mAb 1B8 for the same epitope (see Example 6). The results are shown in FIG. 7A for group 1 macaques (treated on day 0), and in FIG. 7B for group 2 macaques (treated on day 12). As can be seen in the figures, mAb 1B8-mediated blockade of at least 90-95% was maintained for at least 7 to 12 days after mAb 1B8 infusion depending upon the individual. Partial blockade (approximately 50%) continued for most monkeys until 19 to 21 days after mAb 1B8 infusion. The high efficiency and persistence of PD-1 blockade was consistent with the high affinity and low off-rate for mAb 1B8 in SPR analysis and the efficient blockade in vitro of PD-L1 by mAb 1B8 (see Example 3, Table 4) even at a low concentration of 0.2 μg/mL. Thus, infusion of mAb 1B8 at the 5 mg/kg dose, even as a mouse IgG, was able to achieve effective and persistent PD-1 blockade in monkeys.

EXAMPLE 8

Enhancement of Adenovector Vaccination with PD-1 MAb in Naïve Rhesus Macaques

Twelve naïve rhesus macaques were allocated into 4 groups to test whether PD-1 blockade can enhance adenovirus vector vaccines. All monkeys were vaccinated with adenovector type 5 encoding SIV gag antigen at a dose of $10^{10}$ viral particles ("vp") at days 0 and 49. Monkeys in groups 1 and 2 were simultaneously treated with mAb 1B8 at 5 mg/kg delivered intravenously or intramuscularly, respectively, at the time of adenovector vaccination. Monkeys in group 3 received no antibody treatment at day 0 and mAb 1B8 treatment at 5 mg/Kg at day 49 intravenously. Monkeys in group 4 were given an intravenous isotype-matched IgG negative control at 5 mg/Kg at days 0 and 49. All monkeys selected in this study have the Mamu A*01 allele permitting their T cell immune responses to be tracked in flow cytometry by T cell staining with Mamu A*01 tetramer folded with the SIV gag CM9 peptide. The percent of $CD3^+CD8^+$ lymphocytes positively stained by the CM9 tetramer for each monkey group is shown in FIG. 4.

Overall tetramer positive staining appeared above 1% on day 10 post vaccination, and peaked between day 10 and day 14. There is substantial variability amongst individuals in each group, expected from this suboptimal vaccination at $10^{10}$ vp dosing with adenovirus vectors in monkeys. However, enhancement by PD-1 blockade with mAb 1B8 treatment was observed for monkeys in groups 1 and 2. Since both groups were treated with 1B8, albeit by different routes, while monkeys in groups 3 and 4 received no mAb 1B8 treatment in the priming phase (before week 7), we analyzed the effects of mAb 1B8 treatment by comparing immune responses of groups 1+2 vs groups 3+4 on the peak response days 10, 14. The results were marginally statistically significant (day 10: p=0.045, day 14: p=0.051). Also, tetramer staining for two monkeys in group 2 was sustained through day 40.

The CM9 epitope restricted by the Mamu A*01 allele is highly immunodominant and well-conserved as will be appreciated by one familiar with the HIV research literature. Thus, it would be highly unusual, after two vaccinations, for a rhesus macaque to consistently fail to exhibit a response distinguishable from zero at every time point. Thus, animal 04D063 was re-tested for the Mamu A01 allele, and was found to be negative. Properly excluding this animal from the statistical analysis, and using a nonparameteric test appropriate for small sample sizes, we analyzed the effects of mAb 1B8 treatment by comparing the peak immune responses (mean of percent CM9 tetramer positive on days 10 and 14) of groups 1 and 2 together as one group vs groups 3 and 4 together as another group. The peak CM9-tetramer response was significantly higher (p=0.030) for the 1B8-treated group vs the nontreated group by a nonparametric Wilcoxon rank sum two-sided test.

Figure 5A:
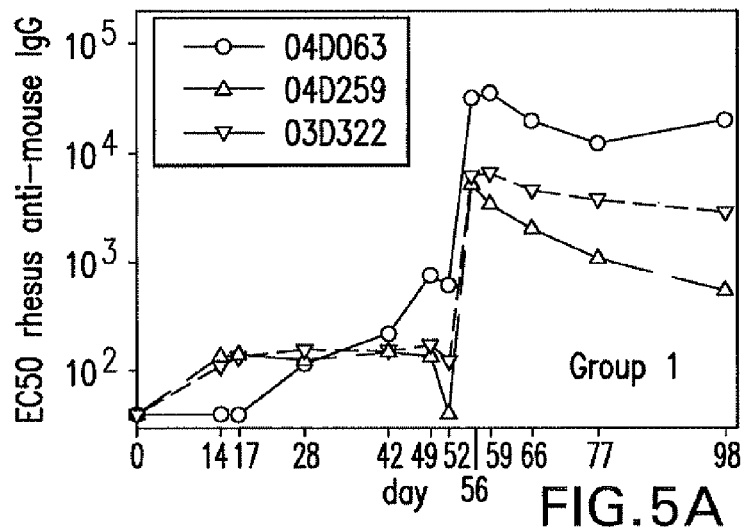
FIG. 5 shows the time course of rhesus anti-mouse antibodies in the rhesus macaques shown in FIGS. 4A-C (Groups 1-3) throughout the treatments as effective concentration at 50% (EC50) determined by fitting ELISA data to a standard four-point sigmoidal model.
Figure 5B:
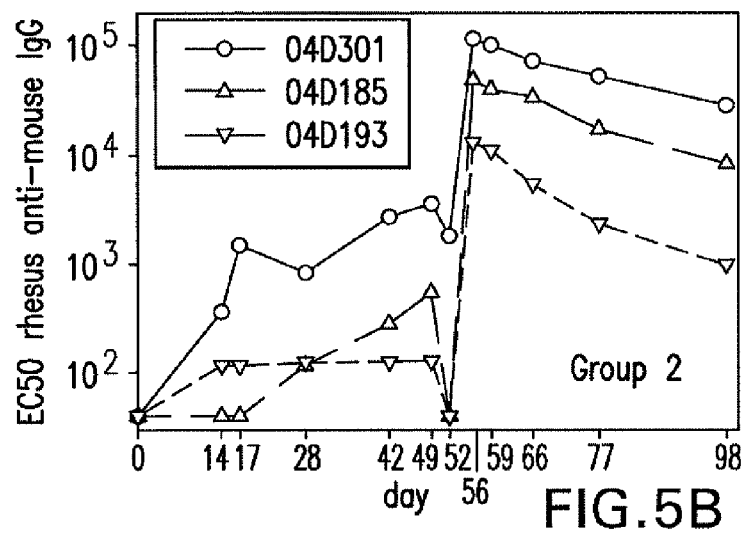
Figure 5C:
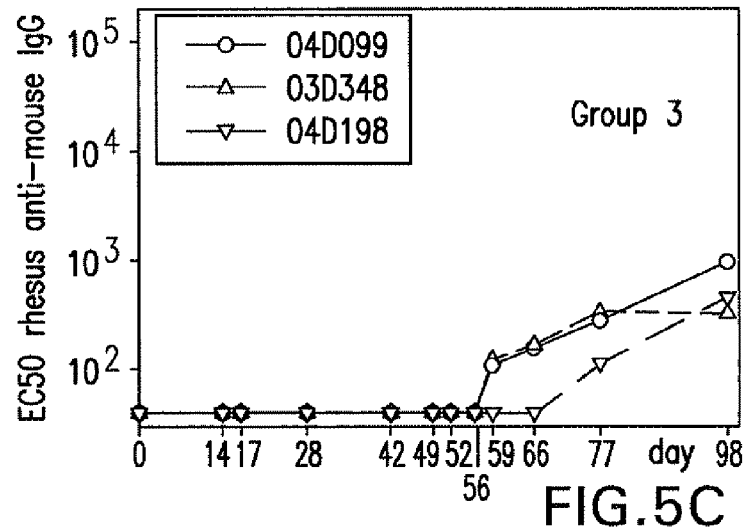

Because mAb 1B8 is a mouse IgG, its persistence in vivo and hence its efficacy ultimately will be limited by rhesus anti-mouse IgG antibodies ("RAMAs"). The presence of 1B8-specific RAMAs was tested by the following assay. 96-well microtiter plates were coated with 2 μg/mL mAb 1B8 and incubated overnight. Plates were coated, washed, and blocked for 1 hour at room temperature. Plasma samples were added in titration (1:40, 1:160, . . . , 1:655360) and incubated for 2 hours at room temperature. Wells were washed, incubated with 0.1 μg/mL biotinylated 1B8 for 0.75 hours, washed again, incubated with streptavidin-alkaline phosphatase for 0.75 hours, washed, then 10-Acetyl-3,7-dihydroxyphenoxazine (ADHP) was added and fluorescence from each well was measured with a standard plate reader. Data were fit to a standard four-point sigmoidal model, and the fit effective concentrations at 50% (EC50) values are shown in FIG. 5. We have monitored and confirmed that effective blockade of PD-1 by mAb 1B8 can last 10 to 12 days (see Example 7, FIG. 7). This time frame is consistent with expectations as it typically takes at least 10 to 14 days for RAMA responses to reach significant levels, and this is confirmed by the data in FIG. 5. Strong tetramer responses are generally associated with low or delayed levels of RAMAs.

Summary: The enhancement of adenovirus vector-induced T cell responses by PD-1 blockade was observed, although the uniformity was limited by the small group size and intrinsic variability of immune responses. However, the enhancement by PD-1 blockade could be observed, and was statistically significant at day 10 post treatment in mouse IgG-naïve monkeys (comparing groups 1+2 vs. groups 3+4). The delay of RAMA can prolong the period of effective PD-1 blockade and greatly enhance T-cell proliferation.

EXAMPLE 9

In Vitro Demonstration of PD-1-Specific Immunomodulation

Figure 6A:
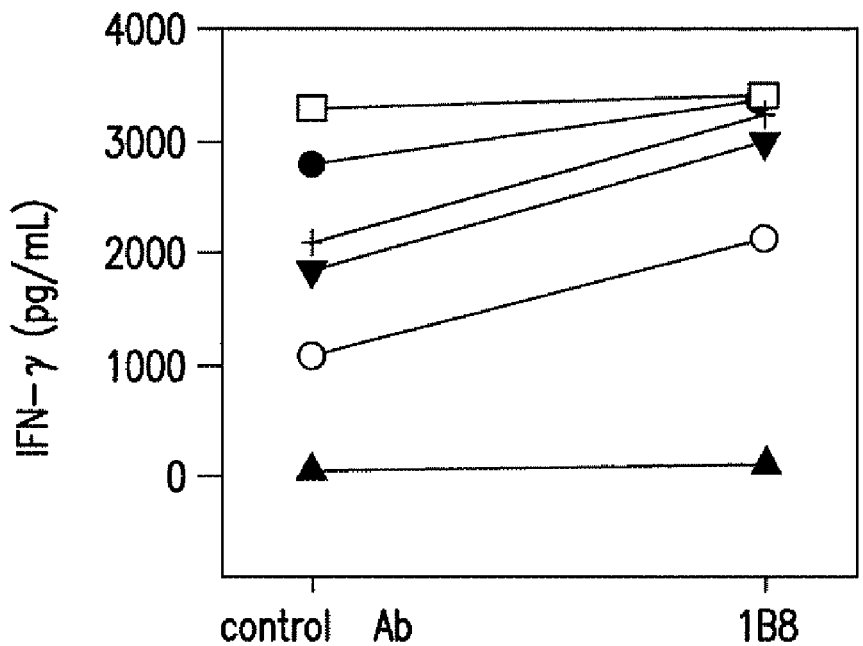
FIG. 6 shows concentration of IFN-γ (A) and IL-10 (B) in supernatants of peripheral blood mononuclear cell ("PBMCs") collected from human subjects who had received tetanus toxoid booster vaccinations. The PBMCs were cultured with tetanus toxoid in the presence of either anti-PD-1 monoclonal antibody, mAb 1B8 ("1B8"), or an isotype-matched control IgG ("Ctrl Ab"). Lines connect samples from the same subject.
Figure 6B:
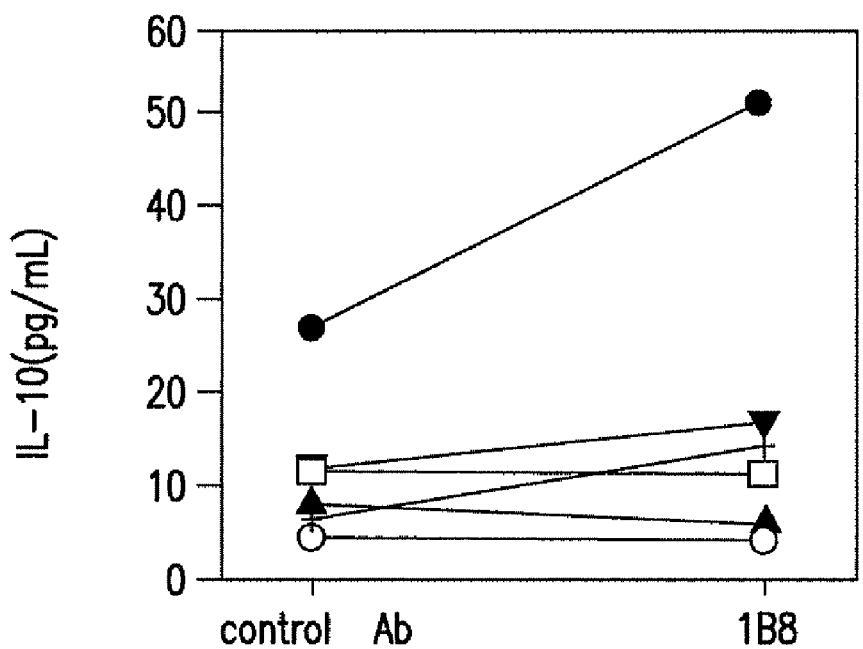

Six human volunteers received tetanus toxoid booster vaccinations. Some weeks later, peripheral blood mononuclear cells ("PBMCs") from these volunteers were isolated and cultured with 0.5 μg/mL tetanus toxoid in the presence of 20 μg/mL mouse IgG (either mAb 1B8 or an isotype-matched control IgG). Supernatants were collected 3 days later and concentrations of IFN-γ and IL-10 were measured by quantitative ELISA (FIGS. 6A and 6B, respectively). The lines in FIG. 6 connect samples from the same subject. IFN-γ was significantly enhanced by co-incubation with mAb 1B8 (p=0.023, paired two-tailed t-test). IL-10 was increased in cells from one volunteer, but otherwise not significantly enhanced by mAb 1B8 (p=0.22). Given the small sample sizes, it is more appropriate to use a non-parametric test. The conclusions are unchanged: in this case, IFN-γ was significantly enhanced by co-incubation with mAb 1B8 (p=0.031, paired Wilcoxon signed rank two-sided test). IL-10 was increased in cells from one volunteer, but otherwise not significantly enhanced by mAb 1B8 (p=0.44, paired Wilcoxon signed rank two-sided test).

These data demonstrate PD-1-specific cytokine production in vitro, a functional indication of antagonism of PD-1 signaling (i.e., blocking/attenuating PD-1 inhibitory signaling).

EXAMPLE 10

MAb 1B8 Chimeric Antibody Production

The variable regions for mAb 1B8 were cloned from the mouse hybridoma as described in Example 4, supra. The sequences for the variable regions were PCR amplified and DNA encoding the heavy chain variable regions were fused in-frame with DNA encoding either the human IgG1 constant region or the human IgG2m4 constant region (see U.S. Patent Publication no. US 2007/0148167). DNA encoding the mAb 1B8 light chain variable region was fused in-frame with DNA encoding the human kappa constant region. The chimeric 1B8-human IgG1 and chimeric 1B8-human IgG2m4 share this same light chain. The amino acid sequences (with the variable domains underlined) as deduced from the encoded DNA sequences are as follows:

```
Murine mAb 1B8 variable domain and human
kappa constant region amino acid sequence
(SEQ ID NO: AA):
    1 DIVLTQSPTS LAVSLGQRAT ISCRASESVD NSGISFMNWF
      QQKPGQPPKL
   51 LIYAASNPGS GVPARFSGSG SGTDFSLNIH PMEEDDTAMY
      FCQQSKEVPW
  101 TFGGGTELEI KRTVAAPSVF IFPPSDEQLK SGTASVVCLL
      NNFYPREAKV
  151 QWKVDNALQS GNSQESVTEQ DSKDSTYSLS STLTLSKADY
      EKHKVYACEV
  201 THQGLSSPVT KSFNRGEC Murine mAb 1B8 variable domain and human
IgG1 constant region amino acid sequence
(SEQ ID NO: BB):
    1 EVQLVLSGGG FVQPGGSLKL SCAASGFTFS SYAMSWVRQN
      PERRLVWVAT
   51 ITGGGRNTYY PDSVKGRFTI SRDNAKNTLY LQMSSLRSED
      TAMYYCTRQG
  101 YDGYTWFAYW GQGTLVTVSA ASTKGPSVFP LAPSSKSTSG
      GTAALGCLVK
  151 DYFPEPVTVS WNSGALTSGV HTFPAVLQSS GLYSLSSVVT
      VPSSSLGTQT
  201 YICNVNHKPS NTKVDKKVEP KSCDKTHTCP PCPAPELLGG
      PSVFLFPPKP
  251 KDTLMISRTP EVTCVVVDVS HEDPEVKFNW YVDGVEVHNA
      KTKPREEQYN
  301 STYRVVSVLT VLHQDWLNGK EYKCKVSNKA LPAPIEKTIS
      KAKGQPREPQ
  351 VYTLPPSRDE LTKNQVSLTC LVKGFYPSDI AVEWESNGQP
      ENNYKTTPPV
  401 LDSDGSFFLY SKLTVDKSRW QQGNVFSCSV MHEALHNHYT
      QKSLSLSPGK Murine mAb 1B8 variable domain and human
IgG2m4 constant region amino acid sequence
(SEQ ID NO: CC):
    1 EVQLVLSGGG FVQPGGSLKL SCAASGFTFS SYAMSWVRQN
      PERRLVWVAT
   51 ITGGGRNTYY PDSVKGRFTI SRDNAKNTLY LQMSSLRSED
      TAMYYCTRQG
  101 YDGYTWFAYW GQGTLVTVSA ASTKGPSVFP LAPCSRSTSE
      STAALGCLVK
  151 DYFPEPVTVS WNSGALTSGV HTFPAVLQSS GLYSLSSVVT
      VTSSNFGTQT
  201 YTCNVDHKPS NTKVDKTVER KCCVECPPCP APPVAGPSVF
      LFPPKPKDTL
  251 MISRTPEVTC VVVDVSQEDP EVQFNWYVDG VEVHNAKTKP
      REEQFNSTFR
  301 VVSVLTVLHQ DWLNGKEYKC KVSNKGLPSS IEKTISKTKG
      QPREPQVYTL
  351 PPSREEMTKN QVSLTCLVKG FYPSDIAVEW ESNGQPENNY
      KTTPPMLDSD
  401 GSFFLYSKLT VDKSRWQQGN VFSCSVMHEA LHNHYTQKSL
      SLSPGK
```

A competitive ELISA assay was performed to evaluate the relative binding of the versions of 1B8 mAb. A 96-well microtiter plate was coated with 10 ng/mL recombinant human PD-1/Fc (R&D Systems) and incubated for one hour, washed, incubated with blocking buffer for one hour, and incubated with a mixture of 10 ng/mL biotinylated murine 1B8 and varying concentrations of either fully murine 1B8 mAb, chimeric 1B8/human IgG1 constant region mAb, or chimeric 1B8/human IgG2m4 constant region mAb. All wells were washed, incubated with strepavidin for 30 minutes, and developed with 10-Acetyl-3,7-dihydroxyphenoxazine (ADHP) for 3 minutes before being measured on a fluorescence plate reader. All incubations occurred at room temperature. Data were fit to a standard four-point sigmoidal model, including effective concentrations at 50% (EC50) parameters. Results demonstrate that each 1B8 form competed with biotinylated murine 1B8 for binding to PD-1. Relative EC50 values (in arbitrary units) were 031±0.03 for murine 1B8, 0.27±0.02 for 1B8 with human IgG1 constant region, and 0.824±0.004 for 1B8 with human IgG2m4 constant region.

What is claimed is:

1. An isolated PD-1 binding protein comprising a first variable region and a second variable region, wherein said binding protein specifically binds a human PD-1 epitope contained within a PD-L1-blocking target region, wherein said first variable region is a heavy chain variable ($V_h$) region comprising:
- a first $V_h$ CDR comprising either SEQ ID NO:6 or an amino acid sequence differing from SEQ ID NOs:6 by one amino acid;
- a second $V_h$ CDR comprising either SEQ ID NO:7 or an amino acid sequence differing from SEQ ID NOs:7 by one amino acid; and,
- a third $V_h$ CDR comprising either SEQ ID NO:8 or an amino acid sequence differing from SEQ ID NOs:8 by one amino acid.

2. The binding protein of claim 1, wherein said second variable region is a light chain variable ($V_l$) region comprising:
- a first $V_l$ CDR comprising either SEQ ID NO:9 or an amino acid sequence differing from SEQ ID NOs:9 by one amino acid;
- a second $V_l$ CDR comprising either SEQ ID NO:10 or an amino acid sequence differing from SEQ ID NOs:10 by one amino; and
- a third $V_l$ CDR comprising either SEQ ID NO:11 or an amino acid sequence differing from SEQ ID NOs:11— by one amino acid.

3. The binding protein of claim 1, wherein
said $V_h$ region comprises said first $V_h$ CDR consisting of SEQ ID NO:6, said second $V_h$ CDR consisting of SEQ ID NO:7, and said third $V_h$ CDR consisting of SEQ ID NO:8; and,
said $V_l$ region comprises said first $V_l$ CDR consisting of SEQ ID NO:9, said second $V_l$ CDR consisting of SEQ ID NO:10, and said third $V_l$ CDR consisting of SEQ ID NO:11.

4. The binding protein of claim 3, wherein said binding protein is an antibody.

5. The binding protein of claim 1, wherein said binding protein is an antibody comprising a first variable region which is a heavy chain variable ($V_h$) region and a second variable region which is a light chain variable ($V_l$) region, and wherein said $V_h$ region comprises: SEQ ID NO:4 or a humanized SEQ ID NO:4.

6. The binding protein of claim 5, wherein said $V_h$ region comprises SEQ ID NO:4.

7. The binding protein of claim 5, wherein said $V_l$ region comprises SEQ ID NO:5.

8. The binding protein of claim 5, wherein said binding protein is an antibody and said antibody comprises a heavy chain comprising said $V_h$ region and hinge, $CH_1$, $CH_2$ and $CH_3$ regions from an $IgG_1$, $IgG_2$, $IgG_3$ or $IgG_4$ subtype; and a light chain comprising said $V_l$ region and either a human kappa $C_l$ or human lambda $C_l$.

9. A pharmaceutical composition comprising the a PD-1 binding protein of claim 1 and a pharmaceutically acceptable carrier.

10. The binding protein of claim 1, wherein said binding protein is an antibody comprising a first variable region which is a heavy chain variable ($V_h$) region and a second variable region which is a light chain variable ($V_l$) region, and wherein said $V_l$ region comprises SEQ ID NO:5 or a humanized SEQ ID NO:5.

11. The binding protein of claim 10, wherein said $V_l$ region comprises SEQ ID NO:5.

12. The binding protein of claim 10, wherein said $V_h$ region comprises SEQ ID NO:4.

13. The binding protein of claim 5, wherein said $V_h$ region comprises SEQ ID NO:4 and said $V_l$ region comprises SEQ ID NO:5.

14. The binding protein of claim 10, wherein said binding protein is an antibody and said antibody comprises a heavy chain comprising said $V_h$ region and hinge, $CH_1$, $CH_2$ and $CH_3$ regions from an $IgG_1$, $IgG_2$, $IgG_3$ or $IgG_4$ subtype; and a light chain comprising said $V_l$ region and either a human kappa $C_l$ or human lambda $C_l$.

15. An isolated PD-1 binding protein comprising a first variable region and a second variable region, wherein said binding protein specifically binds a human PD-1 epitope contained within a PD-L1-blocking target region wherein said first variable region is a light chain variable ($V_l$) region comprising
- a first $V_l$ CDR comprising either SEQ ID NO:9 or an amino acid sequence differing from SEQ ID NOs:9 by one amino acid;

a second $V_l$ CDR comprising either SEQ ID NO:10 or an amino acid sequence differing from SEQ ID NOs:10 by one amino acid; and, a third $V_l$ CDR comprising either SEQ ID NO:11 or an amino acid sequence differing from SEQ ID NOs:8 by one amino acid.

16. A pharmaceutical composition comprising the a PD-1 binding protein of claim 15 and a pharmaceutically acceptable carrier.

17. An isolated PD-1 binding protein comprising a first variable region and a second variable region, wherein said binding protein specifically binds a human PD-1 epitope contained within a PD-L1-blocking target region, wherein said first variable region is a heavy chain variable ($V_h$) region of SEQ ID NO:4 and said second variable region is a light chain variable ($V_l$) region of SEQ ID NO:5.

18. A pharmaceutical composition comprising the a PD-1 binding protein of claim 17 and a pharmaceutically acceptable carrier.

19. A pharmaceutical composition comprising the a PD-1 binding protein of claim 3 and a pharmaceutically acceptable carrier.

\* \* \* \* \*

```
                           SEQUENCE LISTING

<160> NUMBER OF SEQ ID NOS: 77

<210> SEQ ID NO 1
<211> LENGTH: 288
<212> TYPE: PRT
<213> ORGANISM: Homo sapien

<400> SEQUENCE: 1

Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 2
<211> LENGTH: 290
<212> TYPE: PRT
<213> ORGANISM: Homo sapien

<400> SEQUENCE: 2

Met Arg Ile Phe Ala Val Phe Ile Phe Met Thr Tyr Trp His Leu Leu
 1               5                  10                  15
```

```
Asn Ala Phe Thr Val Thr Val Pro Lys Asp Leu Tyr Val Val Glu Tyr
             20                  25                  30
Gly Ser Asn Met Thr Ile Glu Cys Lys Phe Pro Val Glu Lys Gln Leu
         35                  40                  45
Asp Leu Ala Ala Leu Ile Val Tyr Trp Glu Met Glu Asp Lys Asn Ile
 50                  55                  60
Ile Gln Phe Val His Gly Glu Asp Leu Lys Val Gln His Ser Ser
 65                  70                  75                  80
Tyr Arg Gln Arg Ala Arg Leu Leu Lys Asp Gln Leu Ser Leu Gly Asn
                 85                  90                  95
Ala Ala Leu Gln Ile Thr Asp Val Lys Leu Gln Asp Ala Gly Val Tyr
            100                 105                 110
Arg Cys Met Ile Ser Tyr Gly Gly Ala Asp Tyr Lys Arg Ile Thr Val
        115                 120                 125
Lys Val Asn Ala Pro Tyr Asn Lys Ile Asn Gln Arg Ile Leu Val Val
130                 135                 140
Asp Pro Val Thr Ser Glu His Glu Leu Thr Cys Gln Ala Glu Gly Tyr
145                 150                 155                 160
Pro Lys Ala Glu Val Ile Trp Thr Ser Ser Asp His Gln Val Leu Ser
                165                 170                 175
Gly Lys Thr Thr Thr Thr Asn Ser Lys Arg Glu Glu Lys Leu Phe Asn
            180                 185                 190
Val Thr Ser Thr Leu Arg Ile Asn Thr Thr Asn Glu Ile Phe Tyr
        195                 200                 205
Cys Thr Phe Arg Arg Leu Asp Pro Glu Glu Asn His Thr Ala Glu Leu
210                 215                 220
Val Ile Pro Glu Leu Pro Leu Ala His Pro Pro Asn Glu Arg Thr His
225                 230                 235                 240
Leu Val Ile Leu Gly Ala Ile Leu Leu Cys Leu Gly Val Ala Leu Thr
                245                 250                 255
Phe Ile Phe Arg Leu Arg Lys Gly Arg Met Met Asp Val Lys Lys Cys
            260                 265                 270
Gly Ile Gln Asp Thr Asn Ser Lys Lys Gln Ser Asp Thr His Leu Glu
        275                 280                 285
Glu Thr
    290

<210> SEQ ID NO 3
<211> LENGTH: 4867
<212> TYPE: DNA
<213> ORGANISM: Artificial Sequence
<220> FEATURE:
<223> OTHER INFORMATION: V1Jns

<400> SEQUENCE: 3
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctggc ttaactatg cggcatcaga gcagattgta ctgagagtgc      180
accatatgcg gtgtgaaata ccgcacagat gcgtaaggag aaaataccgc atcagattgg     240
ctattggcca ttgcatacgt tgtatccata tcataatatg tacatttata ttggctcatg    300
tccaacatta ccgccatgtt gacattgatt attgactagt tattaatagt aatcaattac    360
ggggtcatta gttcatagcc catatatgga gttccgcgtt acataactta cggtaaatgg    420
cccgcctggc tgaccgccca acgacccccg cccattgacg tcaataatga cgtatgttcc    480
```

```
catagtaacg ccaataggga cttttccattg acgtcaatgg gtggagtatt tacggtaaac    540
tgcccacttg gcagtacatc aagtgtatca tatgccaagt acgcccccta ttgacgtcaa    600
tgacggtaaa tggcccgcct ggcattatgc ccagtacatg accttatggg actttcctac    660
ttggcagtac atctacgtat tagtcatcgc tattaccatg gtgatgcggt tttggcagta    720
catcaatggg cgtggatagc ggtttgactc acggggattt ccaagtctcc accccattga    780
cgtcaatggg agtttgtttt ggcaccaaaa tcaacgggac tttccaaaat gtcgtaacaa    840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat   1020
tccccgtgcc aagagtgacg taagtaccgc ctatagactc tataggcaca cccctttggc   1080
tcttatgcat gctatactgt ttttggcttg ggcctatac accccgctt ccttatgcta    1140
taggtgatgg tatagcttag cctataggtg tgggttattg accattattg accactcccc   1200
tattggtgac gatactttcc attactaatc cataacatgg ctctttgcca caactatctc   1260
tattggctat atgccaatac tctgtccttc agagactgac acggactctg tatttttaca   1320
ggatggggtc ccatttatta tttacaaatt cacatataca acaacgccgt cccccgtgcc   1380
cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac   1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc   1740
gttgcggtgc tgttaacggt ggagggcagt gtagtctgag cagtactcgt tgctgccgcg   1800
cgcgccacca gacataatag ctgacagact aacagactgt tcctttccat gggtcttttc   1860
tgcagtcacc gtccttagat ctgctgtgcc ttctagttgc cagccatctg ttgtttgccc   1920
ctcccccgtg ccttccttga ccctggaagg tgccactccc actgtccttt cctaataaaa   1980
tgaggaaatt gcatcgcatt gtctgagtag gtgtcattct attctggggg gtggggtggg   2040
gcaggacagc aagggggagg attgggaaga caatagcagg catgctgggg atgcggtggg   2100
ctctatggcc gctgcggcca ggtgctgaag aattgacccg gttcctcctg ggccagaaag   2160
aagcaggcac atcccttct ctgtgacaca ccctgtccac gcccctggtt cttagttcca   2220
gccccactca taggacactc atagctcagg agggctccgc cttcaatccc acccgctaaa   2280
gtacttggag cggtctctcc ctccctcatc agcccaccaa accaaaccta gcctccaaga   2340
gtgggaagaa attaaagcaa gataggctat taagtgcaga gggagagaaa atgcctccaa   2400
catgtgagga agtaatgaga gaaatcatag aatttcttcc gcttcctcgc tcactgactc   2460
gctgcgctcg gtcgttcggc tgcggcgagc ggtatcagct cactcaaagg cggtaatacg   2520
gttatccaca gaatcagggg ataacgcagg aaagaacatg tgagcaaaag gccagcaaaa   2580
ggccaggaac cgtaaaaagg ccgcgttgct ggcgtttttc cataggctcc gcccccctga   2640
cgagcatcac aaaaatcgac gctcaagtca gaggtggcga aacccgacag gactataaag   2700
ataccaggcg tttccccctg gaagctccct cgtgcgctct cctgttccga ccctgccgct   2760
taccggatac ctgtccgcct ttctcccttc gggaagcgtg cgctttctc atagctcacg   2820
ctgtaggtat ctcagttcgg tgtaggtcgt tcgctccaag ctgggctgtg tgcacgaacc   2880
```

```
cccgttcag cccgaccgct gcgccttatc cggtaactat cgtcttgagt ccaacccggt    2940 aagcacgac ttatcgccac tggcagcagc cactggtaac aggattagca gagcgaggta    3000
tgtaggcggt gctacagagt tcttgaagtg gtggcctaac tacggctaca ctagaagaac    3060
agtatttggt atctgcgctc tgctgaagcc agttaccttc ggaaaaagag ttggtagctc    3120
ttgatccggc aaacaaacca ccgctggtag cggtggtttt tttgtttgca agcagcagat    3180
tacgcgcaga aaaaaggat ctcaagaaga tcctttgatc ttttctacgg ggtctgacgc    3240
tcagtggaac gaaaactcac gttaagggat tttggtcatg agattatcaa aaaggatctt    3300
cacctagatc cttttaaatt aaaaatgaag ttttaaatca atctaaagta tatatgagta    3360
aacttggtct gacagttacc aatgcttaat cagtgaggca cctatctcag cgatctgtct    3420
atttcgttca tccatagttg cctgactcgg ggggggggg cgctgaggtc tgcctcgtga    3480
agaaggtgtt gctgactcat accaggcctg aatcgcccca tcatccagcc agaaagtgag    3540
ggagccacgg ttgatgagag ctttgttgta gtggaccag ttggtgattt tgaactttg    3600 ctttgccacg gaacggtctg cgttgtcggg aagatgcgtg atctgatcct tcaactcagc    3660
aaaagttcga tttattcaac aaagccgccg tcccgtcaag tcagcgtaat gctctgccag    3720
tgttacaacc aattaaccaa ttctgattag aaaaactcat cgagcatcaa atgaaactgc    3780
aatttattca tatcaggatt atcaataca tattttgaa aaagccgttt ctgtaatgaa    3840
ggagaaaact caccgaggca gttccatagg atggcaagat cctggtatcg gtctgcgatt    3900
ccgactcgtc caacatcaat acaacctatt aatttcccct cgtcaaaaat aaggttatca    3960
agtgagaaat caccatgagt gacgactgaa tccggtgaga atggcaaaag cttatgcatt    4020
tctttccaga cttgttcaac aggccagcca ttacgctcgt catcaaaatc actcgcatca    4080
accaaaccgt tattcattcg tgattgcgcc tgagcgagac gaaatacgcg atcgctgtta    4140
aaaggacaat tacaaacagg aatcgaatgc aaccggcgca ggaacactgc cagcgcatca    4200
acaatatttt cacctgaatc aggatattct tctaataacct ggaatgctgt tttcccgggg    4260
atcgcagtgg tgagtaacca tgcatcatca ggagtacgga taaaatgctt gatggtcgga    4320
agaggcataa attccgtcag ccagtttagt ctgaccatct catctgtaac atcattggca    4380 acgctaccctt tgccatgttt cagaaacaac tctggcgcat cgggcttccc atacaatcga    4440
tagattgtcg cacctgattg cccgacatta tcgcgagccc atttatacccc atataaatca    4500 gcatccatgt tggaatttaa tcgcggcctc gagcaagacg tttccccgttg aatatggctc    4560 ataacacccc ttgtattact gtttatgtaa gcagacagtt ttattgttca tgatgatata    4620
tttttatctt gtgcaatgta acatcagaga ttttgagaca caacgtggct tccccccccc    4680
ccccattatt gaagcattta tcagggttat tgtctcatga gcggatacat atttgaatgt    4740
atttagaaaa ataaacaaat aggggttccg cgcacatttc cccgaaaagt gccacctgac    4800
gtctaagaaa ccattattat catgacatta acctataaaa ataggcgtat cacgaggccc    4860
tttcgtc                                                              4867
```

<210> SEQ ID NO 4
<211> LENGTH: 119
<212> TYPE: PRT
<213> ORGANISM: Artificial Sequence
<220> FEATURE:
<223> OTHER INFORMATION: mAb 1B8 Vh

<400> SEQUENCE: 4

Glu Val Gln Leu Val Leu Ser Gly Gly Gly Phe Val Gln Pro Gly Gly
 1               5                  10                  15

```
Ser Leu Lys Leu Ser Cys Ala Ala Ser Gly Phe Thr Phe Ser Tyr
            20                  25                  30

Ala Met Ser Trp Val Arg Gln Asn Pro Glu Arg Arg Leu Trp Val
            35                  40                  45

Ala Thr Ile Thr Gly Gly Gly Arg Asn Thr Tyr Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Thr Arg Gln Gly Tyr Asp Gly Tyr Thr Trp Phe Ala Tyr Trp Gly Gln
                100                 105                 110

Gly Thr Leu Val Thr Val Ser
            115

<210> SEQ ID NO 5
<211> LENGTH: 112
<212> TYPE: PRT
<213> ORGANISM: Artificial Sequence
<220> FEATURE:
<223> OTHER INFORMATION: mAb 1B8 V1

<400> SEQUENCE: 5

Asp Ile Val Leu Thr Gln Ser Pro Thr Ser Leu Ala Val Ser Leu Gly
1               5                   10                  15

Gln Arg Ala Thr Ile Ser Cys Arg Ala Ser Glu Ser Val Asp Asn Ser
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Pro Gly Ser Gly Val Pro Ala
50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Glu Leu Glu Ile Lys Arg
                100                 105                 110

<210> SEQ ID NO 6
<211> LENGTH: 13
<212> TYPE: PRT
<213> ORGANISM: Artificial Sequence
<220> FEATURE:
<223> OTHER INFORMATION: mAb 1B8 Vh CDR1

<400> SEQUENCE: 6

Ala Ala Ser Gly Phe Thr Phe Ser Ser Tyr Ala Met Ser
1               5                   10

<210> SEQ ID NO 7
<211> LENGTH: 17
<212> TYPE: PRT
<213> ORGANISM: Artificial Sequence
<220> FEATURE:
<223> OTHER INFORMATION: mAb 1B8 Vh CDR2

<400> SEQUENCE: 7

Thr Ile Thr Gly Gly Gly Arg Asn Thr Tyr Tyr Pro Asp Ser Val Lys
1               5                   10                  15

Gly
```

<210> SEQ ID NO 8
<211> LENGTH: 11
<212> TYPE: PRT
<213> ORGANISM: Artificial Sequence
<220> FEATURE:
<223> OTHER INFORMATION: mAb 1B8 Vh CDR3

<400> SEQUENCE: 8

Gln Gly Tyr Asp Gly Tyr Thr Trp Phe Ala Tyr
1               5                   10

<210> SEQ ID NO 9
<211> LENGTH: 15
<212> TYPE: PRT
<213> ORGANISM: Artificial Sequence
<220> FEATURE:
<223> OTHER INFORMATION: mAb 1B8 and 20B3.1 Vl CDR1

<400> SEQUENCE: 9

Arg Ala Ser Glu Ser Val Asp Asn Ser Gly Ile Ser Phe Met Asn
1               5                   10                  15

<210> SEQ ID NO 10
<211> LENGTH: 7
<212> TYPE: PRT
<213> ORGANISM: Artificial Sequence
<220> FEATURE:
<223> OTHER INFORMATION: mAb 1B8 Vl CDR2

<400> SEQUENCE: 10

Ala Ala Ser Asn Pro Gly Ser
1               5

<210> SEQ ID NO 11
<211> LENGTH: 9
<212> TYPE: PRT
<213> ORGANISM: Artificial Sequence
<220> FEATURE:
<223> OTHER INFORMATION: mAb 1B8 and 20B3.1 Vl CDR3

<400> SEQUENCE: 11

Gln Gln Ser Lys Glu Val Pro Trp Thr
1               5

<210> SEQ ID NO 12
<211> LENGTH: 117
<212> TYPE: PRT
<213> ORGANISM: Artificial Sequence
<220> FEATURE:
<223> OTHER INFORMATION: mAb 20B3.1 Vh

<400> SEQUENCE: 12

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Phe
                20                  25                  30

Gly Met Ser Trp Val Arg Gln Thr Pro Glu Lys Arg Leu Glu Trp Val
            35                  40                  45

Ala Thr Ile Ser Gly Gly Gly Ser Asn Thr Tyr Tyr Pro Asp Ser Val
        50                  55                  60

Lys Gly Arg Phe Thr Ile Ser Arg Asp Asn Ala Lys Asn Asn Leu Tyr
65                  70                  75                  80

Leu Gln Met Thr Ser Leu Thr Ser Glu Asp Thr Ala Leu Tyr Tyr Cys
                85                  90                  95

```
Thr Arg Ile Tyr Asp Val Ala Trp Phe Ala Tyr Trp Gly Gln Gly Thr
            100                 105                 110
Leu Val Thr Val Ser
        115

<210> SEQ ID NO 13
<211> LENGTH: 112
<212> TYPE: PRT
<213> ORGANISM: Artificial Sequence
<220> FEATURE:
<223> OTHER INFORMATION: mAb 20B3.1 Vl

<400> SEQUENCE: 13

Asp Ile Val Leu Thr Gln Ser Pro Ala Ser Leu Ala Val Ser Leu Gly
  1               5                  10                  15

Gln Arg Ala Thr Ile Ser Cys Arg Ala Ser Glu Ser Val Asp Asn Ser
             20                  25                  30

Gly Ile Ser Phe Met Asn Trp Phe Gln Gln Lys Pro Gly Gln Pro Pro
         35                  40                  45

Lys Leu Leu Ile Tyr Ala Ala Ser Asn Gln Gly Ser Gly Val Pro Ala
     50                  55                  60

Arg Phe Ser Gly Ser Gly Ser Gly Thr Asp Phe Ser Leu Asn Ile His
 65                  70                  75                  80

Pro Met Glu Glu Asp Asp Thr Ala Met Tyr Phe Cys Gln Gln Ser Lys
                 85                  90                  95

Glu Val Pro Trp Thr Phe Gly Gly Gly Thr Lys Leu Glu Ile Lys Arg
            100                 105                 110

<210> SEQ ID NO 14
<211> LENGTH: 13
<212> TYPE: PRT
<213> ORGANISM: Artificial Sequence
<220> FEATURE:
<223> OTHER INFORMATION: mAb 20B3.1 Vh CDR1

<400> SEQUENCE: 14

Ala Ala Ser Gly Phe Thr Phe Ser Ser Phe Gly Met Ser
  1               5                  10

<210> SEQ ID NO 15
<211> LENGTH: 17
<212> TYPE: PRT
<213> ORGANISM: Artificial Sequence
<220> FEATURE:
<223> OTHER INFORMATION: mAb 20B3.1 Vh CDR2

<400> SEQUENCE: 15

Thr Ile Ser Gly Gly Gly Ser Asn Thr Tyr Tyr Pro Asp Ser Val Lys
  1               5                  10                  15

Gly

<210> SEQ ID NO 16
<211> LENGTH: 9
<212> TYPE: PRT
<213> ORGANISM: Artificial Sequence
<220> FEATURE:
<223> OTHER INFORMATION: mAb 20B3.1 Vh CDR3

<400> SEQUENCE: 16

Ile Tyr Asp Val Ala Trp Phe Ala Tyr
  1               5
```

```
<210> SEQ ID NO 17
<211> LENGTH: 7
<212> TYPE: PRT
<213> ORGANISM: Artificial Sequence
<220> FEATURE:
<223> OTHER INFORMATION: mAb 20B3.1 Vl CDR2

<400> SEQUENCE: 17

Ala Ala Ser Asn Gln Gly Ser
 1               5

<210> SEQ ID NO 18
<211> LENGTH: 119
<212> TYPE: PRT
<213> ORGANISM: Artificial Sequence
<220> FEATURE:
<223> OTHER INFORMATION: mAb 7G3 Vh

<400> SEQUENCE: 18

Gln Val Gln Leu Gln Gln Ser Gly Thr Glu Leu Val Arg Pro Gly Val
 1               5                  10                  15

Ser Val Lys Ile Ser Cys Lys Gly Ser Gly Tyr Ser Phe Thr Asp Tyr
             20                  25                  30

Ala Leu His Trp Met Lys Gln Ser His Ala Lys Ser Leu Glu Trp Ile
         35                  40                  45

Gly Val Ile Ser Thr His Tyr Gly Asp Thr Val Tyr Asn Gln Arg Phe
     50                  55                  60

Lys Gly Lys Ala Thr Met Thr Val Asp Lys Ser Ser Thr Ala Tyr
 65                  70                  75                  80

Met Glu Leu Ala Arg Leu Thr Ser Glu Asp Ser Ala Ile Tyr Tyr Cys
                 85                  90                  95

Ala Arg Glu Gly Tyr Gly Ser Leu Phe Tyr Phe Asp Trp Gly Gln
            100                 105                 110

Gly Thr Pro Leu Thr Val Ser
        115

<210> SEQ ID NO 19
<211> LENGTH: 112
<212> TYPE: PRT
<213> ORGANISM: Artificial Sequence
<220> FEATURE:
<223> OTHER INFORMATION: mAb 7G3 Vl

<400> SEQUENCE: 19

Cys Leu Met Thr Gln Thr Pro Leu Ser Leu Pro Val Ser Leu Gly Asp
 1               5                  10                  15

Gln Ala Ser Ile Ser Cys Arg Ser Ser Gln Thr Ile Val His Ser Asp
             20                  25                  30

Gly Asn Thr Tyr Leu Glu Trp Tyr Leu Gln Lys Ser Gly Gln Ser Pro
         35                  40                  45

Lys Leu Leu Ile Tyr Lys Val Ser Asn Arg Phe Ser Gly Val Pro Asp
     50                  55                  60

Arg Phe Ser Gly Ser Gly Ser Gly Thr Asp Phe Thr Leu Lys Ile Ser
 65                  70                  75                  80

Arg Val Glu Ala Glu Asp Leu Gly Val Tyr Tyr Cys Phe Gln Gly Ser
                 85                  90                  95

His Val Pro Tyr Thr Phe Gly Gly Gly Thr Arg Leu Glu Ile Arg Arg
            100                 105                 110

<210> SEQ ID NO 20
<211> LENGTH: 13
```

-continued

```
<212> TYPE: PRT
<213> ORGANISM: Artificial Sequence
<220> FEATURE:
<223> OTHER INFORMATION: mAb 7G3 Vh CDR1

<400> SEQUENCE: 20

Lys Gly Ser Gly Tyr Ser Phe Thr Asp Tyr Ala Leu His
1               5                   10

<210> SEQ ID NO 21
<211> LENGTH: 17
<212> TYPE: PRT
<213> ORGANISM: Artificial Sequence
<220> FEATURE:
<223> OTHER INFORMATION: mAb 7G3 Vh CDR2

<400> SEQUENCE: 21

Val Ile Ser Thr His Tyr Gly Asp Thr Val Tyr Asn Gln Arg Phe Lys
1               5                   10                  15

Gly

<210> SEQ ID NO 22
<211> LENGTH: 11
<212> TYPE: PRT
<213> ORGANISM: Artificial Sequence
<220> FEATURE:
<223> OTHER INFORMATION: mAb 7G3 Vh CDR3

<400> SEQUENCE: 22

Glu Gly Tyr Gly Ser Leu Phe Tyr Phe Asp Gln
1               5                   10

<210> SEQ ID NO 23
<211> LENGTH: 16
<212> TYPE: PRT
<213> ORGANISM: Artificial Sequence
<220> FEATURE:
<223> OTHER INFORMATION: mAb 7G3 Vl CDR1

<400> SEQUENCE: 23

Arg Ser Ser Gln Thr Ile Val His Ser Asp Gly Asn Thr Tyr Leu Glu
1               5                   10                  15

<210> SEQ ID NO 24
<211> LENGTH: 7
<212> TYPE: PRT
<213> ORGANISM: Artificial Sequence
<220> FEATURE:
<223> OTHER INFORMATION: mAb 7G3, 1.8A10 and  28.11.1 Vl CDR2

<400> SEQUENCE: 24

Lys Val Ser Asn Arg Phe Ser
1               5

<210> SEQ ID NO 25
<211> LENGTH: 9
<212> TYPE: PRT
<213> ORGANISM: Artificial Sequence
<220> FEATURE:
<223> OTHER INFORMATION: mAb 7G3, and 1.8A10 Vl CDR3

<400> SEQUENCE: 25

Phe Gln Gly Ser His Val Pro Tyr Thr
1               5

<210> SEQ ID NO 26
<211> LENGTH: 118
```

```
<212> TYPE: PRT
<213> ORGANISM: Artificial Sequence
<220> FEATURE:
<223> OTHER INFORMATION: mAb 1G7 Vh

<400> SEQUENCE: 26

Glu Ile Gln Leu Gln Gln Ser Gly Pro Glu Leu Val Lys Pro Gly Ala
 1               5                  10                  15

Ser Val Lys Val Ser Cys Lys Ala Ser Gly Tyr Ala Phe Thr Ser Tyr
            20                  25                  30

Asn Ile Tyr Trp Val Lys Gln Ser His Gly Lys Ser Leu Glu Trp Ile
        35                  40                  45

Gly Tyr Ile Asp Leu Tyr Asn Gly Asp Thr Ser Tyr Asn Glu Lys Phe
    50                  55                  60

Lys Gly Lys Ala Thr Leu Thr Val Asp Lys Ser Ala Ser Thr Ala Tyr
65                  70                  75                  80

Met His Leu Asn Ser Leu Thr Ser Glu Asp Ser Ala Val Tyr Tyr Cys
                85                  90                  95

Ser Arg Glu Gly Arg Leu Ser Phe Asp Tyr Trp Gly Gln Gly Thr Leu
            100                 105                 110

Val Thr Val Ser Ala Ala
        115

<210> SEQ ID NO 27
<211> LENGTH: 112
<212> TYPE: PRT
<213> ORGANISM: Artificial Sequence
<220> FEATURE:
<223> OTHER INFORMATION: mAb 1G7 Vl

<400> SEQUENCE: 27

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
            20                  25                  30

Gly Asn Ser Phe Met Asn Trp Tyr Gln Gln Lys Pro Gly Gln Pro Leu
        35                  40                  45

Lys Leu Leu Ile Tyr Leu Ala Ser Asn Leu Asp Ser Gly Val Pro Ala
    50                  55                  60

Arg Phe Ser Gly Ser Gly Ser Gly Thr Asp Phe Ser Leu Thr Ile Asp
65                  70                  75                  80

Pro Val Glu Ala Asp Asp Pro Ala Thr Tyr Tyr Cys Gln Gln Asn Asn
                85                  90                  95

Glu Val Pro Leu Thr Phe Gly Ala Gly Thr Lys Leu Glu Leu Lys Arg
            100                 105                 110

<210> SEQ ID NO 28
<211> LENGTH: 13
<212> TYPE: PRT
<213> ORGANISM: Artificial Sequence
<220> FEATURE:
<223> OTHER INFORMATION: mAb 1G7 Vh CDR1

<400> SEQUENCE: 28

Lys Ala Ser Gly Tyr Ala Phe Thr Ser Tyr Asn Ile Tyr
 1               5                  10

<210> SEQ ID NO 29
<211> LENGTH: 15
<212> TYPE: PRT
<213> ORGANISM: Artificial Sequence
```

<220> FEATURE:
<223> OTHER INFORMATION: mAb 1G7 Vh CDR2

<400> SEQUENCE: 29

Tyr Ile Asp Leu Tyr Asn Gly Asp Thr Ser Tyr Asn Glu Lys Phe
1               5                   10                  15

<210> SEQ ID NO 30
<211> LENGTH: 8
<212> TYPE: PRT
<213> ORGANISM: Artificial Sequence
<220> FEATURE:
<223> OTHER INFORMATION: mAb 1G7 Vh CDR3

<400> SEQUENCE: 30

Glu Gly Arg Leu Ser Phe Asp Tyr
1               5

<210> SEQ ID NO 31
<211> LENGTH: 15
<212> TYPE: PRT
<213> ORGANISM: Artificial Sequence
<220> FEATURE:
<223> OTHER INFORMATION: mAb 1G7 Vl CDR1

<400> SEQUENCE: 31

Arg Ala Ser Glu Ser Val Asp Ser Tyr Gly Asn Ser Phe Met Asn
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: mAb 1G7 Vl CDR2

<400> SEQUENCE: 32

Leu Ala Ser Asn Leu Asp Ser
1               5

<210> SEQ ID NO 33
<211> LENGTH: 9
<212> TYPE: PRT
<213> ORGANISM: Artificial Sequence
<220> FEATURE:
<223> OTHER INFORMATION: mAb 1G7 Vl CDR3

<400> SEQUENCE: 33

Gln Gln Asn Asn Glu Val Pro Leu Thr
1               5

<210> SEQ ID NO 34
<211> LENGTH: 119
<212> TYPE: PRT
<213> ORGANISM: Artificial Sequence
<220> FEATURE:
<223> OTHER INFORMATION: mAb 1.8A10 Vh

<400> SEQUENCE: 34

Glu Val Gln Leu Val Glu Ser Gly Gly Gly Leu Val Lys Pro Gly
1               5                   10                  15

Ser Leu Lys Leu Ser Cys Ala Ala Ser Gly Phe Thr Phe Ser Asn Tyr
                20                  25                  30

Asp Met Ser Trp Ile Arg Gln Thr Pro Glu Lys Arg Leu Glu Trp Val
            35                  40                  45

Ala Tyr Ile Ser Gly Gly Gly Gly Asn Thr Tyr Tyr Pro Asp Thr Leu

```
                50                  55                  60
Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Phe Tyr Cys
                 85                  90                  95

Val Arg Ile Ser Leu Thr Gly Ile Phe Asp Tyr Trp Gly Gln Gly Thr
                100                 105                 110

Thr Leu Thr Val Ser Ser Ala
            115
```

<210> SEQ ID NO 35
<211> LENGTH: 113
<212> TYPE: PRT
<213> ORGANISM: Artificial Sequence
<220> FEATURE:
<223> OTHER INFORMATION: mAb 1.8A10 Vl

<400> SEQUENCE: 35

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val Gln Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Trp Thr Phe Gly Gly Gly Thr Lys Leu Glu Ile Lys
                100                 105                 110

Arg
```

<210> SEQ ID NO 36
<211> LENGTH: 13
<212> TYPE: PRT
<213> ORGANISM: Artificial Sequence
<220> FEATURE:
<223> OTHER INFORMATION: mAb 1.8A10 Vh CDR1

<400> SEQUENCE: 36

```
Ala Ala Ser Gly Phe Thr Phe Ser Asn Tyr Asp Met Ser
 1               5                  10
```

<210> SEQ ID NO 37
<211> LENGTH: 15
<212> TYPE: PRT
<213> ORGANISM: Artificial Sequence
<220> FEATURE:
<223> OTHER INFORMATION: mAb 1.8A10 Vh CDR2

<400> SEQUENCE: 37

```
Tyr Ile Ser Gly Gly Gly Gly Asn Thr Tyr Tyr Pro Asp Thr Leu
 1               5                  10                  15
```

<210> SEQ ID NO 38
<211> LENGTH: 9
<212> TYPE: PRT
<213> ORGANISM: Artificial Sequence
<220> FEATURE:
<223> OTHER INFORMATION: mAb 1.8A10 Vh CDR3

```
<400> SEQUENCE: 38

Ile Ser Leu Thr Gly Ile Phe Asp Tyr
1               5

<210> SEQ ID NO 39
<211> LENGTH: 16
<212> TYPE: PRT
<213> ORGANISM: Artificial Sequence
<220> FEATURE:
<223> OTHER INFORMATION: mAb 1.8A10 Vl CDR1

<400> SEQUENCE: 39

Arg Ser Ser Gln Ser Ile Val Gln Ser Asn Gly Asn Thr Tyr Leu Glu
1               5                   10                  15

<210> SEQ ID NO 40
<211> LENGTH: 119
<212> TYPE: PRT
<213> ORGANISM: Artificial Sequence
<220> FEATURE:
<223> OTHER INFORMATION: mAb 28.11.1 Vh

<400> SEQUENCE: 40

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Asn Ser Tyr
            20                  25                  30

Gly Met Ser Trp Val Arg Gln Thr Pro Asp Lys Arg Leu Glu Trp Val
        35                  40                  45

Ala Thr Ile Ser Gly Gly Gly Ser Tyr Thr Tyr Tyr Pro Asp Ser Val
    50                  55                  60

Gln Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Ser Gly Asn Tyr Val Tyr Val Met Asp Tyr Trp Gly Gln Gly Thr
            100                 105                 110

Ser Val Thr Val Ser Ser Ala
        115

<210> SEQ ID NO 41
<211> LENGTH: 113
<212> TYPE: PRT
<213> ORGANISM: Artificial Sequence
<220> FEATURE:
<223> OTHER INFORMATION: mAb 28.11.1 Vl

<400> SEQUENCE: 41

Asp Val Met Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Gly
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95
```

Ser His Val Pro Tyr Thr Phe Gly Gly Gly Thr Lys Leu Glu Ile Lys
            100                 105                 110

Arg

<210> SEQ ID NO 42
<211> LENGTH: 13
<212> TYPE: PRT
<213> ORGANISM: Artificial Sequence
<220> FEATURE:
<223> OTHER INFORMATION: mAb 28.11.1 Vh CDR1

<400> SEQUENCE: 42

Ala Ala Ser Gly Phe Thr Phe Asn Ser Tyr Gly Met Ser
1               5                   10

<210> SEQ ID NO 43
<211> LENGTH: 17
<212> TYPE: PRT
<213> ORGANISM: Artificial Sequence
<220> FEATURE:
<223> OTHER INFORMATION: mAb 28.11.1 Vh CDR2

<400> SEQUENCE: 43

Thr Ile Ser Gly Gly Gly Ser Tyr Thr Tyr Tyr Pro Asp Ser Val Gln
1               5                   10                  15

Gly

<210> SEQ ID NO 44
<211> LENGTH: 9
<212> TYPE: PRT
<213> ORGANISM: Artificial Sequence
<220> FEATURE:
<223> OTHER INFORMATION: mAb 28.11.1 Vh CDR3

<400> SEQUENCE: 44

Gly Asn Tyr Val Tyr Val Met Asp Tyr
1               5

<210> SEQ ID NO 45
<211> LENGTH: 16
<212> TYPE: PRT
<213> ORGANISM: Artificial Sequence
<220> FEATURE:
<223> OTHER INFORMATION: mAb 28.11.1 Vl CDR1

<400> SEQUENCE: 45

Arg Ser Ser Gln Thr Ile Val His Gly Asn Gly Asn Thr Tyr Leu Glu
1               5                   10                  15

<210> SEQ ID NO 46
<211> LENGTH: 9
<212> TYPE: PRT
<213> ORGANISM: Artificial Sequence
<220> FEATURE:
<223> OTHER INFORMATION: mAb 28.11.1 Vl CDR3

<400> SEQUENCE: 46

Phe Gln Gly Ser His Val Pro Tyr Thr
1               5

<210> SEQ ID NO 47
<211> LENGTH: 122
<212> TYPE: PRT
<213> ORGANISM: Artificial Sequence
<220> FEATURE:
<223> OTHER INFORMATION: mAb 28.11.2 Vh

```
<400> SEQUENCE: 47

Gln Val Gln Leu Gln Gln Ser Gly Pro Glu Leu Val Arg Pro Gly Val
1               5                   10                  15

Ser Val Lys Ile Ser Cys Lys Gly Ser Gly Tyr Ile Phe Thr Asp Tyr
            20                  25                  30

Val Met His Trp Val Lys Gln Ser Pro Ala Lys Ser Leu Glu Trp Ile
        35                  40                  45

Gly Val Ile Ser Thr Tyr Tyr Ser Asn Ile Asn Tyr Asn Gln Lys Phe
    50                  55                  60

Lys Gly Lys Ala Thr Met Thr Val Asp Lys Ser Ser Thr Ala Tyr
65                  70                  75                  80

Leu Glu Leu Ala Arg Leu Thr Ser Glu Asp Ser Ala Ile Tyr Phe Cys
                85                  90                  95

Ala Arg Glu Gly Phe Gly Arg Pro Tyr Trp Tyr Phe Asp Val Trp Gly
            100                 105                 110

Ala Gly Thr Thr Val Thr Val Ser Ser Ala
            115                 120

<210> SEQ ID NO 48
<211> LENGTH: 111
<212> TYPE: PRT
<213> ORGANISM: Artificial Sequence
<220> FEATURE:
<223> OTHER INFORMATION: mAb 28.11.2 Vl

<400> SEQUENCE: 48

Ala Tyr Gln Met Thr Gln Ser Pro Ser Ser Leu Ser Ala Ser Val Gly
1               5                   10                  15

Asp Arg Val Thr Ile Lys Cys Gln Ala Ser Glu Asn Ile Tyr Ser Ser
            20                  25                  30

Leu Ala Trp Tyr Gln Gln Lys Pro Gly Lys Pro Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly Phe Gly Thr Ser Asn
                85                  90                  95

Val Glu Asn Pro Phe Gly Gly Gly Thr Lys Val Glu Ile Lys Arg
            100                 105                 110

<210> SEQ ID NO 49
<211> LENGTH: 13
<212> TYPE: PRT
<213> ORGANISM: Artificial Sequence
<220> FEATURE:
<223> OTHER INFORMATION: mAb 28.11.2 Vh CDR1

<400> SEQUENCE: 49

Lys Gly Ser Gly Tyr Ile Phe Thr Asp Tyr Val Met His
1               5                   10

<210> SEQ ID NO 50
<211> LENGTH: 17
<212> TYPE: PRT
<213> ORGANISM: Artificial Sequence
<220> FEATURE:
<223> OTHER INFORMATION: mAb 28.11.2 Vh CDR2

<400> SEQUENCE: 50
```

Val Ile Ser Thr Tyr Tyr Ser Asn Ile Asn Tyr Asn Gln Lys Phe Lys
1               5                   10                  15

Gly

<210> SEQ ID NO 51
<211> LENGTH: 12
<212> TYPE: PRT
<213> ORGANISM: Artificial Sequence
<220> FEATURE:
<223> OTHER INFORMATION: mAb 28.11.2 Vh CDR3

<400> SEQUENCE: 51

Glu Gly Phe Gly Arg Pro Tyr Trp Tyr Phe Asp Val
1               5                   10

<210> SEQ ID NO 52
<211> LENGTH: 11
<212> TYPE: PRT
<213> ORGANISM: Artificial Sequence
<220> FEATURE:
<223> OTHER INFORMATION: mAb 28.11.2 Vl CDR1

<400> SEQUENCE: 52

Gln Ala Ser Glu Asn Ile Tyr Ser Ser Leu Ala
1               5                   10

<210> SEQ ID NO 53
<211> LENGTH: 7
<212> TYPE: PRT
<213> ORGANISM: Artificial Sequence
<220> FEATURE:
<223> OTHER INFORMATION: mAb 28.11.2 Vl CDR2

<400> SEQUENCE: 53

Ser Ala Ser Thr Leu Ala Ser
1               5

<210> SEQ ID NO 54
<211> LENGTH: 12
<212> TYPE: PRT
<213> ORGANISM: Artificial Sequence
<220> FEATURE:
<223> OTHER INFORMATION: mAb 28.11.2 Vl CDR3

<400> SEQUENCE: 54

Gln Gln Gly Phe Gly Thr Ser Asn Val Glu Asn Pro
1               5                   10

<210> SEQ ID NO 55
<211> LENGTH: 116
<212> TYPE: PRT
<213> ORGANISM: Artificial Sequence
<220> FEATURE:
<223> OTHER INFORMATION: mAb 3H4 Vh

<400> SEQUENCE: 55

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Tyr Ile Asn Trp Val Lys Gln Lys Pro Gly Gln Gly Leu Glu Trp Ile
            35                  40                  45

Gly Trp Ile Tyr Pro Gly Ser Val Asn Thr Lys Tyr Asn Glu Lys Phe
        50                  55                  60

Arg Gly Lys Ala Thr Leu Thr Val Asp Thr Ser Ser Thr Ala Tyr
65                  70                  75                  80

Ile Gln Leu Ser Gly Leu Thr Ser Glu Asp Thr Ala Val Tyr Phe Cys
                85                  90                  95

Ala Arg Tyr Ser Asn Trp Phe Phe Asp Val Trp Gly Ala Gly Thr Ala
            100                 105                 110

Val Thr Val Ser
        115

<210> SEQ ID NO 56
<211> LENGTH: 108
<212> TYPE: PRT
<213> ORGANISM: Artificial Sequence
<220> FEATURE:
<223> OTHER INFORMATION: mAb 3H4 Vl

<400> SEQUENCE: 56

Asp Ile Val Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
50                  55                  60

Ser Arg Ser Gly Ser Asp Tyr Ser Leu Ser Ile Ser Ser Leu Glu Ser
65                  70                  75                  80

Glu Asp Phe Ala Asp Tyr Tyr Cys Leu Gln Tyr Ala Ser Tyr Pro Tyr
                85                  90                  95

Thr Phe Gly Gly Gly Thr Lys Leu Glu Ile Lys Arg
            100                 105

<210> SEQ ID NO 57
<211> LENGTH: 13
<212> TYPE: PRT
<213> ORGANISM: Artificial Sequence
<220> FEATURE:
<223> OTHER INFORMATION: mAb 3H4 Vh CDR1

<400> SEQUENCE: 57

Lys Ala Ser Gly Tyr Thr Phe Thr Asp Tyr Tyr Ile Asn
1               5                   10

<210> SEQ ID NO 58
<211> LENGTH: 17
<212> TYPE: PRT
<213> ORGANISM: Artificial Sequence
<220> FEATURE:
<223> OTHER INFORMATION: mAb 3H4 Vh CDR2

<400> SEQUENCE: 58

Trp Ile Tyr Pro Gly Ser Val Asn Thr Lys Tyr Asn Glu Lys Phe Arg
1               5                   10                  15

Gly

<210> SEQ ID NO 59
<211> LENGTH: 8
<212> TYPE: PRT
<213> ORGANISM: Artificial Sequence
<220> FEATURE:
<223> OTHER INFORMATION: mAb 3H4 Vh CDR3

<400> SEQUENCE: 59

Tyr Ser Asn Trp Phe Phe Asp Val
1               5

<210> SEQ ID NO 60
<211> LENGTH: 11
<212> TYPE: PRT
<213> ORGANISM: Artificial Sequence
<220> FEATURE:
<223> OTHER INFORMATION: mAb 3H4 Vl CDR1

<400> SEQUENCE: 60

Arg Ala Ser Gln Glu Ile Ser Gly Tyr Leu Ser
1               5                   10

<210> SEQ ID NO 61
<211> LENGTH: 7
<212> TYPE: PRT
<213> ORGANISM: Artificial Sequence
<220> FEATURE:
<223> OTHER INFORMATION: mAb 3H4 Vl CDR2

<400> SEQUENCE: 61

Ala Ala Ser Thr Leu Asp Ser
1               5

<210> SEQ ID NO 62
<211> LENGTH: 9
<212> TYPE: PRT
<213> ORGANISM: Artificial Sequence
<220> FEATURE:
<223> OTHER INFORMATION: mAb 3H4 Vl CDR3

<400> SEQUENCE: 62

Leu Gln Tyr Ala Ser Tyr Pro Tyr Thr
1               5

<210> SEQ ID NO 63
<211> LENGTH: 118
<212> TYPE: PRT
<213> ORGANISM: Artificial Sequence
<220> FEATURE:
<223> OTHER INFORMATION: mAb 6D10 Vh

<400> SEQUENCE: 63

Glu Val Lys Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Val Ser Ser Ala Ser Ser Val Ile His Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Gly Tyr Tyr Gly Thr Trp Phe Pro Tyr Trp Gly Gln Gly
            100                 105                 110

Thr Leu Val Thr Val Ser
        115

<210> SEQ ID NO 64
<211> LENGTH: 13

```
<212> TYPE: PRT
<213> ORGANISM: Artificial Sequence
<220> FEATURE:
<223> OTHER INFORMATION: mAb 6D10 Vh CDR1

<400> SEQUENCE: 64

Ala Ala Ser Gly Phe Thr Phe Ser Ser Phe Gly Met His
 1               5                  10

<210> SEQ ID NO 65
<211> LENGTH: 17
<212> TYPE: PRT
<213> ORGANISM: Artificial Sequence
<220> FEATURE:
<223> OTHER INFORMATION: mAb 6D10 Vh CDR2

<400> SEQUENCE: 65

Tyr Val Ser Ser Ala Ser Ser Val Ile His Tyr Ala Asp Thr Val Lys
 1               5                  10                  15

Gly

<210> SEQ ID NO 66
<211> LENGTH: 10
<212> TYPE: PRT
<213> ORGANISM: Artificial Sequence
<220> FEATURE:
<223> OTHER INFORMATION: mAb 6D10 Vh CDR3

<400> SEQUENCE: 66

Ser Gly Tyr Tyr Gly Thr Trp Phe Pro Tyr
 1               5                  10

<210> SEQ ID NO 67
<211> LENGTH: 112
<212> TYPE: PRT
<213> ORGANISM: Artificial Sequence
<220> FEATURE:
<223> OTHER INFORMATION: mAb 2.3A9 Vh

<400> SEQUENCE: 67

Gln Val Gln Leu Gln Gln Ser Asp Ala Glu Leu Val Lys Pro Gly Thr
 1               5                  10                  15

Ser Val Lys Ile Ser Cys Lys Ala Ser Gly Tyr Thr Phe Thr Asp His
            20                  25                  30

Ala Ile His Trp Leu Lys Gln Glu Pro Asp Gln Gly Leu Glu Trp Ile
        35                  40                  45

Gly Tyr Ile Ser Pro Gly Tyr Gly Asp Ile Glu Tyr Asn Glu Lys Phe
    50                  55                  60

Lys Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                85                  90                  95

Lys Val Thr Thr Gly Tyr Trp Gly Gln Gly Thr Thr Leu Thr Val Ser
            100                 105                 110

<210> SEQ ID NO 68
<211> LENGTH: 113
<212> TYPE: PRT
<213> ORGANISM: Artificial Sequence
<220> FEATURE:
<223> OTHER INFORMATION: mAb 2.3A9 Vl

<400> SEQUENCE: 68

Asp Val Leu Met Thr Gln Thr Pro Leu Thr Leu Ser Val Thr Ile Gly
```

```
                1               5                  10                  15
Gln Pro Ala Ser Ile Ser Cys Lys Ser Ser Gln Ser Leu Leu Asn Ser
                20                  25                  30

Asp Gly Lys Thr Tyr Leu Asn Trp Leu Leu Gln Arg Pro Gly Gln Ser
                35                  40                  45

Pro Lys Arg Leu Ile Tyr Leu Val Ser Glu Leu Asp Ser Gly Val Pro
            50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro His Thr Phe Gly Ala Gly Thr Lys Leu Glu Leu Lys
                100                 105                 110

Arg

<210> SEQ ID NO 69
<211> LENGTH: 13
<212> TYPE: PRT
<213> ORGANISM: Artificial Sequence
<220> FEATURE:
<223> OTHER INFORMATION: mAb 2.3A9 Vh CDR1

<400> SEQUENCE: 69

Lys Ala Ser Gly Tyr Thr Phe Thr Asp His Ala Ile His
1               5                   10

<210> SEQ ID NO 70
<211> LENGTH: 17
<212> TYPE: PRT
<213> ORGANISM: Artificial Sequence
<220> FEATURE:
<223> OTHER INFORMATION: mAb 2.3A9 Vh CDR2

<400> SEQUENCE: 70

Tyr Ile Ser Pro Gly Tyr Gly Asp Ile Glu Tyr Asn Glu Lys Phe Lys
1               5                   10                  15

Gly

<210> SEQ ID NO 71
<211> LENGTH: 4
<212> TYPE: PRT
<213> ORGANISM: Artificial Sequence
<220> FEATURE:
<223> OTHER INFORMATION: mAb 2.3A9 Vh CDR3

<400> SEQUENCE: 71

Thr Thr Gly Tyr
1

<210> SEQ ID NO 72
<211> LENGTH: 16
<212> TYPE: PRT
<213> ORGANISM: Artificial Sequence
<220> FEATURE:
<223> OTHER INFORMATION: mAb 2.3A9 Vl CDR1

<400> SEQUENCE: 72

Lys Ser Ser Gln Ser Leu Leu Asn Ser Asp Gly Lys Thr Tyr Leu Asn
1               5                   10                  15

<210> SEQ ID NO 73
<211> LENGTH: 7
<212> TYPE: PRT
```

```
<213> ORGANISM: Artificial Sequence
<220> FEATURE:
<223> OTHER INFORMATION: mAb 2.3A9 V1 CDR2

<400> SEQUENCE: 73

Leu Val Ser Glu Leu Asp Ser
 1               5

<210> SEQ ID NO 74
<211> LENGTH: 9
<212> TYPE: PRT
<213> ORGANISM: Artificial Sequence
<220> FEATURE:
<223> OTHER INFORMATION: mAb 2.3A9 V1 CDR3

<400> SEQUENCE: 74

Trp Gln Gly Thr His Phe Pro His Thr
 1               5

<210> SEQ ID NO 75
<211> LENGTH: 218
<212> TYPE: PRT
<213> ORGANISM: Artificial Sequence
<220> FEATURE:
<223> OTHER INFORMATION: mAb 1B8 V1 and human kappa constant

<400> SEQUENCE: 75
```

Asp Ile Val Leu Thr Gln Ser Pro Thr Ser Leu Ala Val Ser Leu Gly
 1               5                  10                  15

Gln Arg Ala Thr Ile Ser Cys Arg Ala Ser Glu Ser Val Asp Asn Ser
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Pro Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Trp Thr Phe Gly Gly Gly Thr Glu Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

```
<210> SEQ ID NO 76
<211> LENGTH: 450
<212> TYPE: PRT
<213> ORGANISM: Artificial Sequence
<220> FEATURE:
```

<223> OTHER INFORMATION: mAb 1B8 Vh and human IgG constant

<400> SEQUENCE: 76

```
Glu Val Gln Leu Val Leu Ser Gly Gly Gly Phe Val Gln Pro Gly Gly
 1               5                  10                  15
Ser Leu Lys Leu Ser Cys Ala Ala Ser Gly Phe Thr Phe Ser Ser Tyr
            20                  25                  30
Ala Met Ser Trp Val Arg Gln Asn Pro Glu Arg Arg Leu Val Trp Val
        35                  40                  45
Ala Thr Ile Thr Gly Gly Arg Asn Thr Tyr Tyr Pro Asp Ser Val
    50                  55                  60
Lys Gly Arg Phe Thr Ile Ser Arg Asp Asn Ala Lys Asn Thr Leu Tyr
 65                  70                  75                  80
Leu Gln Met Ser Ser Leu Arg Ser Glu Asp Thr Ala Met Tyr Tyr Cys
                85                  90                  95
Thr Arg Gln Gly Tyr Asp Gly Tyr Thr Trp Phe Ala Tyr Trp Gly Gln
            100                 105                 110
Gly Thr Leu Val Thr Val Ser Ala Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
```

```
                     405                 410                 415
Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 77
<211> LENGTH: 446
<212> TYPE: PRT
<213> ORGANISM: Artificial Sequence
<220> FEATURE:
<223> OTHER INFORMATION: mAb 1B8 Vh and human IgG2m4 constant

<400> SEQUENCE: 77

Glu Val Gln Leu Val Leu Ser Gly Gly Gly Phe Val Gln Pro Gly Gly
  1               5                  10                  15

Ser Leu Lys Leu Ser Cys Ala Ala Ser Gly Phe Thr Phe Ser Ser Tyr
             20                  25                  30

Ala Met Ser Trp Val Arg Gln Asn Pro Glu Arg Arg Leu Val Trp Val
         35                  40                  45

Ala Thr Ile Thr Gly Gly Gly Arg Asn Thr Tyr Tyr Pro Asp Ser Val
     50                  55                  60

Lys Gly Arg Phe Thr Ile Ser Arg Asp Asn Ala Lys Asn Thr Leu Tyr
 65                  70                  75                  80

Leu Gln Met Ser Ser Leu Arg Ser Glu Asp Thr Ala Met Tyr Tyr Cys
                 85                  90                  95

Thr Arg Gln Gly Tyr Asp Gly Tyr Thr Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Thr
            180                 185                 190

Ser Ser Asn Phe Gly Thr Gln Thr Tyr Thr Cys Asn Val Asp His Lys
        195                 200                 205

Pro Ser Asn Thr Lys Val Asp Lys Thr Val Glu Arg Lys Cys Cys Val
    210                 215                 220

Glu Cys Pro Pro Cys Pro Ala Pro Pro Val Ala Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Phe Arg Val Val Ser Val
    290                 295                 300

Leu Thr Val Leu His Gln Asp Trp Leu Asn Gly Lys Glu Tyr Lys Cys
305                 310                 315                 320
```

```
Lys Val Ser Asn Lys Gly Leu Pro Ser Ser Ile Glu Lys Thr Ile Ser
            325                 330                 335

Lys Thr Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Met Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```